(12) United States Patent
Ichikawa et al.

(10) Patent No.: US 8,802,352 B2
(45) Date of Patent: *Aug. 12, 2014

(54) SALT, PHOTORESIST COMPOSITION AND METHOD FOR PRODUCING PHOTORESIST PATTERN

(75) Inventors: Koji Ichikawa, Osaka (JP); Yuichi Mukai, Osaka (JP); Isao Yoshida, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/567,892

(22) Filed: Aug. 6, 2012

(65) Prior Publication Data

US 2013/0040239 A1 Feb. 14, 2013

(30) Foreign Application Priority Data

Aug. 8, 2011 (JP) ................................. 2011-172729

(51) Int. Cl.
*G03F 7/004* (2006.01)
*G03F 7/26* (2006.01)
*G03F 7/027* (2006.01)
*C07C 69/753* (2006.01)

(52) U.S. Cl.
USPC ......... 430/270.1; 430/326; 560/116; 560/117

(58) Field of Classification Search
USPC ......... 430/270.1, 326; 526/242–263; 560/117
See application file for complete search history.

(56) References Cited

U.S. PATENT DOCUMENTS

| 2007/0122750 A1 | 5/2007 | Yamaguchi et al. |
| 2011/0117495 A1* | 5/2011 | Ichikawa et al. ............ 430/270.1 |
| 2012/0203030 A1* | 8/2012 | Oh et al. .......................... 562/42 |
| 2012/0315580 A1* | 12/2012 | Masuyama et al. ........ 430/285.1 |

FOREIGN PATENT DOCUMENTS

| JP | 2011-52211 A | 3/2011 |
| JP | 2012006911 A | * 1/2012 |

OTHER PUBLICATIONS

Ichikawa et al., JP 2012-006911 A (English translation), 2012.*

* cited by examiner

*Primary Examiner* — Amanda C. Walke
(74) *Attorney, Agent, or Firm* — Birch, Stewart, Kolasch & Birch, LLP

(57) ABSTRACT

A salt represented by formula (I):

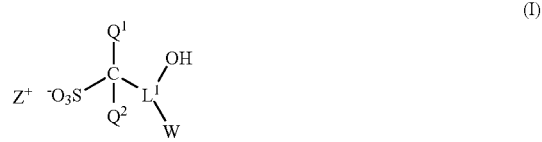

wherein $Q^1$, $Q^2$, $L^1$, W, and $Z^+$ are defined in the specification.

6 Claims, 1 Drawing Sheet

(a)

(b)

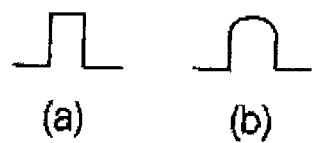
(a)  (b)

SALT, PHOTORESIST COMPOSITION AND METHOD FOR PRODUCING PHOTORESIST PATTERN

This nonprovisional application claims priority under 35 U.S.C. §119(a) on Patent Application No. 2011-172729 filed in JAPAN on Aug. 8, 2011, the entire contents of which are hereby incorporated by reference.

FIELD OF THE INVENTION

The present invention relates to a salt, a photoresist composition and a method for producing a photoresist pattern.

BACKGROUND OF THE INVENTION

A photoresist composition to be used for semiconductor usually comprises a salt as an acid generator.

US2007/0122750A mentions a salt represented by the following formula as an acid generator.

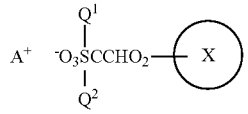

(wherein X represents monocyclic or polycyclic hydrocarbon group having 3 to 30 carbon atoms or the like, $Q^1$ and $Q^2$ each independently represent a fluorine atom or a C1-C6 perfluoroalkyl group, and $A^+$ represents an organic cation).

SUMMARY OF THE INVENTION

The present invention relates to the followings:
<1> A salt represented by formula (I);

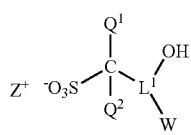

wherein $Q^1$ and $Q^2$ each independently represent a fluorine atom or a C1-C6 perfluoroalkyl group,
$L^1$ represents a C1-C20 trivalent aliphatic saturated hydrocarbon group in which a hydrogen atom bonded to a methylene group of aliphatic saturated hydrocarbon chain moiety can be replaced by a fluorine atom or a hydroxy group and in which a methylene group can be replaced by an oxygen atom, —$NR^2$— or a carbonyl group, where $R^2$ represents a hydrogen atom or a C1-C6 alkyl group,
the hydroxyl group of $L^1$-OH is positioned on the aliphatic saturated, hydrocarbon chain moiety of $L^1$,
W represents a C3-C36 alicyclic hydrocarbon group
in which a methylene group can be replaced by an oxygen atom, a sulfur atom, a carbonyl group or a sulfonyl group, and in which a hydrogen atom can be replaced by a hydroxy group, a C1-C12 alkyl group, a C1-C12 alkoxy group, C3-C18 alicyclic hydrocarbon group or C6-C14 aromatic hydrocarbon group, and
$Z^+$ represents an organic cation.

<2> The salt according to <1>, wherein the moiety $L^1$-OH of formula (I) is represented by formula ($L^1$-1)

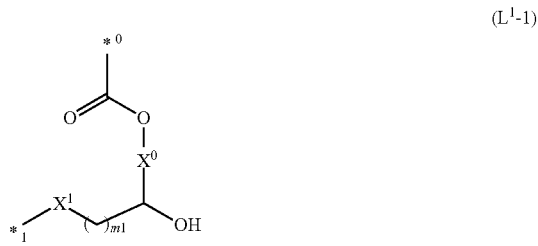

wherein $X^0$ represents a single bond,
a C1-C14 divalent aliphatic hydrocarbon group which can have a fluorine atom or a hydroxy group, or a group represented by formula (a-1)

$$-A^{10}-(-X^{10}-A^{11}-)_s-X^{11}-A^{12}-* \qquad (a-1)$$

where s represents an integer of 0 or 1, $X^{10}$ and $X^{11}$ each independently represent an oxygen atom, a carbonyl group, a carbonyloxy group, or an oxycarbonyl group, $A^{10}$, $A^{11}$ and $A^{12}$ each independently represent a C1-C12 divalent aliphatic hydrocarbon group which can have a fluorine atom or a hydroxy group, * represents a binding position to a carbon atom,
$X^1$ represents —O-*¹, —$NR^2$-*¹, —O—CO-*¹, —O—$CH_2$-*¹, —O—$CH_2$—CO—O-*¹ or —$NR^2$—$CH_1$-*¹ where *¹ represents a binding position to W,
*⁰ represents a binding position to a carbon atom binding to $Q^1$ and $Q^2$, and $m^1$ represents an integer of 0 to 6.
<3> The salt according to <2>, wherein $X^1$ represents —O-*¹, —$NR^2$-*¹, —O—CO-*¹, —O—$CH_2$-*¹, or —$NR^2$—$CH_2$-*¹ where *¹ represents a binding position to W.
<4> The salt according to any one of <1> to <3>, wherein Z' is a triarylsulfonium cation.
<5> A photoresist composition, which comprises the salt according to any one of <1> to <4> and a resin which is hardly soluble or insoluble but soluble in an aqueous alkali solution by action of an acid.
<6> The photoresist composition according to <5>, which further comprises a basic compound.
<7> A process for producing a photoresist pattern comprising the following steps (1) to (5):
(1) a step of applying the photoresist composition according to <5> or <6> on a substrate,
(2) a step of forming a photoresist film by conducting drying,
(3) a step of exposing the photoresist film to radiation,
(4) a step of baking the exposed photoresist film, and
(5) a step of developing the baked photoresist film, thereby forming a photoresist pattern.

The salt of the present invention can give a photoresist composition which can provide a photoresist pattern without profile of a dummy pattern but with fine profile even when optical proximity correction is adopted to a process for producing photoresist pattern by using a mask with a dummy pattern.

BRIEF DESCRIPTION OF DRAWINGS

FIG. 1 illustrates cross-section views of photoresist patterns.

DESCRIPTION OF PREFERRED EMBODIMENTS

The salt of the present invention is represented by the formula (I). Hereinafter, such salt is sometimes referred to as "SALT (I)".

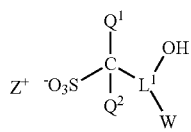

(I)

wherein $Q^1$ and $Q^2$ each independently represent a fluorine atom or a C1-C6 perfluoroalkyl group, $L^1$ represents a C1-C20 trivalent aliphatic saturated hydrocarbon group in which a hydrogen atom bonded to a methylene group of aliphatic saturated hydrocarbon chain moiety can be replaced by a fluorine atom or a hydroxy group and in which a methylene group can be replaced by an oxygen atom, —$NR^2$— or a carbonyl group, where $R^2$ represents a hydrogen atom or a C1-C6 alkyl group, the hydroxy group of $L^1$-OH is positioned on the aliphatic saturated hydrocarbon chain moiety of $L^1$, W represents a C3-C36 alicyclic hydrocarbon group
in which a methylene group can be replaced by an oxygen atom, a sulfur atom, a carbonyl group or a sulfonyl group, and in which a hydrogen atom can be replaced by a hydroxy group, a C1-C12 alkyl group, a C1-C12 alkoxy group, C3-C18 alicyclic hydrocarbon group or C6-C14 aromatic hydrocarbon group, and $Z^+$ represents an organic cation.

Hereinafter, the moiety corresponding to the part except $Z^+$ in formula (I) and having a negative charge is sometimes referred to as "sulfonic acid anion".

The perfluoroalkyl group represented by $Q^1$ or $Q^2$ includes a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. $Q^1$ and $Q^2$ each independently represent preferably a fluorine atom and a trifluoromethyl group, more preferably a fluorine atom.

The C1-C20 trivalent aliphatic saturated hydrocarbon group represented by $L^1$, which may be a linear or branched chain, or an alicyclic hydrocarbon group, includes a C1-C20 alkanetriyl group such as a methine group, a ethan-1,1,2-triyl group, a propane-1,2,3-triyl group, butane-1,2,4-triyl group, a pentane-1,2,5-triyl group, a pentane-1,3,5-triyl group, a hexane-1,2,6-triyl group, a hexane-1,3,6-triyl group, a heptane-1,2,7-triyl group, a heptane-1,3,7-triyl group, an octane-1,2,8-triyl group, an octane-1,3,8-triyl group, group, an octane-1,4,8-triyl group, a nonane-1,2,9-triyl group, a nonane-1,3,9-triyl group, a nonane-1,4,9-triyl group, a decane-1,2,10-triyl group, a decane-1,3,10-triyl group, a decane-1,4,10-triyl group, a decane-1,5,10-triyl group, an undecane-1,2,11-triyl group, an undecane-1,3,11-triyl group, an undecane-1,4,11-triyl group, an undecane-1,5,11-triyl group, a dodecane-1,2,12-triyl group, a dodecane-1,3,12-triyl group, a dodecane-1,4,12-triyl group, a dodecane-1,5,12-triyl group, a dodecane-1,6,12-triyl group, a tridecane-1,2,13-triyl group, a tridecane-1,2,13-triyl group, a tridecane-1,3,13-triyl group, a tridecane-1,4,13-triyl group, a tridecane-1,5,13-triyl group, a tridecane-1,6,13-triyl group, a tetradecano-1,2,14-triyl group, a tetradecane-1,3,14-triyl group, a tetradocane-1,4,14-triyl group, a tetradecane-1,5,14-triyl group, a tetradecano-1,6,14-triyl group, a tetradecane-1,7,14-triyl group, a pentadeoane-1,2,15-triyl group, a pentadecane-1,3,15-triyl group, a pentadecane-1,4,15-triyl group, a pentadecane-1,5,15-triyl group, a pentadecane-1,6,15-triyl group, a pentadecane-1,7,15-triyl group, a hexadecane-1,2,16-triyl group, a hexadecane-1,3,16-triyl group, a hexadecane-1,4,16-triyl group, a hexadecane-1,5,16-triyl group, a hexadecane-1,6,16-triyl group, a hexadecane-1,7,16-triyl group, a hexadecane-1,8,16-triyl group, a heptadecane-1,2,17-triyl group, a heptadecane-1,3,17-triyl group, a heptadecane-1,4,17-triyl group, a heptadecane-1,5,17-triyl group, a heptadecane-1,6,17-triyl group, a heptadecane-1,7,17-triyl group, and a heptadecane-1,8,17-triyl group; and trivalent alicyclic hydrocarbon groups having a structure in which three hydrogen groups have been removed from the group represented by formula (KA-1), (KA-2), (KA-3), (KA-4), (KA-5), (KA-6), (KA-7), (KA-8), (KA-9), (KA-10), (KA-11), (KA-12), (KA-13), (KA-14), (KA-15), (KA-16), (KA-17), (KA-18), (KA-19), (KA-20), (KA-21) or (KA-22).

(KA-1)

(KA-2)

(KA-3)

(KA-4)

(KA-5)

(KA-6)

(KA-7)

(KA-8)

(KA-9)

-continued (KA-10) 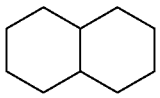

(KA-11) 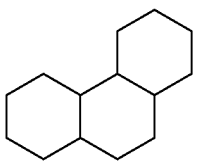

(KA-12) 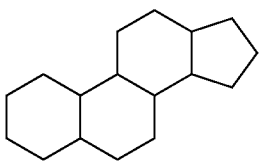

(KA-13) 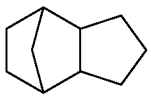

(KA-14) 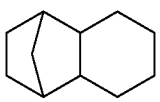

(KA-15) 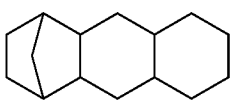

(KA-16) 

(KA-17) 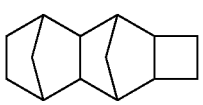

(KA-18) 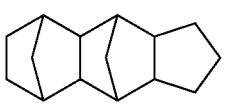

(KA-19) 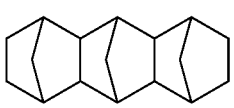

(KA-20) 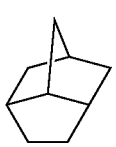

(KA-21) 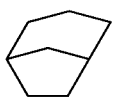

-continued (KA-22) 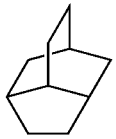

The C1-C20 trivalent aliphatic saturated hydrocarbon group may be a C4-C20 trivalent hydrocarbon group which consists of C1-C17 alkanediyl group and a trivalent alicyclic group or a C4-C20 hydrocarbon group which consists of an alkanetriyl group and a divalent alicyclic hydrocarbon group.

Examples of the C1-C17 divalent saturated hydrocarbon group include a C1-C17 linear alkanediyl group such as a methylene group, an ethylene group, a propane-1,3-diyl group, a propane-1,2-diyl group, a butane-1,4-diyl group, a butane-1,3-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group, a heptadecane-1,17-diyl group, an ethane-1,1-diyl group, a propane-1,1-diyl group and a propane-2,2-diyl group; a C2-C17 branched alkanediyl group such as a butane-1,3-diyl group, a 2-methylpropane-1,3-diyl group, a 2-methylpropane-1,2-diyl group, a pentane-1,4-diyl group and a 2-methylbutane-1,4-diyl group; a divalent monocyclic saturated hydrocarbon group such as a cyclobutane-1,3-diyl group, a cyclopentane-1,3-diyl group, a cyclohexane-1,2-diyl group, a 1-methylcyclohexane-1,2-diyl group, a cyclohexane-1,4-diyl group, a cyclooctane-1,2-diyl group and a cyclooctane-1,5-diyl group; a divalent polycyclic saturated hydrocarbon group such as a norbornane-2,3-diyl group, a norbornane-1,4-diyl group, a norbornane-2,5-diyl group, an adamantane-1,2-diyl group, an adamantane-1,5-diyl group and an adamantane-2,6-diyl group; and a group formed by combining two or more groups selected from the group consisting of the above-mentioned groups.

Methylene groups of the aliphatic saturated hydrocarbon represented by $L^1$ can be replaced by an oxygen atom, —$NR^2$— where $R^2$ represents a hydrogen atom or a C1-C6 alkyl group, or a carbonyl group. Considering easiness of producing the SALT (I), $L^1$ is preferably the aliphatic saturated hydrocarbon in which a methylene group has been replaced by an oxygen atom, —$NR^2$— where $R^2$ represents a hydrogen atom or a C1-C6 alkyl group, or a carbonyl group. When $L^1$ represents the aliphatic saturated hydrocarbon wherein a methylene group has been replaced by an oxygen atom, —$NR^2$— where $R^2$ represents a hydrogen atom or a C1-C6 alkyl group, or a carbonyl group, the moiety $L^1$-OH of formula (I) includes a divalent group represented by formula ($L^1$-1).

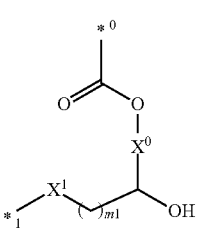

($L^1$-1)

wherein $X^0$ represents a single bond,
a C1-C14 divalent aliphatic hydrocarbon group which can have a fluorine atom or a hydroxy group, or
a group represented by formula (a-1)

(a-1)

where s represents an integer of 0 or 1, $X^{10}$ and $X^{11}$ each independently represent an oxygen atom, a carbonyl group, a carbonyloxy group, or an oxycarbonyl group, $A^{10}$, $A^{11}$ and $A^{12}$ each independently represent a C1-C12 divalent aliphatic hydrocarbon group which can have a fluorine atom or a hydroxy group,
* represents a binding position to a carbon atom, $X^1$ represents $—O-*^1$, $—NR^2-*^1$, $—O—CO-*^1$, $—O—CH_2-*^1$, $—O—CH_2—CO—O-*^1$ or $—NR^2—CH_2-*^1$, preferably $—O-*^1$, $—NR^2-*^1$, $—O—CO-*^1$, $—O—CH_2-*^1$ or $—NR^2—CH_2-*^1$, where
$*^1$ represents a binding position to W and $R^2$ represents a hydrogen atom or a C1-C6 alkyl group, and
$*^0$ represents a binding position to a carbon atom binding to $Q^1$ and $Q^2$, and
$m^1$ represents an integer of 0 to 6.
The C1-C14 divalent aliphatic hydrocarbon group represented by $X^0$ includes
a C1-C14 alkylene group such as a methylene group, an ethylene group, a propane-1,3-diyl group, a propane-1,2-diyl group, a butane-1,4-diyl group, a butane-1,3-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group; and a C3-C14 saturated cyclic hydrocarbon group such as a cyclobutane-1,3-diyl group, a cyclopentane-1,3-diyl group, a cyclohexane-1,2-diyl group, a 1-methylcyclohexane-1,2-diyl group, a cyclohexane-1,4-diyl group, a cyclooctane-1,2-diyl group and a cyclooctane-1,5-diyl group, a norbornane-2,3-diyl group, a norbornane-1,4-diyl group, a norbornane-2,5-diyl group, an adamantane-1,2-diyl group, an adamantane-1,5-diyl group, an adamantane-2,6-diyl group.
The C1-C12 divalent aliphatic hydrocarbon group represented by $A^{10}$, $A^{11}$ and $A^{12}$ includes
a C1-C12 alkylene group such as a methylene group, an ethylene group, a propylene group, a butylene group, a pentylene group, a hexylene group, a heptylene group, an octylene group, a decylene group, a dodecylene group; and
a C3-C12 divalent saturated cyclic hydrocarbon group such as a cyclopropylene group; cyclobutylene group, cyclopentylene group, cyclohexylene group, a cycloheptylene group, a cyclooctylene group, a cyclononylene group, a cyclodecylene group, a norbornylene group, an amadantylene group and an isonorbnornylene group.
$X^0$ is preferably a single bond, C1-C4 alkylene group, or a group represented by formula (a-1) where s is 0, $A^{10}$ is an adamantane ring,
$X^{11}$ is a carbonyloxy group and $A^{12}$ is C1-C4 alkylene group.
The C1-C6 alkyl group represented by $R^2$ includes a methyl group, an ethyl group, a propyl group, a butyl group, a pentyl group, and a hexyl group.
$X^1$ is preferably $—O—CO-*^1$ or $—O—CH_2—CO—O-*^1$ where $*^1$ represents a binding position to W as defined above.
The symbol "*" and "*" is alternatively used in the present application.

The divalent group represented by formula ($L^1$-l) includes the following ones;

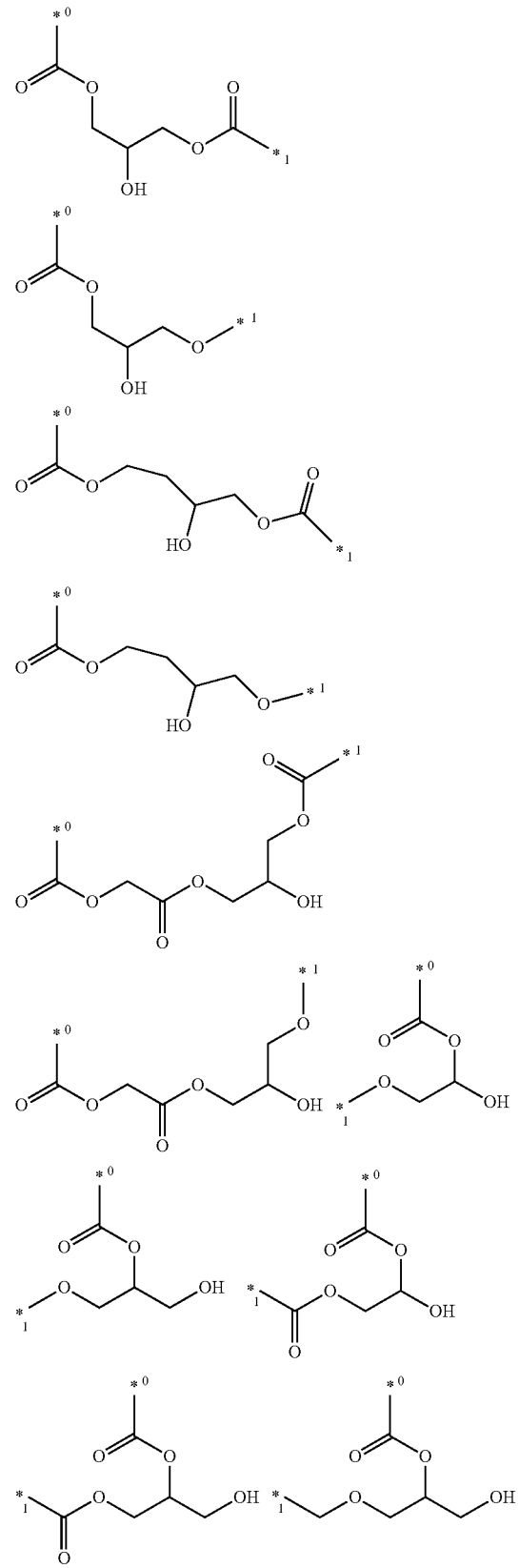

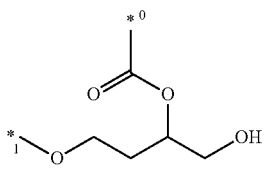
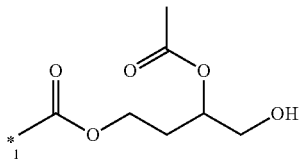
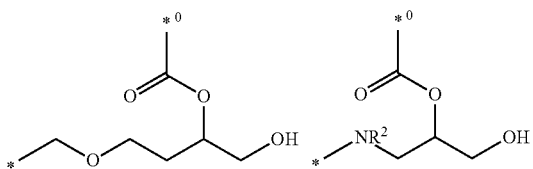
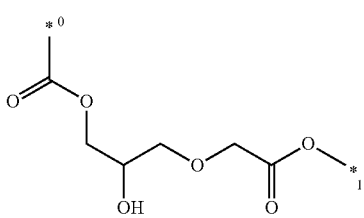
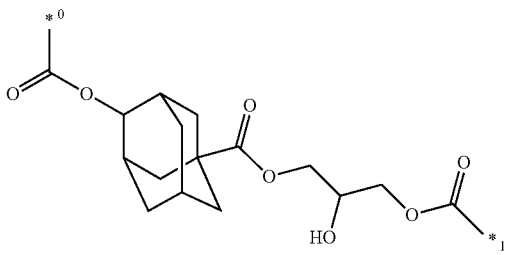
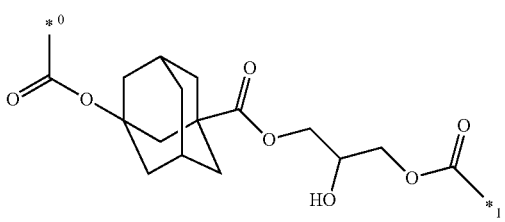
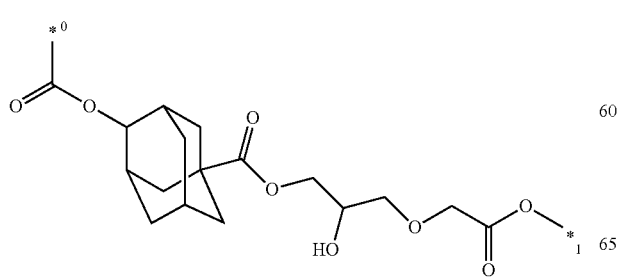

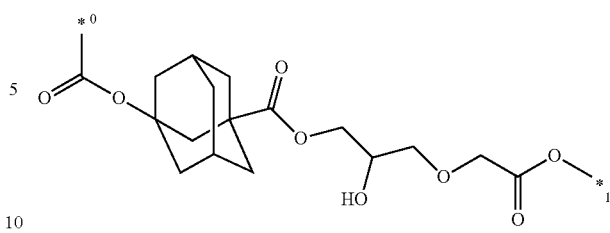

where $*^0$ represents a binding position to a carbon atom binding to $Q^1$ and $Q^2$, $R^2$ is the same as defined above, and $*^1$ represents a binding position to W.

In formula (I), the hydroxy group of $L^1$-OH is positioned on the aliphatic saturated hydrocarbon chain moiety of $L^1$.

In the trivalent aliphatic saturated hydrocarbon group represented by $L^1$, a hydrogen atom bonded to a methylene group of aliphatic saturated hydrocarbon chain moiety can be replaced by a fluorine atom or a hydroxy group.

Herein, the term "aliphatic saturated hydrocarbon chain moiety" means a chain alkylene group which constitutes the trivalent aliphatic saturated hydrocarbon group represented by $L^1$.

When $L^1$ represents a C1-C20 trivalent aliphatic saturated hydrocarbon group in which a hydrogen atom has been replaced by a fluorine atom, $L^1$-OH includes the following ones;

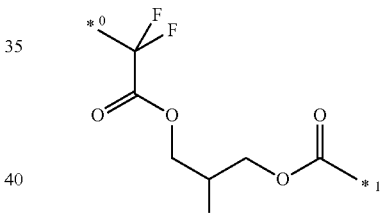
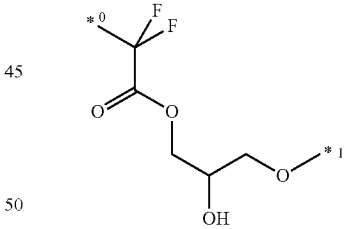
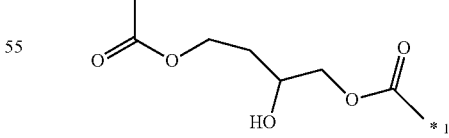
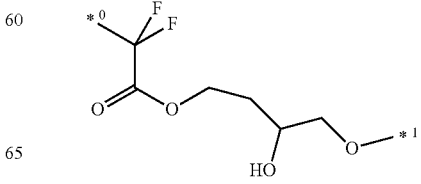

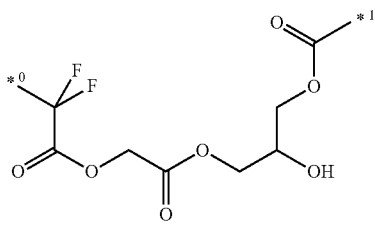

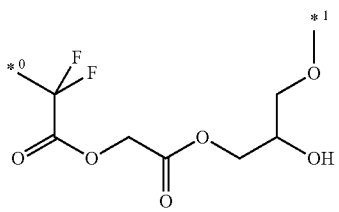

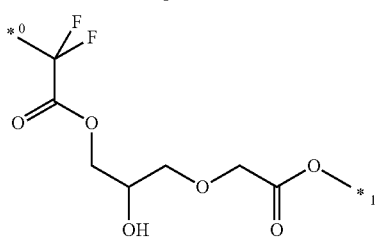

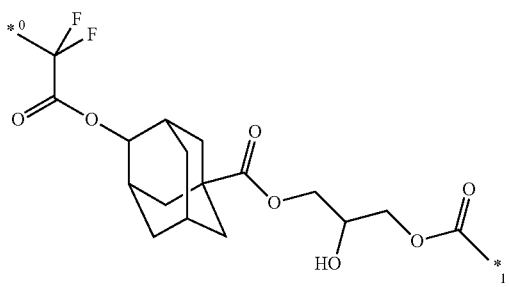

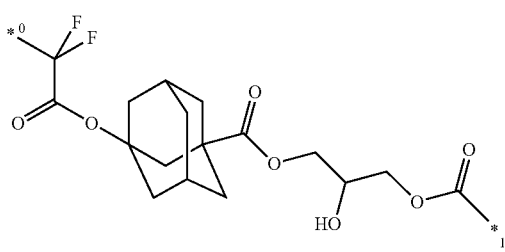

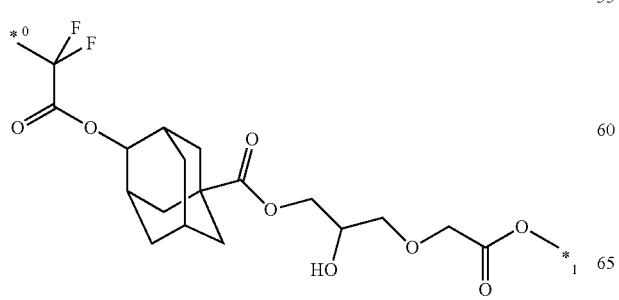

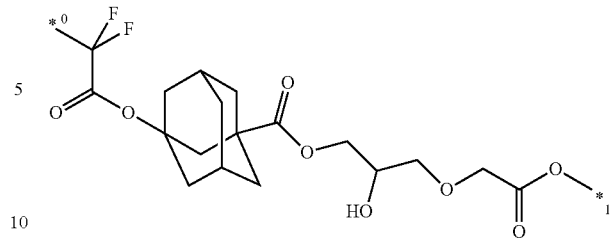

where *⁰ represents a binding position to a carbon atom binding to $Q^1$ and $Q^2$, and *¹ represents a binding position to W.

The alicyclic hydrocarbon group represented by W includes a monocyclic alicyclic hydrocarbon group and a polycyclic alicyclic hydrocarbon group.

The monocyclic alicyclic hydrocarbon group includes C3-C36 cycloalkyl groups such as groups in which one hydrogen atom has been removed from any one of the cycloalkanes represented by formulae (KA-1) to (KA-7) as mentioned above.

The polycyclic alicyclic hydrocarbon group includes apolycyclic groups such as groups in which one hydrogen atom has been removed from any one of the cycloalkanes represented by formulae (KA-8) to (KA-22) as mentioned above.

In the alicyclic hydrocarbon group represented by W, a methylene group can be replaced by an oxygen atom, a sulfur atom, a carbonyl group or a sulfonyl group, and a hydrogen atom can be replaced by a hydroxy group, a C1-C12 alkyl group, a C1-C12 alkoxy group, C3-C18 alicyclic hydrocarbon group or C6-C14 aromatic hydrocarbon group.

The alkyl group includes a methyl group, an ethyl group, a propyl group, an isopropyl group, a butyl group, a pentyl group, a hexyl group, a heptyl group, an octyl group, a decyl group, and a dodecyl group.

The alkoxy group includes a methoxy group, an ethoxy group, a propoxy group, a butoxy group, a pentyloxy group, a hexyloxy group, a heptyloxy group, an octyloxy group, a decyloxy group, and a dodecyloxy group.

The C3-C18 alicyclic hydrocarbon group includes a monocyclic alicyclic hydrocarbon group such as C3-C12 cycloalkyl groups (e.g. a cyclopentyl group, a cyclohexyl group, a methylcyclohexyl group, a dimethylcyclohexyl group, a cycloheptyl group and a cyclooctyl group); and a polycyclic alicyclic hydrocarbon group such as a decahydronaphthyl group, an adamantyl group, a norbornyl group.

The aromatic hydrocarbon group includes a phenyl group, a naphthyl group, an anthryl group, biphenyl group, phenanthryl group, fluorenyl group.

Specific examples of W include the following groups.

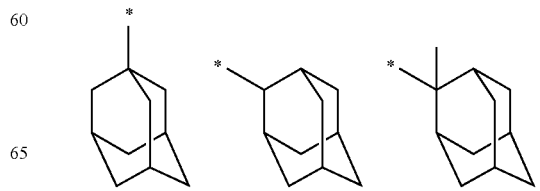

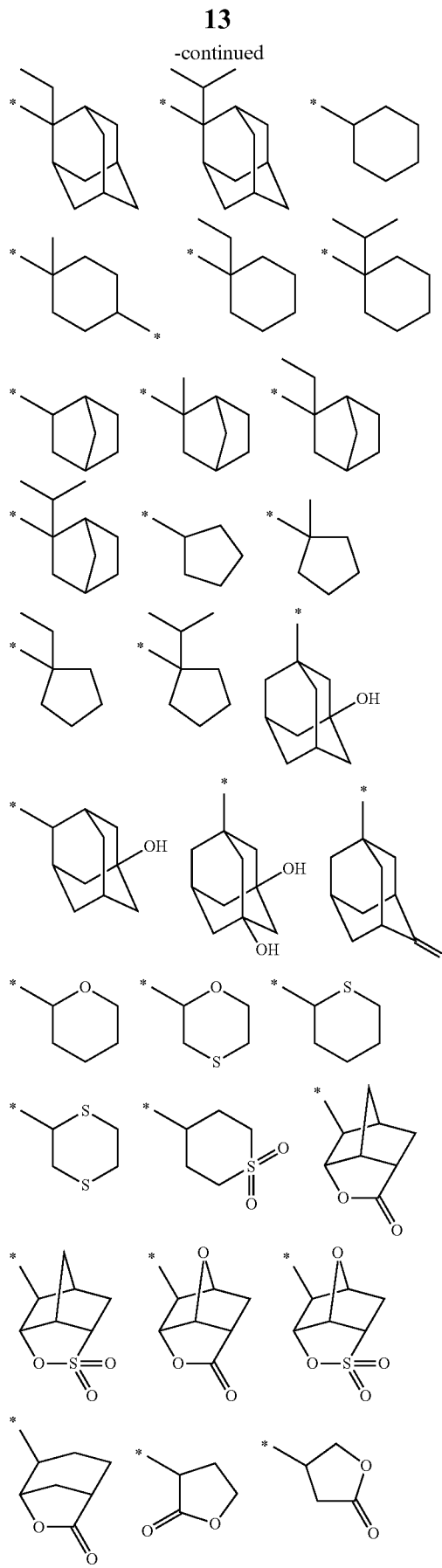

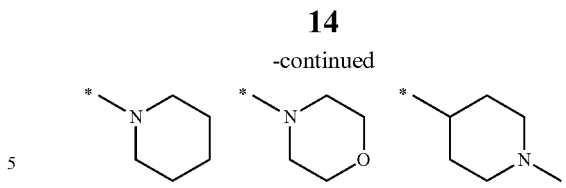

W includes preferably an adamantyl group, a norbornane group or a cycloalkyl group, more preferably an adamantyl group. Herein, the adamantyl group preferred as W includes one in which a methylene group has been replaced by carbonyl group, and in which an adamantyl group in which a hydrogen atom has been replaced by a hydroxy group.

Specific examples of the sulfonic acid anion include the following groups.

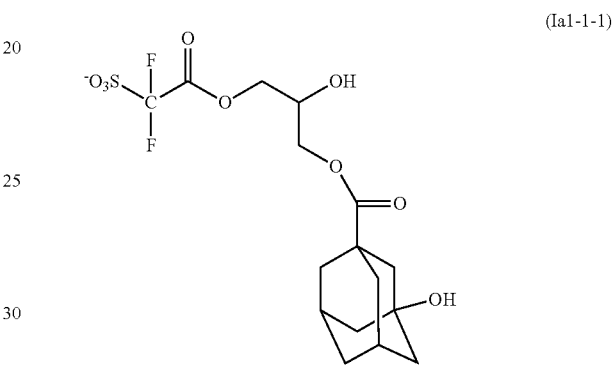

(Ia1-1-1)

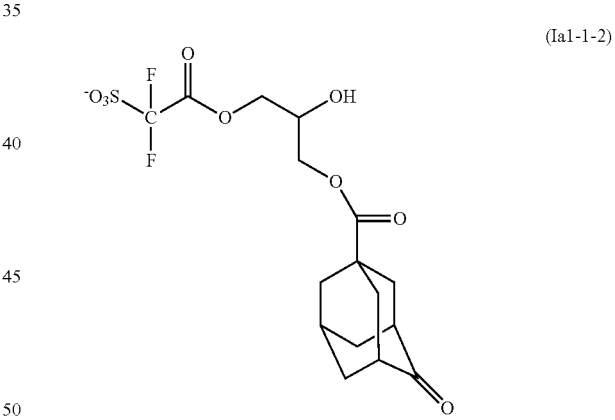

(Ia1-1-2)

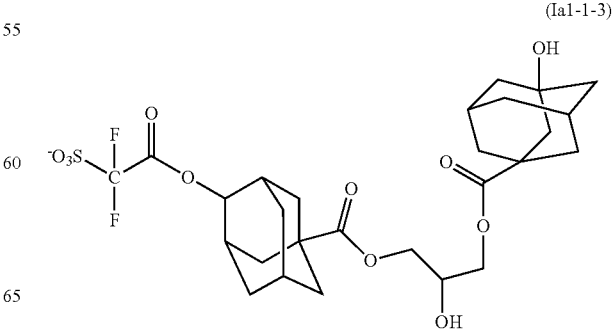

(Ia1-1-3)

-continued
(Ia1-4)
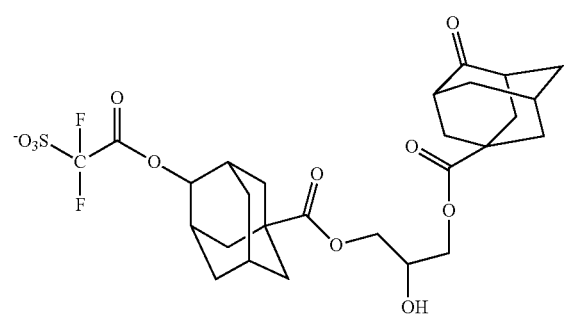
(Ia1-5)
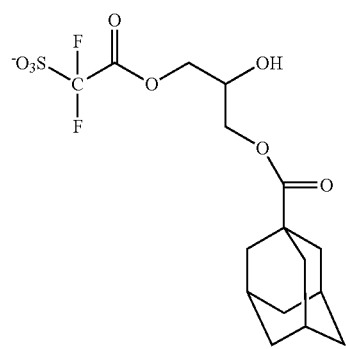
(Ia1-6)
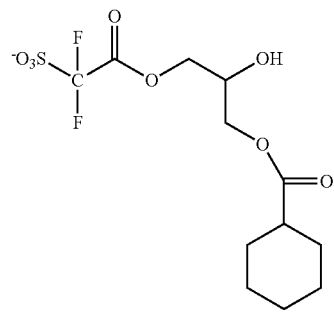
(Ia1-7)
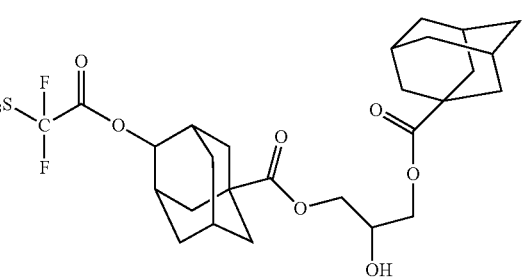
(Ia1-8)
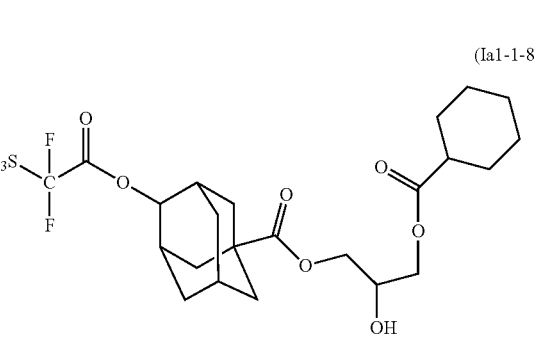
(Ia1-1-9)
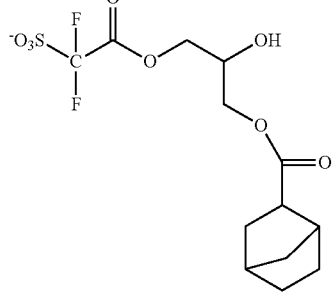
(Ia1-1-10)
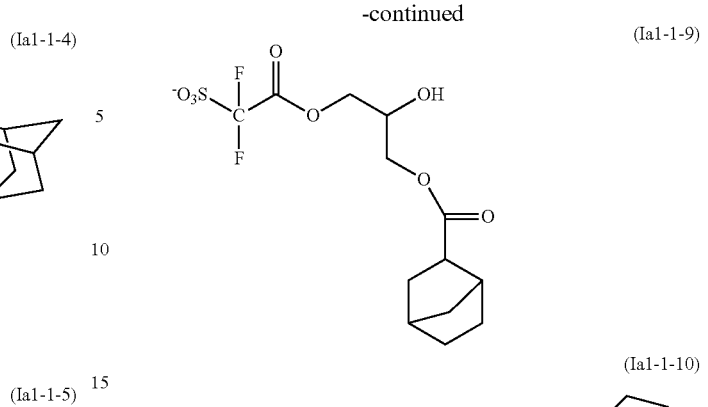
(Ia1-1-11)
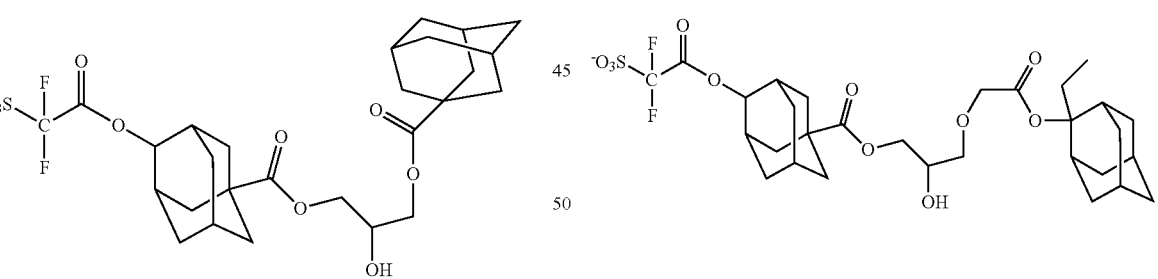
(Ia1-1-12)
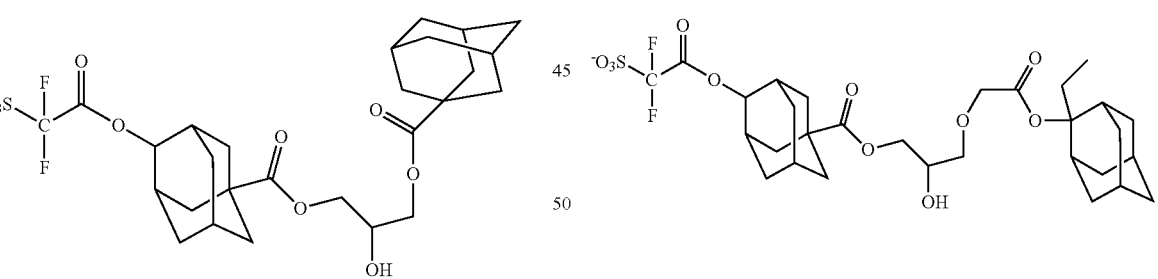
(Ia1-1-13)
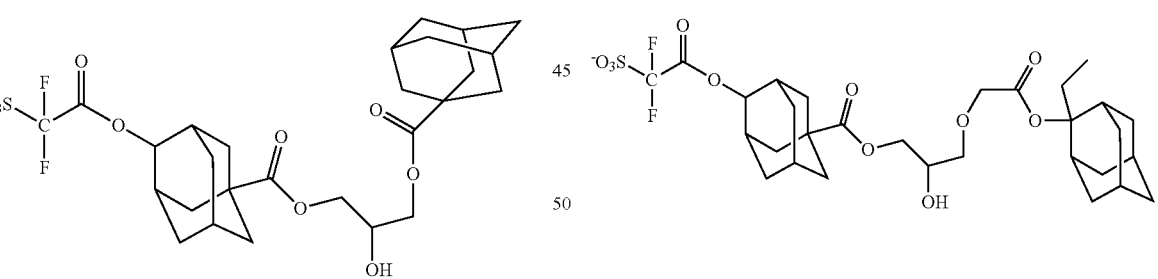

-continued (Ia1-1-14)

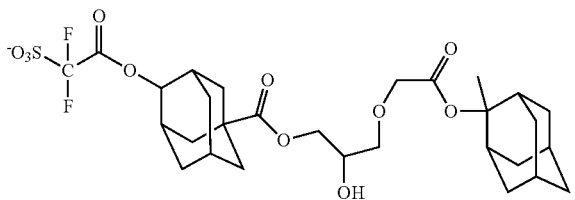

In the formula (I), $Z^+$ represents an organic cation.

Examples of the organic cation represented by $Z^+$ include an organic onium cation such as an organic sulfonium cation, an organic iodonium cation, an organic ammonium cation, a benzothiazolium cation and an organic phosphonium cation.

As the organic cation represented by $Z^+$, an organic sulfonium cation and an organic iodonium cation are preferable, and an organic cation represented by formulae (b2-1), (b2-2) (b2-3) and (b2-4) is more preferable.

(b2-1)

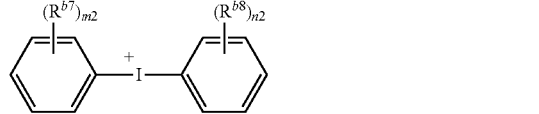
(b2-2)

(b2-3)

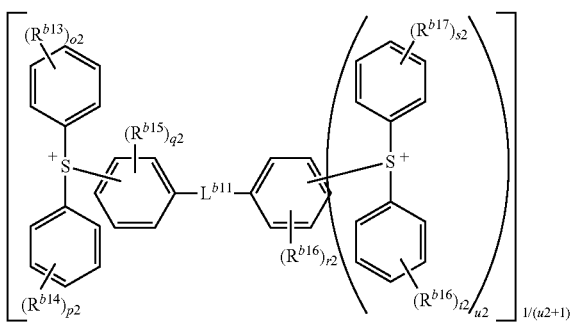
(b2-4)

wherein $R^{b4}$, $R^{b5}$ and $R^{b6}$ independently represent a C1-C30 aliphatic hydrocarbon group in which a hydrogen atom can be replaced by a halogen atom, a hydroxy group, C1-C12 alkoxy group, or C6-C18 aromatic hydrocarbon group; a C3-C18 alicyclic hydrocarbon group in which a hydrogen atom can be replaced by a halogen atom, a C2-C4 acyl group or a glycidyloxy group; a C6-C18 aromatic hydrocarbon group in which a hydrogen atom can be replaced by a halogen atom, a hydroxy group, C3-C18 alicyclic hydrocarbon group, or C1-C12 alkoxy group; or $R^{b4}$ and $R^{b5}$ are bonded each other together with the adjacent sulfur atom to form a C3-C18 saturated or unsaturated, nonaromatic or aromatic ring;
$R^{b7}$ and $R^{b8}$ are independently in each occurrence a hydroxy group, a C1-C12 alkyl group or a C1-C12 alkoxy group, m2 and n2 independently represents an integer of 0 to 5, $R^{b9}$ and $R^{b10}$ each independently represent a C1-C18 alkyl group or a C3-C18 alicyclic hydrocarbon group; or $R^{b9}$ and $R^{b10}$ are bonded each other to form a C2-C10 divalent acyclic hydrocarbon group which forms a 3- to 12-membered ring, preferably 3- to 7-membered ring together with the adjacent $—S^+—$, and one or more $—CH_2—$ in the divalent acyclic hydrocarbon group can be replaced by an oxygen atom, sulfur atom or carbonyl group;

$R^{b11}$ represents a C1-C18 alkyl group, a C3-C18 alicyclic hydrocarbon group, or C6-C18 aromatic hydrocarbon group;

$R^{b12}$ represents a C1-C18 alkyl group; a C3-C18 alicyclic hydrocarbon group; C6-C18 aromatic hydrocarbon group in which a hydrogen atom can be replaced by C1-C12 alkyl group, C1-C12 alkoxy group, C3-C18 alicyclic hydrocarbon group, or C1-C12 alkylcarbonyloxy group;

or the group in which the alkyl group has been combined with the aromatic hydrocarbon group; or $R^{b11}$ and $R^{b12}$ are bonded each other to form a C2-C10 divalent acyclic hydrocarbon group which forms a 2-oxocycloalkyl group together with the adjacent $—CHCO—$, and one or more $—CH_2—$ in the divalent acyclic hydrocarbon group can be replaced by an oxygen atom, sulfur atom or carbonyl group, $R^{b13}$, $R^{b14}$, $R^{b15}$, $R^{b16}$, $R^{b17}$ and $R^{b18}$ independently represent a hydroxy group, a C1-C12 aliphatic hydrocarbon group or a C1-C12 alkoxy group, $L^{b11}$ represents a sulfur atom or an oxygen atom, and o2, p2, s2 and t2 each independently represents an integer of 0 to 5, q2 and r2 each independently represents an integer of 0 to 4, and u2 represents 0 or 1.

As the aliphatic hydrocarbon group represented by $R^{b4}$, $R^{b5}$ and $R^{b6}$, preferred are a C1-C18 alkyl group in which a hydrogen atom can be replaced by a hydroxy group, or a C1-C12 alkoxy group, a C6-C18 aromatic hydrocarbon group.

The aliphatic hydrocarbon group represented by $R^{b9}$ or $R^{b10}$ includes preferably a C1-C12 alkyl group. The alicyclic hydrocarbon group represented by $R^{b9}$ or $R^{b10}$ is preferably C4-C12, alicyclic hydrocarbon group.

Preferable examples of the alkyl group represented by $R^{b4}$ to $R^{b6}$ include a methyl group, an ethyl group, a propyl group, an isopropyl group, a butyl group, a sec-butyl group, a tert-butyl group, a pentyl group, a hexyl group, an octyl group, a decyl group, a dodecyl group, a hexadecyl group, a pentadecyl group, a heptadecyl group and an octadecyl group, and more preferable examples thereof include a methyl group, an ethyl group, a propyl group and a butyl group. Preferable examples of the alicyclic hydrocarbon group represented by $R^{b4}$ to $R^{b6}$ include a cyclopropyl group, a cyclobutyl group, a cyclopentyl group, a cyclohexyl group, a cycloheptyl group, a cyclodecyl group, an adamantyl group, a 2-alkyladamantyl-2-yl group, a 1-tadaman-2-yl)alkane-1-yl group and an isobornyL group, and more preferable examples thereof include a cyclopentyl group and a cyclohexyl group. Preferable examples of the aromatic group represented by $R^{b4}$ to $R^{b6}$ include a phenyl group, a naphthyl group and an anthryl group, and a phenyl group is more preferable. Examples of the C1-C12 alkoxy group include a methoxy group, an ethoxy group, a propoxy group, a butoxy group, a pentyloxy group, a hexyloxy group, a heptyloxy group, an octyloxy group, a decyloxy group and a dodecyloxy group. Examples of the halogen atom include a fluorine atom, a chlorine atom, a bromine atom and an iodine atom. Examples of the C2-C4 acyl group include an acetyl group, a propyonyl group and a butyryl group.

Preferable examples of the alkyl group represented by $R^{b7}$ and $R^{b8}$ include a methyl group, an ethyl group, a propyl group, an isopropyl group, a butyl group, a sec-butyl group, a sec-butyl group, a pentyl group, a hexyl group, an octyl group and a 2-ethylhexyl group. Examples of the C1-C12 alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Preferable examples of the alkyl group represented by $R^{b9}$ to $R^{b12}$ include a methyl group, an ethyl group, a propyl group, an isopropyl group, a butyl group, a sec-butyl group, a tert-butyl group, a pentyl group, a hexyl group, an octyl group and a 2-ethylhexyl group. Such alkyl group preferably has 1 to 12 carbon atoms. Preferable examples of the alicyclic hydrocarbon group represented by $R^{b9}$ to $R^{11}$ include a cyclopropyl group, a cyclobutyl group, a cyclopentyl group, a cyclohexyl group, a cycloheptyl group, a cyclodecyl group, a 2-alkyl-2-adamantyl group, a 1-(1-adamantyl)-1-alkyl group and an isobornyl group. Preferable examples of the aromatic group represented by $R^{b12}$ include a phenyl group, 4-methylphenyl group, 4-ethylphenyl group, 4-tert butylphenyl group, 4-cyclohexylphenyl group, 4-methoxyphenyl group, biphenyl group and a naphthyl group, and a phenyl group is more preferable.

Preferable examples of the group in which the alkyl group has been combined with the aromatic hydrocarbon group represented by $R^{b12}$ include an aralkyl group such as benzyl group.

Preferable examples of the alkylcarbonyloxy group represented by $R^{b12}$ include a group consisting of an acyl group and an oxygen atom.

Examples of the C3-C12 divalent acyclic hydrocarbon group formed by bonding $R^{b9}$ and $R^{b10}$ include a trimethylene group, a tetramethylene group and a pentamethylene group. Examples of the ring group formed together with the adjacent $S^+$ and the divalent acyclic hydrocarbon group include a thiolan-1-ium ring (tetrahydrothiphenium ring), a thian-1-ium ring and a 1,4-oxathian-4-ium ring. A C3-C7 divalent acyclichydrocarbon group is preferable.

Examples of the C1-C10 divalent acyclic hydrocarbon group formed by bonding $R^{b11}$ and $R^{b12}$ include a methylene group, an ethylene group, a trimethylene group, a tetramethylene group and a pentamethylene group and examples of the ring group include oxocyclopentane ring, oxocyclonexane ring, oxonorbornane ring and oxoamadantane ring. A C1-C5 divalent acyclic hydrocarbon group is preferable.

Examples of the group in which the alkyl group has been combined with the aromatic hydrocarbon group include typically an aralkyl group, preferably benzyl group, As examples of the organic cations represented by formulae (b2-1) to (b2-4) include organic cations mentioned in JP2010-204646A1.

As the organic action represented by $Z^+$, an arylsulfonium cation is preferred, and a triarylsulfonium cation is more preferred.

Among the above-mentioned cations, the organic cations represented by formulae (b2-1) (b2-2) and (b2-3) are preferable, and the organic cations represented by formula (b2-1) are more preferable.

As the organic cations represented by formula (b2-1), more preferred is the cation represented by the formula (b2-1) in which any of $R^{b4}$, $R^{b5}$ and $R^{b6}$ is an aromatic hydrocarbon group, still more preferred is the cation represented by the formula (b2-1-1), especially more preferred is triphenylphosphonium cation or tritolylsulfonium cation.

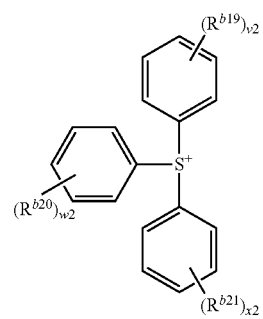

(b2-1-1)

wherein $R^{b19}$, $R^{b20}$ and $R^{b21}$ are independently in each occurrence a halogen atom (preferably a fluorine atom); a hydroxy group; a C1-C18 aliphatic hydrocarbon group in which a hydrogen atom can be replaced by a halogen group, a C2-C4 acyl group, or a grycidyloxy group; or a C1-C12 alkoxy group; and $R^{b19}$ and $R^{b20}$, $R^{b19}$ and $R^{b21}$ or $R^{b20}$ and $R^{b21}$ can be bonded each other to form a ring together with $S^+$, and v2, w2 and x2 independently each represent an integer of 0 to 5.

The aliphatic hydrocarbon group of $R^{b19}$, $R^{b20}$ and $R^{b21}$ includes an alkyl group and an alicyclic hydrocarbon group, preferably C1-C12 alkyl group and C4-C18 alicyclic hydrocarbon group.

The alkyl group represented by $R^{b19}$, $R^{b20}$ and $R^{b21}$ is preferably a C1-C12 alkyl group such as a methyl group, an ethyl group, a propyl group, an isopropyl group, a butyl group, a sec-butyl group, a tert-butyl group, a pentyl group, a hexyl group, an octyl group and a 2-ethylhexyl group.

The alicyclic hydrocarbon group represented by $R^{b19}$, $R^{b20}$ and $R^{b21}$ is preferably a C4-C18 alicyclic hydrocarbon group such as a cyclobutyl group, a cyclopentyl group, a cyclohexyl group, a cycloheptyl group, a cyclodecyl group, an adamantyl group, a 2-alkyladamantyl-2-yl group, a 1-(adaman-2-yl)alkane-1-yl group and an isobornyl group.

Each of $R^{b19}$, $R^{b20}$ and $R^{b21}$ is preferably a halogen atom (preferably a fluorine atom), a hydroxy group, a C1-C12 alkyl group and a C1-C12 alkoxy group, and more preferably a halogen atom (preferably a fluorine atom) and a C1-C6 alkyl group.

Preferably, the v2, w2 and x2 independently each represent 0 or 1.

Examples of the cation represented by the formula (b2-1-1) include the following ones.

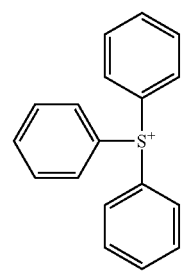

(b2-c-1)

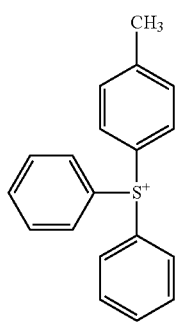
(b2-c-2)
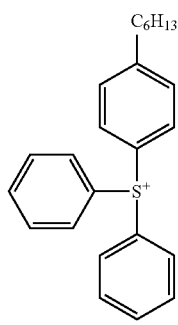
(b2-c-7)
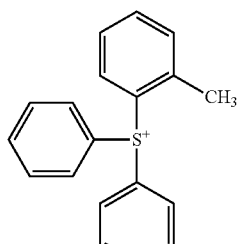
(b2-c-3)
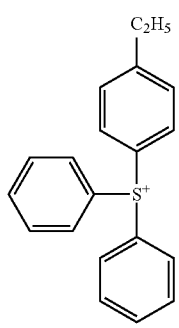
(b2-c-4)
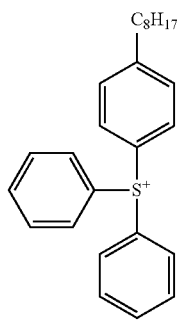
(b2-c-8)
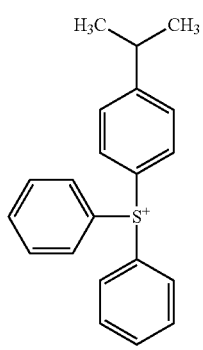
(b2-c-5)
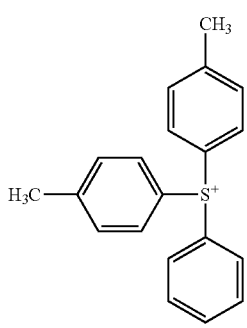
(b2-c-9)
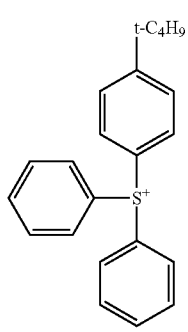
(b2-c-6)
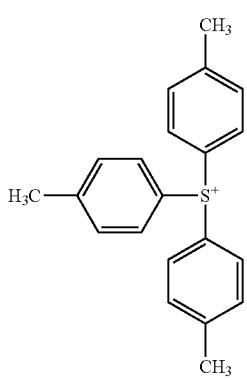
(b2-c-10)

-continued
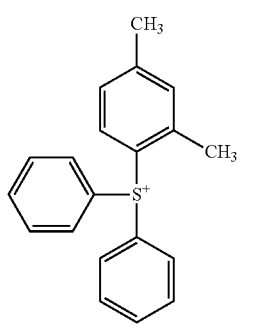
(b2-c-11)
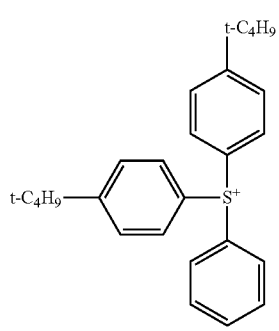
(b2-c-12)
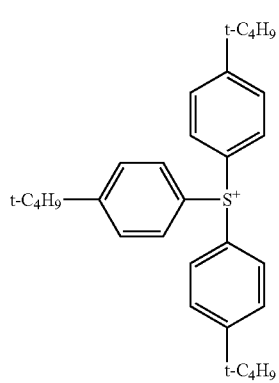
(b2-c-13)
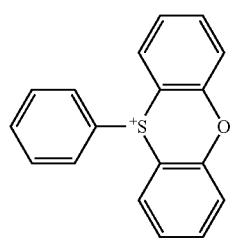
(b2-c-14)
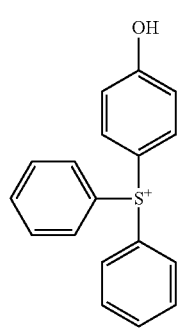
(b2-c-15)
-continued
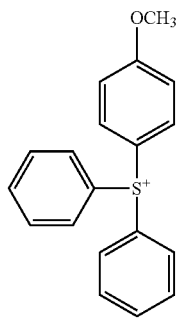
(b2-c-16)
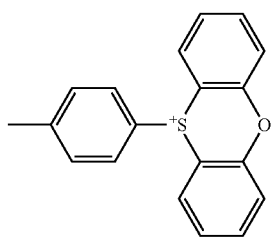
(b2-c-17)
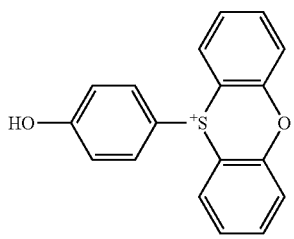
(b2-c-18)
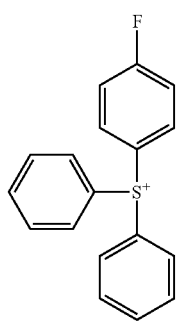
(b2-c-19)
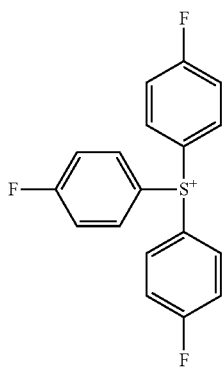
(b2-c-20)

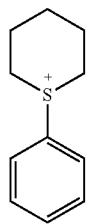 (b2-c-21)
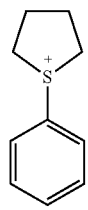 (b2-c-22)
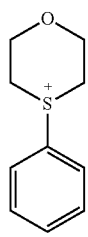 (b2-c-23)
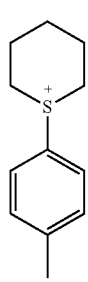 (b2-c-24)
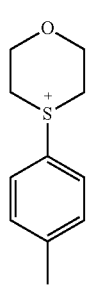 (b2-c-25)
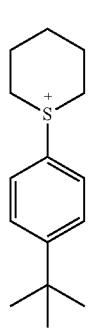 (b2-c-26)
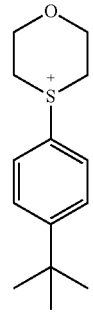 (b2-c-27)
The organic cations represented by formula (b2-2) include the following ones.
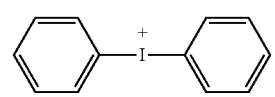 (b2-c-28)
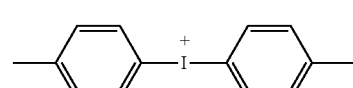 (b2-c-29)
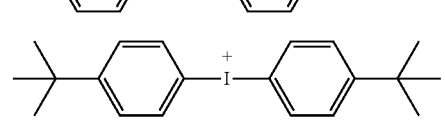 (b2-c-30)
The organic cations represented by formula (b2-3) include the following ones.
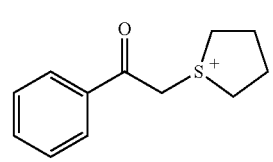 (b2-c-31)
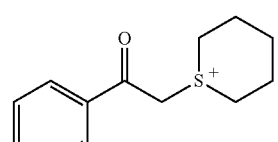 (b2-c-32)
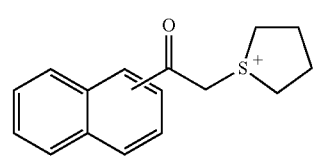 (b2-c-33)
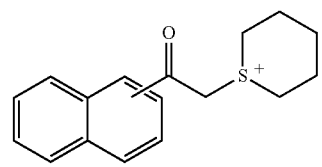 (b2-c-34)
The SALT (I) consists of any one of the sulfonic acid anions as mentioned above and any one of the organic cation as mentioned above.

Specific examples of SALT (I) include those shown in Tables 1, 2, 3 and 4. In each table, the symbols, e.g. "(Ia1-1-1)", in the columns "Sulfonic acid anion" represent the sulfonic acid anions represented by the above-mentioned formulae corresponding to the symbols, and the symbols, e.g. "(b2-c-1)", in the columns "Organic cation" represent the organic cations represented by the above-mentioned formulae corresponding to the symbols.

TABLE 1

| SALT (I) | Sulfonic acid anion | Organic cation |
| --- | --- | --- |
| (I-1) | (Ia1-1-1) | (b2-c-1) |
| (I-2) | (Ia1-1-2) | (b2-c-1) |
| (I-3) | (Ia1-1-3) | (b2-c-1) |
| (I-4) | (Ia1-1-4) | (b2-c-1) |
| (I-5) | (Ia1-1-5) | (b2-c-1) |
| (I-6) | (Ia1-1-6) | (b2-c-1) |
| (I-7) | (Ia1-1-7) | (b2-c-1) |
| (I-8) | (Ia1-1-8) | (b2-c-1) |
| (I-9) | (Ia1-1-9) | (b2-c-1) |
| (I-10) | (Ia1-1-10) | (b2-c-1) |
| (I-11) | (Ia1-1-1) | (b2-c-10) |

TABLE 2

| SALT (I) | Sulfonic acid anions | Organic cation |
| --- | --- | --- |
| (I-12) | (Ia1-1-2) | (b2-c-10) |
| (I-13) | (Ia1-1-3) | (b2-c-10) |
| (I-14) | (Ia1-1-4) | (b2-c-10) |
| (I-15) | (Ia1-1-5) | (b2-c-10) |
| (I-16) | (Ia1-1-6) | (b2-c-10) |
| (I-17) | (Ia1-1-7) | (b2-c-10) |
| (I-18) | (Ia1-1-8) | (b2-c-10) |
| (I-19) | (Ia1-1-9) | (b2-c-10) |
| (I-20) | (Ia1-1-10) | (b2-c-10) |
| (I-21) | (Ia1-1-1) | (b2-c-14) |
| (I-22) | (Ia1-1-2) | (b2-c-14) |
| (I-23) | (Ia1-1-3) | (b2-c-14) |
| (I-24) | (Ia1-1-4) | (b2-c-14) |
| (I-25) | (Ia1-1-5) | (b2-c-14) |
| (I-26) | (Ia1-1-6) | (b2-c-14) |
| (I-27) | (Ia1-1-7) | (b2-c-14) |
| (I-28) | (Ia1-1-8) | (b2-c-14) |
| (I-29) | (Ia1-1-9) | (b2-c-14) |
| (I-30) | (Ia1-1-10) | (b2-c-14) |
| (I-31) | (Ia1-1-1) | (b2-c-23) |
| (I-32) | (Ia1-1-2) | (b2-c-23) |
| (I-33) | (Ia1-1-3) | (b2-c-23) |
| (I-34) | (Ia1-1-4) | (b2-c-23) |
| (I-35) | (Ia1-1-5) | (b2-c-23) |
| (I-36) | (Ia1-1-6) | (b2-c-23) |
| (I-37) | (Ia1-1-7) | (b2-c-23) |
| (I-38) | (Ia1-1-8) | (b2-c-23) |
| (I-39) | (Ia1-1-9) | (b2-c-23) |
| (I-40) | (Ia1-1-10) | (b2-c-23) |
| (I-41) | (Ia1-1-1) | (b2-c-27) |
| (I-42) | (Ia1-1-2) | (b2-c-27) |
| (I-43) | (Ia1-1-3) | (b2-c-27) |
| (I-44) | (Ia1-1-4) | (b2-c-27) |
| (I-45) | (Ia1-1-5) | (b2-c-27) |
| (I-46) | (Ia1-1-6) | (b2-c-27) |
| (I-47) | (Ia1-1-7) | (b2-c-27) |
| (I-48) | (Ia1-1-8) | (b2-c-27) |
| (I-49) | (Ia1-1-9) | (b2-c-27) |
| (I-50) | (Ia1-1-10) | (b2-c-27) |
| (I-51) | (Ia1-1-1) | (b2-c-28) |
| (I-52) | (Ia1-1-2) | (b2-c-28) |

TABLE 3

| SALT (I) | Sulfonic acid anions | Organic cation |
| --- | --- | --- |
| (I-53) | (Ia1-1-3) | (b2-c-28) |
| (I-54) | (Ia1-1-4) | (b2-c-28) |
| (I-55) | (Ia1-1-5) | (b2-c-28) |
| (I-56) | (Ia1-1-6) | (b2-c-28) |
| (I-57) | (Ia1-1-7) | (b2-c-28) |
| (I-58) | (Ia1-1-8) | (b2-c-28) |
| (I-59) | (Ia1-1-9) | (b2-c-28) |
| (I-60) | (Ia1-1-10) | (b2-c-28) |
| (I-61) | (Ia1-1-1) | (b2-c-31) |
| (I-62) | (Ia1-1-2) | (b2-c-31) |
| (I-63) | (Ia1-1-3) | (b2-c-31) |
| (I-64) | (Ia1-1-4) | (b2-c-31) |
| (I-65) | (Ia1-1-5) | (b2-c-31) |
| (I-66) | (Ia1-1-6) | (b2-c-31) |
| (I-67) | (Ia1-1-7) | (b2-c-31) |
| (I-68) | (Ia1-1-8) | (b2-c-31) |
| (I-69) | (Ia1-1-9) | (b2-c-31) |
| (I-70) | (Ia1-1-10) | (b2-c-31) |
| (I-71) | (Ia1-1-1) | (b2-c-2) |
| (I-72) | (Ia1-1-2) | (b2-c-2) |
| (I-73) | (Ia1-1-3) | (b2-c-2) |
| (I-74) | (Ia1-1-4) | (b2-c-2) |
| (I-75) | (Ia1-1-1) | (b2-c-6) |
| (I-76) | (Ia1-1-2) | (b2-c-6) |
| (I-77) | (Ia1-1-3) | (b2-c-6) |
| (I-78) | (Ia1-1-4) | (b2-c-6) |
| (I-79) | (Ia1-1-1) | (b2-c-15) |
| (I-80) | (Ia1-1-2) | (b2-c-15) |
| (I-81) | (Ia1-1-3) | (b2-c-15) |
| (I-82) | (Ia1-1-4) | (b2-c-15) |
| (I-83) | (Ia1-1-1) | (b2-c-18) |
| (I-84) | (Ia1-1-2) | (b2-c-18) |
| (I-85) | (Ia1-1-3) | (b2-c-18) |
| (I-86) | (Ia1-1-4) | (b2-c-18) |
| (I-87) | (Ia1-1-1) | (b2-c-30) |
| (I-88) | (Ia1-1-2) | (b2-c-30) |
| (I-89) | (Ia1-1-3) | (b2-c-30) |
| (I-90) | (Ia1-1-4) | (b2-c-30) |
| (I-91) | (Ia1-1-11) | (b2-c-1) |
| (I-92) | (Ia1-1-12) | (b2-c-1) |
| (I-93) | (Ia1-1-13) | (b2-c-1) |
| (I-94) | (Ia1-1-14) | (b2-c-1) |
| (I-95) | (Ia1-1-11) | (b2-c-10) |
| (I-96) | (Ia1-1-12) | (b2-c-10) |

TABLE 4

| SALT (I) | Sulfonic acid anions | Organic cation |
| --- | --- | --- |
| (I-97) | (Ia1-1-13) | (b2-c-10) |
| (I-98) | (Ia1-1-14) | (b2-c-10) |
| (I-99) | (Ia1-1-11) | (b2-c-14) |
| (I-100) | (Ia1-1-12) | (b2-c-14) |
| (I-101) | (Ia1-1-13) | (b2-c-14) |
| (I-102) | (Ia1-1-14) | (b2-c-14) |
| (I-103) | (Ia1-1-11) | (b2-c-23) |
| (I-104) | (Ia1-1-12) | (b2-c-23) |
| (I-105) | (Ia1-1-13) | (b2-c-23) |
| (I-106) | (Ia1-1-14) | (b2-c-23) |
| (I-107) | (Ia1-1-11) | (b2-c-27) |
| (I-108) | (Ia1-1-12) | (b2-c-27) |
| (I-109) | (Ia1-1-13) | (b2-c-27) |
| (I-110) | (Ia1-1-14) | (b2-c-27) |
| (I-111) | (Ia1-1-11) | (b2-c-28) |
| (I-112) | (Ia1-1-12) | (b2-c-28) |
| (I-113) | (Ia1-1-13) | (b2-c-28) |
| (I-114) | (Ia1-1-14) | (b2-c-28) |
| (I-115) | (Ia1-1-11) | (b2-c-31) |
| (I-116) | (Ia1-1-12) | (b2-c-31) |
| (I-117) | (Ia1-1-13) | (b2-c-31) |
| (I-118) | (Ia1-1-14) | (b2-c-31) |

The SALT (I) includes preferably salts in which $Q^1$ and $Q^2$ is a fluorine atom; the moiety $L^1$-OH is represented by formula (L-1); and W is an adamantyl group in which a methylene group can be replaced by a carbonyl group and in which a hydrogen atom can be replaced by a hydroxy group, or a C1-C12 alkyl group.

In the SALT (I), the moiety $L^1$-OH is preferably represented by formula (L-1) in which $X^0$ is a single bond, C1-C4 alkylene group, or a group represented by formula (a-1) where s is 0, $A^{10}$ is an adamantane ring, $X^{11}$ is a carbonyloxy group and $A^{12}$ is C1-C4 alkylene group, $X^1$ represents —O—CO-*$^1$ or —O—CH$_2$—CO—O-*$^1$ where *$^1$ represents a binding position to W as defined above.

Examples of preferred SALT (I) include specifically the salts represented by formulae (I-1), (I-2), (I-3), (I-4), (I-11) (I-12), (I-13), (I-14), (I-21), (I-22), (I-23), (I-24), (I-31), (I-32), (I-33), (I-34), (I-41), (I-42), (I-43) (I-44), (I-51), (I-52) (I-53), (I-54), (I-61), (I-62), (I-63), (I-64), (I-91), (I-92), (I-93), (I-94), (I-95), (I-96), (I-97), (I-98), (I-99), (I-100), (I-101), (I-102), (I-103), (I-104), (I-105), (I-106), (I-107), (I-108), (I-109), (I-110) (I-111), (I-112), (I-113), (I-114), (I-115), (I-116), (I-117), and (I-118).

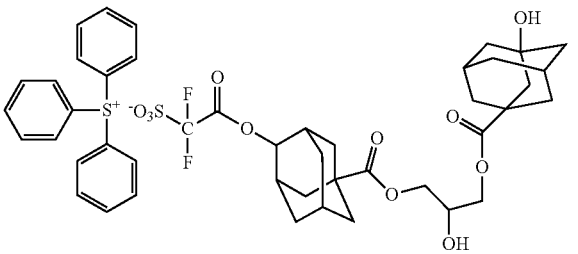

(I-3)

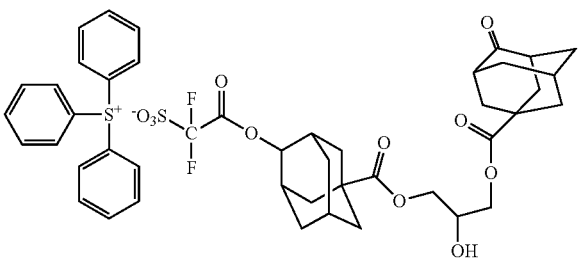

(I-4)

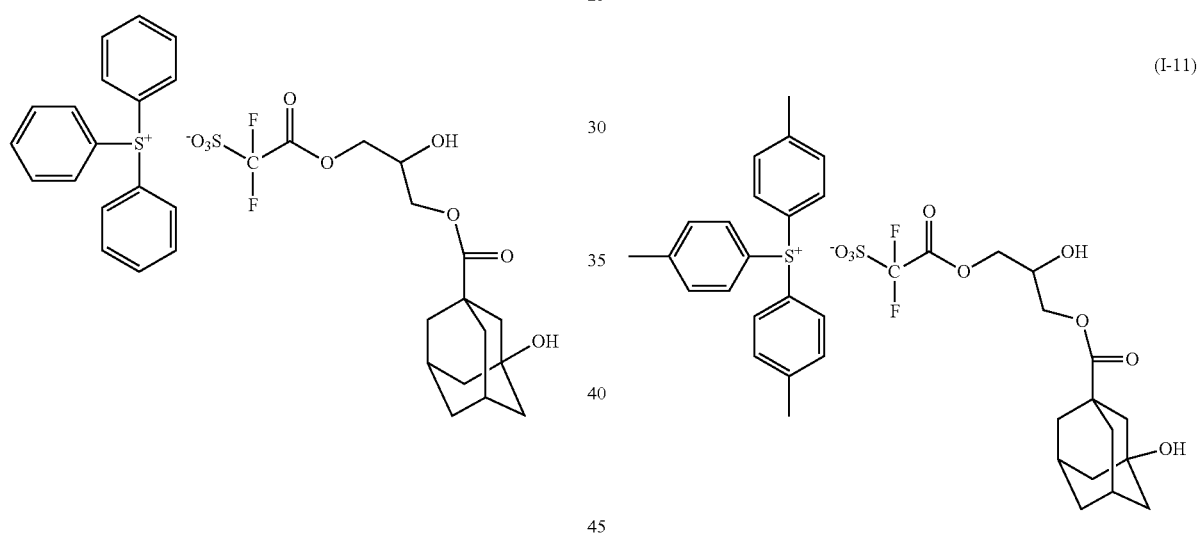

(I-1)

(I-11)

(I-2)

(I-12)

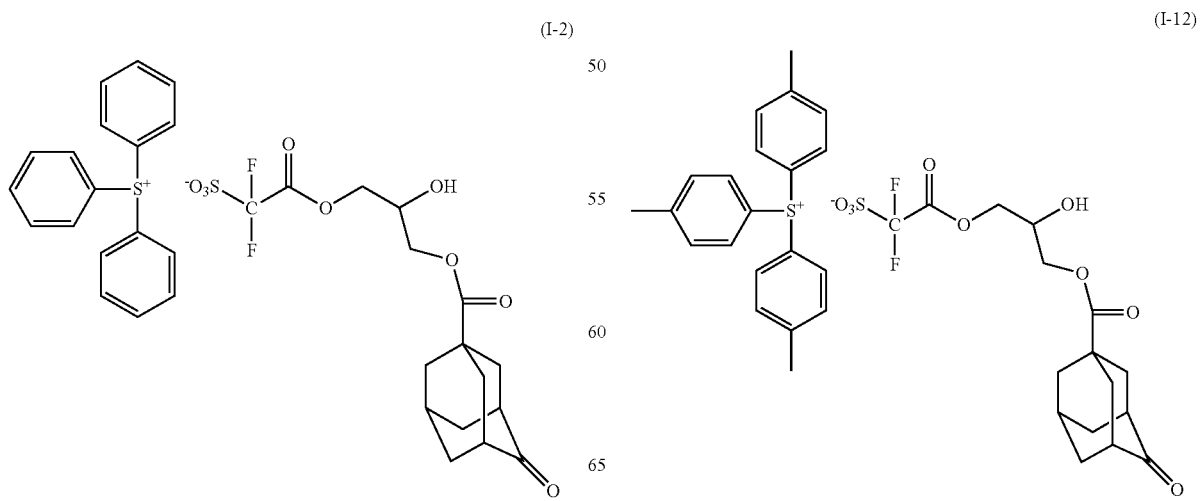

(I-13)
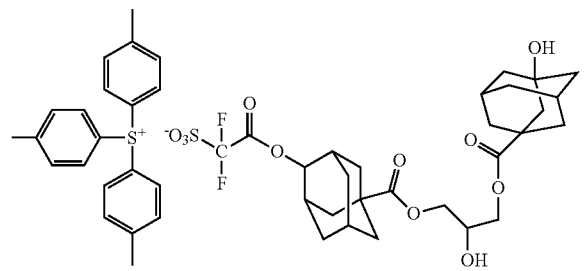
(I-14)
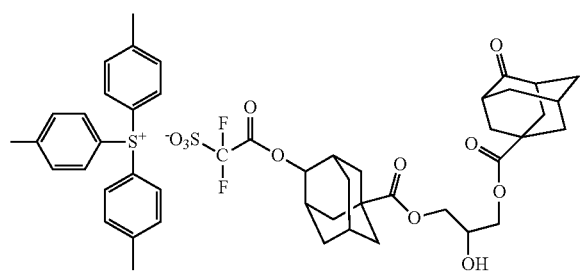
(I-91)
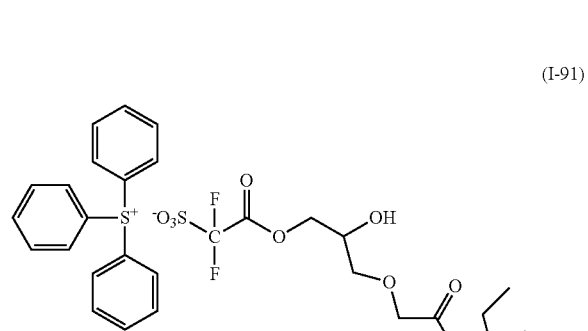
(I-92)
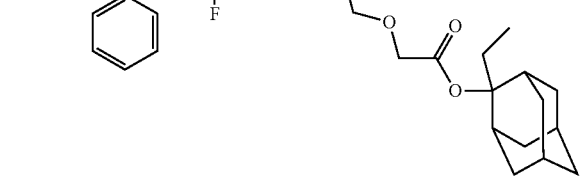
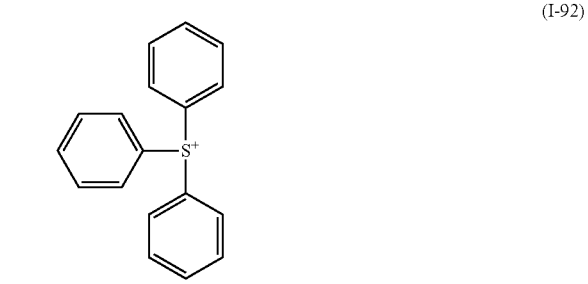
(I-93)
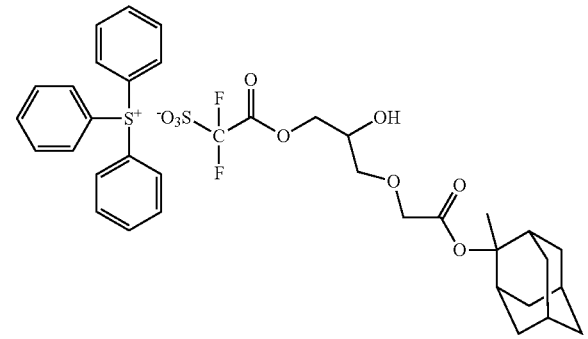
(I-94)
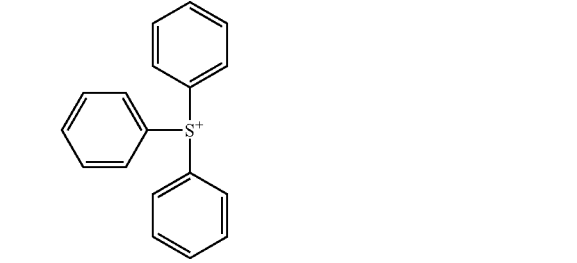
(I-95)
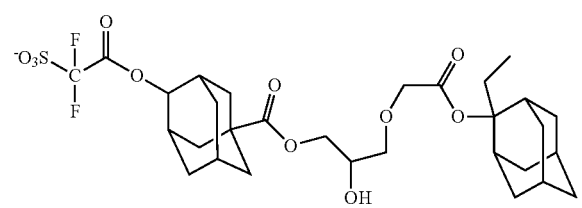
(I-96)
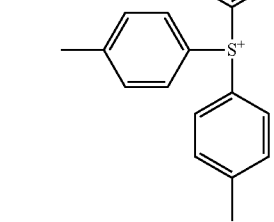

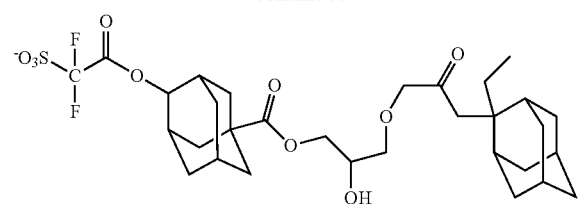
(I-97)
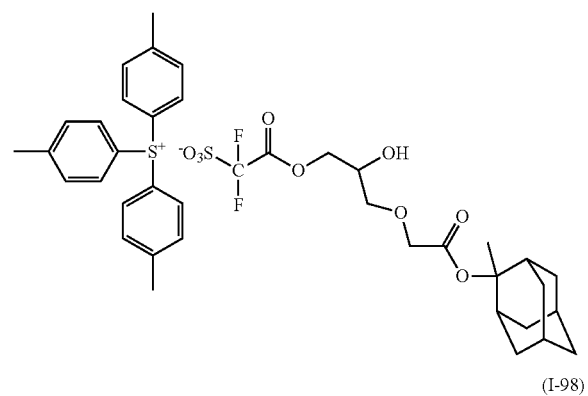
(I-98)
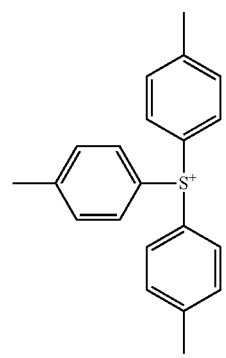
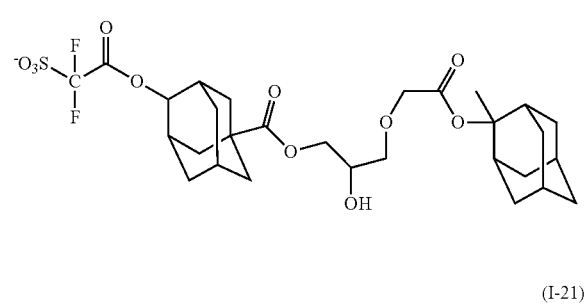
(I-21)
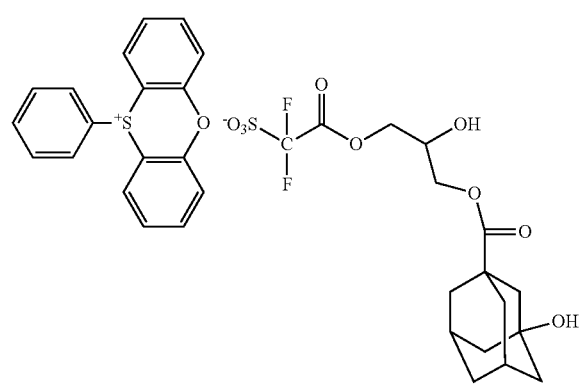
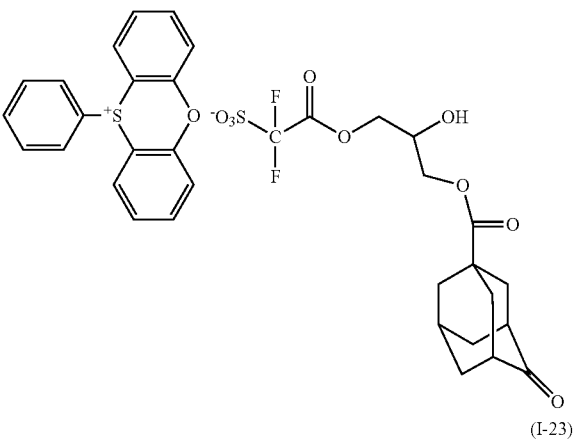
(I-22)
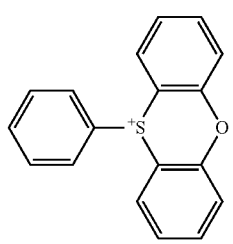
(I-23)
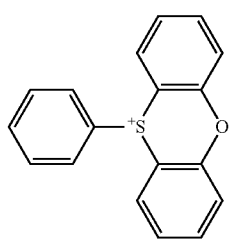
(I-24)
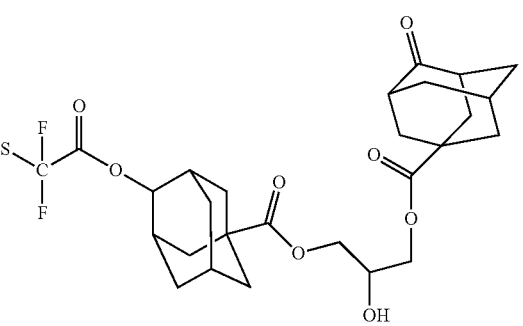

(I-31)
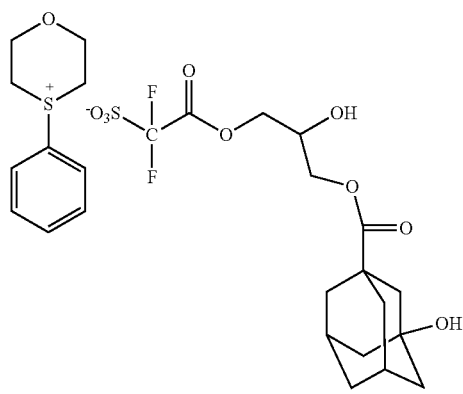
(I-32)
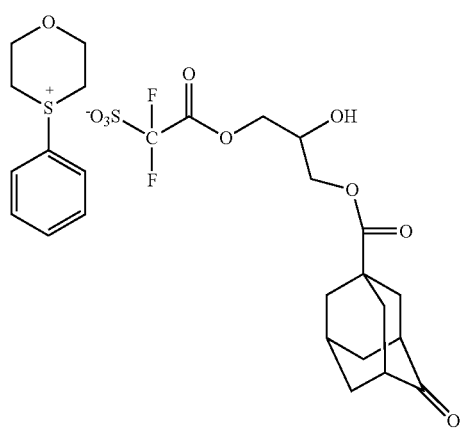
(I-33)
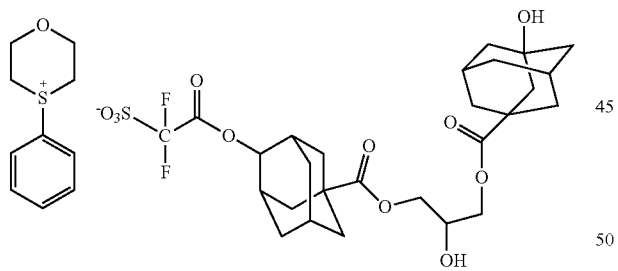
(I-34)
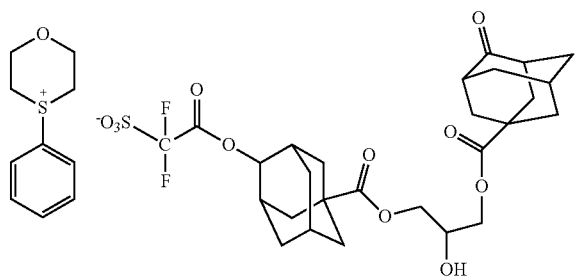
(I-99)
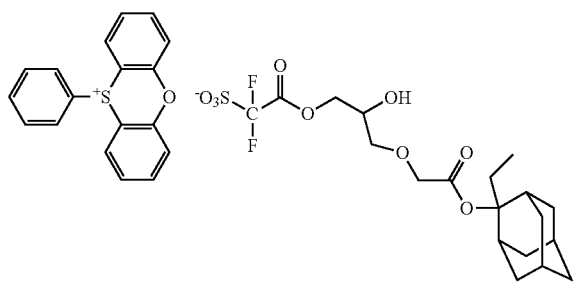
(I-100)
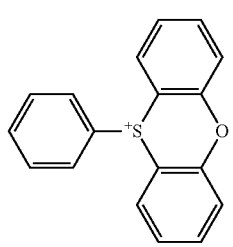
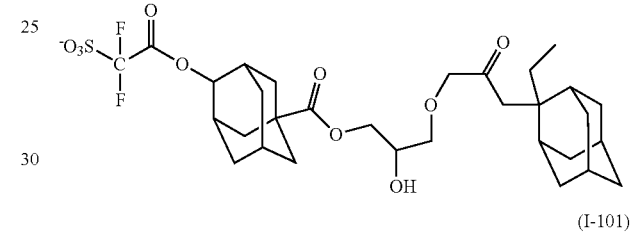
(I-101)
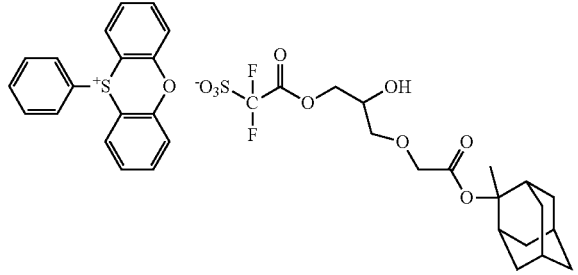
(I-102)
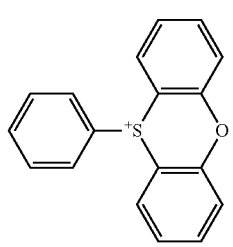
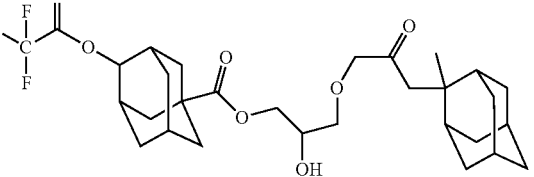

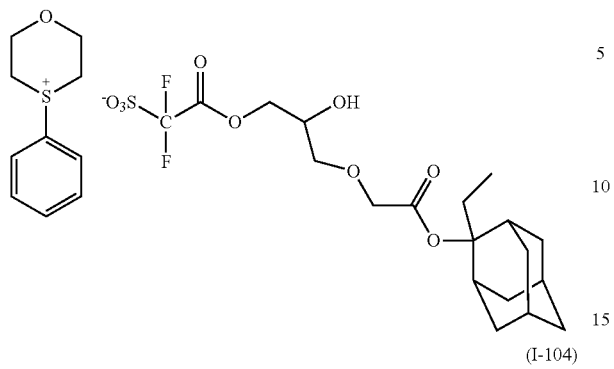
(I-103)
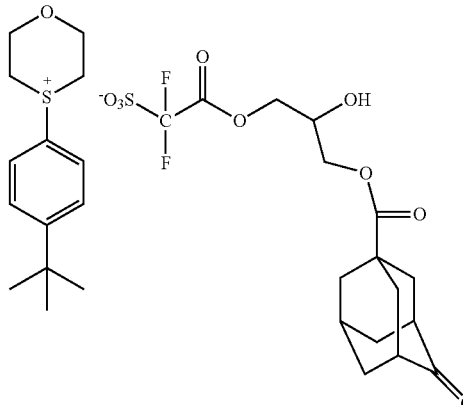
(I-42)
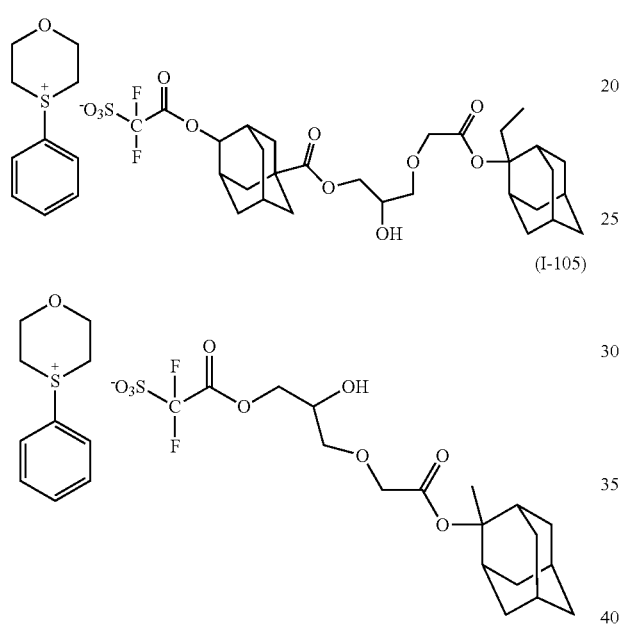
(I-104)
(I-105)
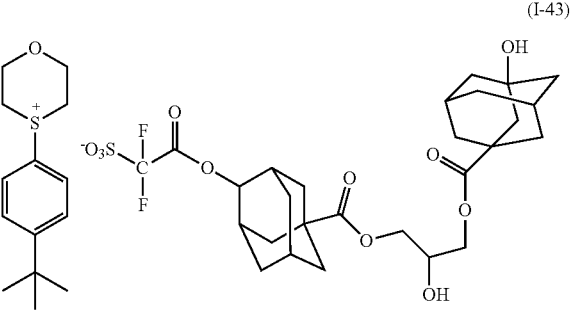
(I-43)
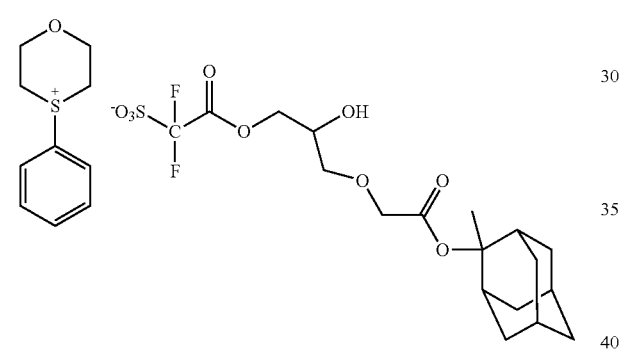
(I-106)
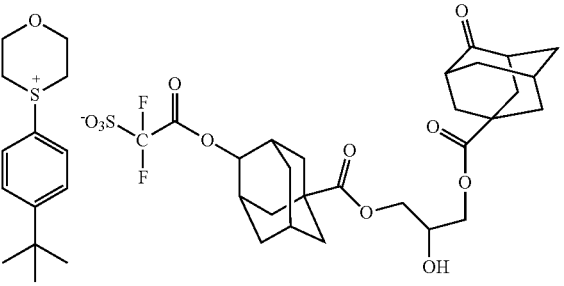
(I-44)
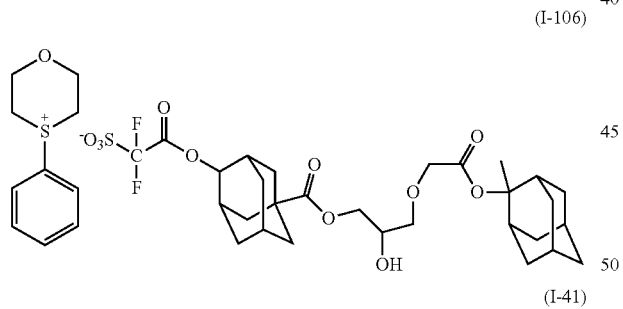
(I-41)
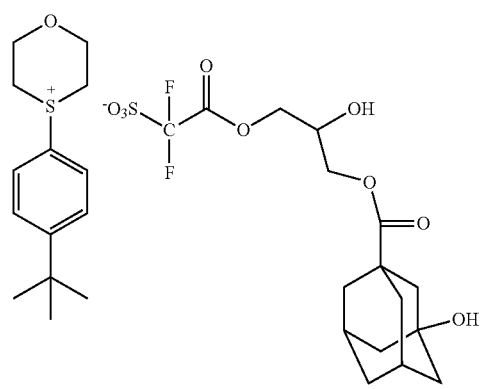
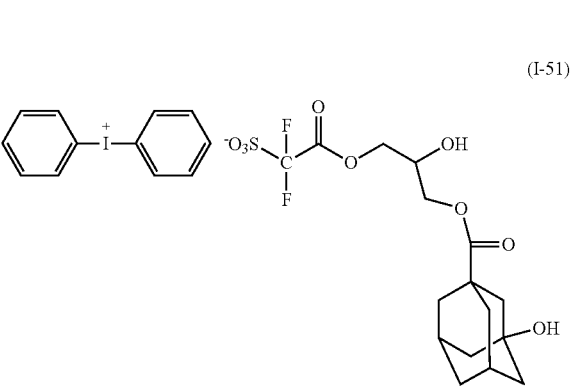
(I-51)

(I-52)
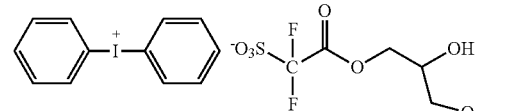
(I-109)
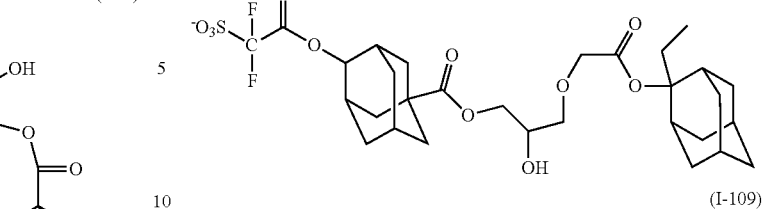
(I-53)
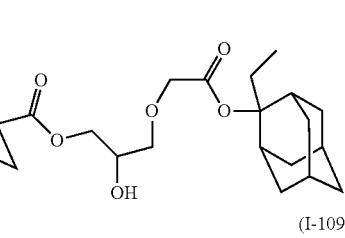
(I-110)
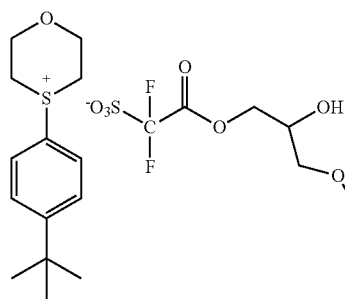
(I-54)
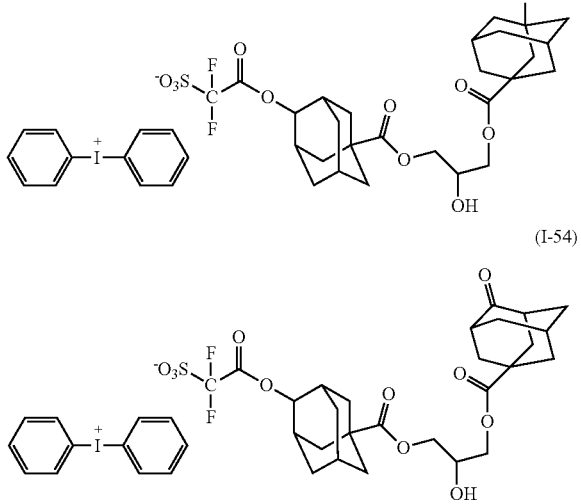
(I-111)
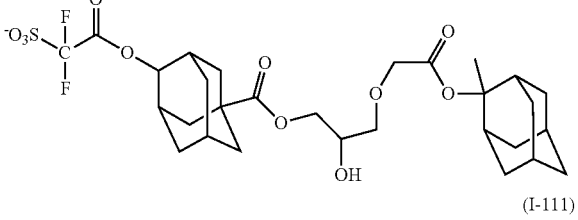
(I-107)
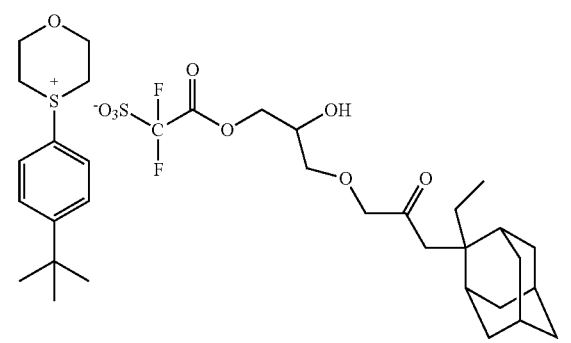
(I-112)
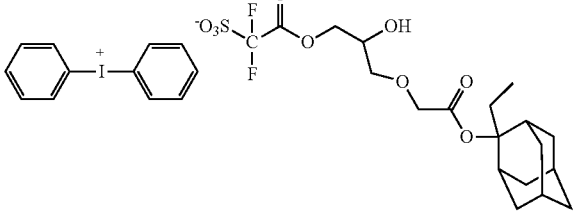
(I-108)
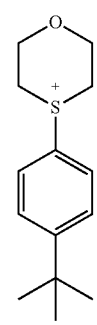

(I-113)
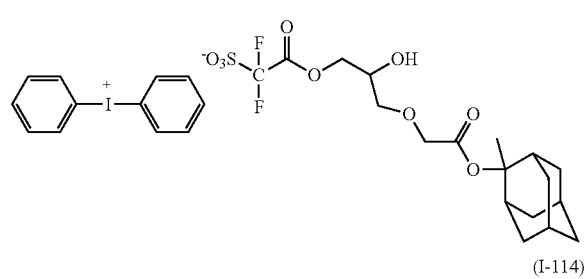
(I-114)
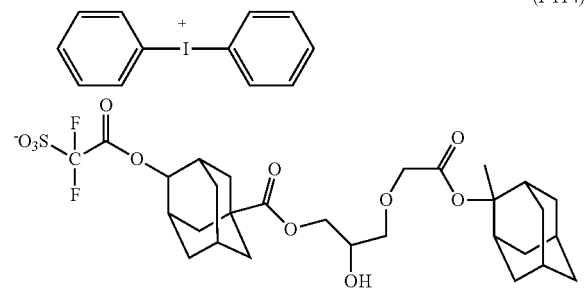
(I-61)
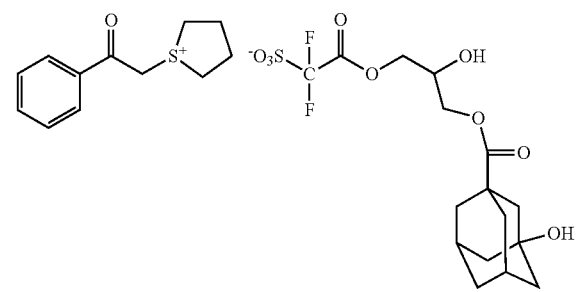
(I-62)
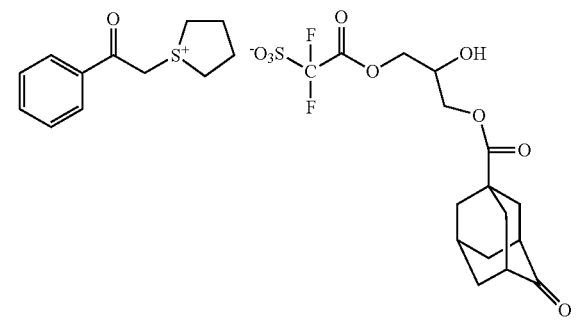
(I-63)
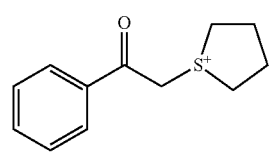
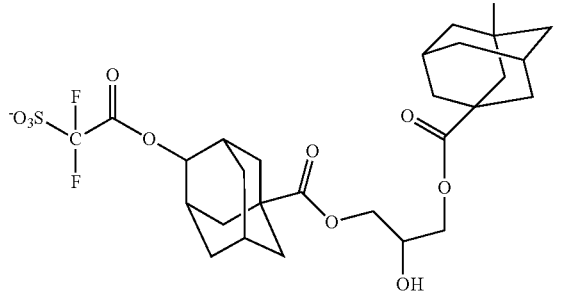
(I-64)
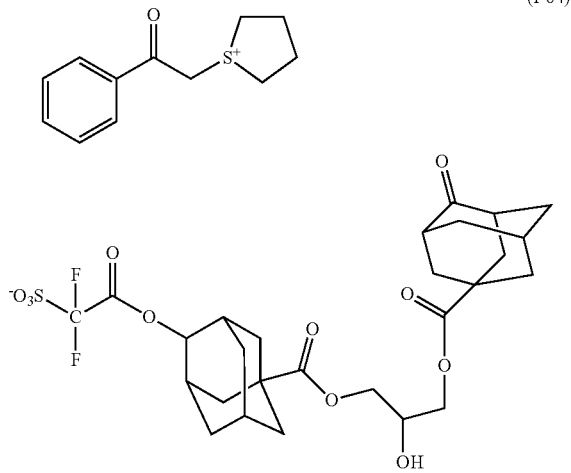
(I-115)
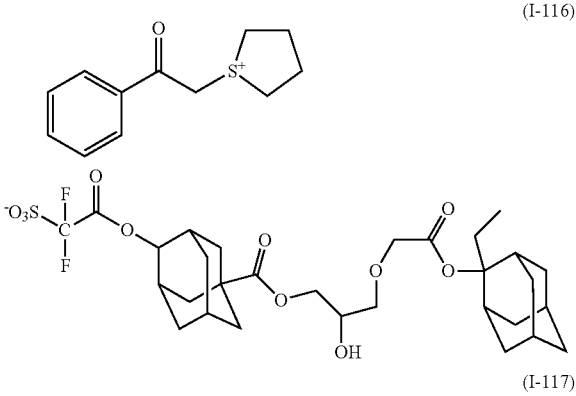
(I-116)
(I-117)
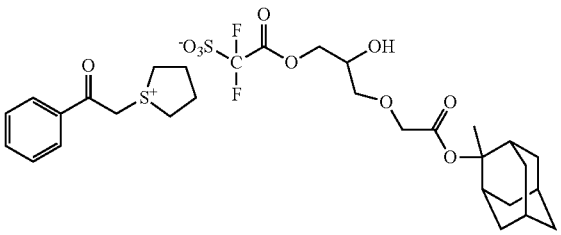

-continued

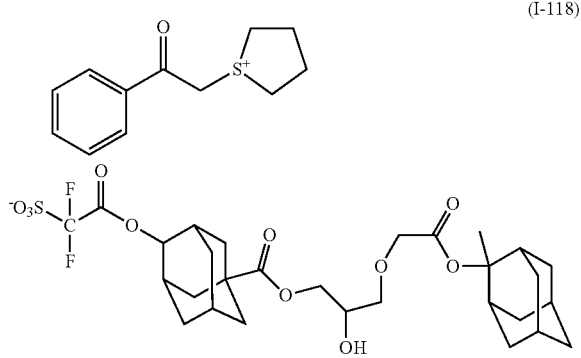
(I-118)

The process for producing SALT (I) will be illustrated,

The SALT (I) in which the moiety "$L^1$-OH" represents the following formula

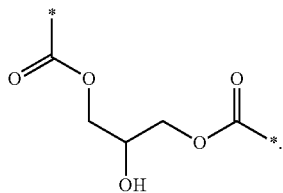

can be produced by reacting a salt represented by formula (I1-a) with a compound represented by formula (I1-b), in the presence of a catalyst such as silver oxide or silver perchloride, in a solvent such as an organic solvent, e.g., chloroform, dichloromethane, dichloroethane, methanol, dimethylformamide or acetonitrile, as shown below;

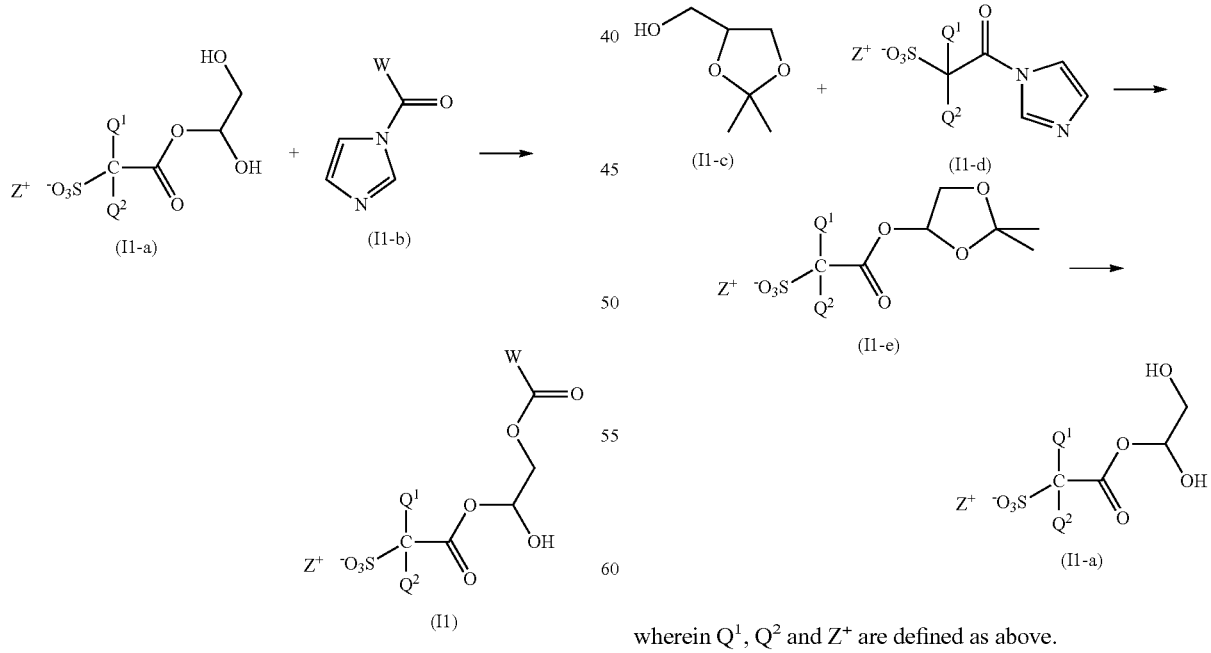

wherein $Q^1$, $Q^2$, W and $Z^+$ are defined as above, and the formula (I1) represents the SALT (I) in which the moiety $L^1$-OH is represented by the formula:

The salt represented by formula (I1-b) includes the following ones, which can be prepared by reacting the compound represented by W—COOH, where W is as defined above, with 1,1'-carbodiimidazole in an organic solvent such as chloroform.

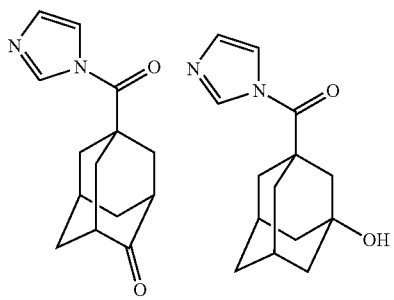

The salt represented by formula (I1-a) can be produced by reacting 3,3-dimethyl-2,4-dioxacyclopentylmethanol with a salt represented by formula (I1-d) in a solvent such as an organic solvent, e.g., chloroform, followed by treating the compound represented by formula (I1-e) with an acid, e.g. oxalic acid, as shown below;

wherein $Q^1$, $Q^2$ and $Z^+$ are defined as above.

The salt represented by formula (I1-d) can be produced by reacting a salt represented by formula (I1-f) with 1,1'-carbonyldiimidazole in a solvent such as an organic solvent, e.g., chloroform, as shown below;

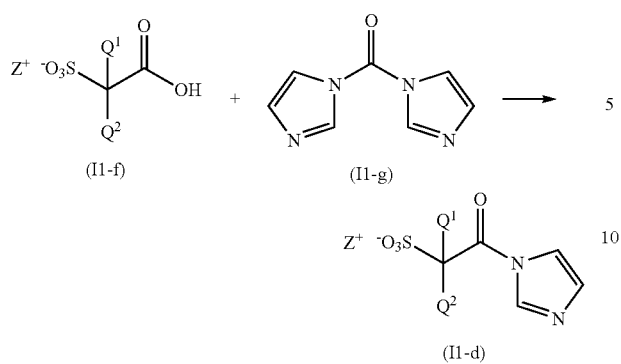

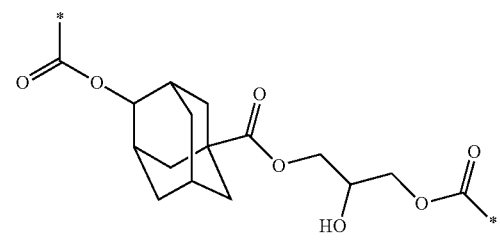

wherein $Q^1$, $Q^2$ and $Z^+$ are defined as above.

The salt represented by formula (I1-f) can be produced by a method described in JP2008-127367.

The SALT (I) wherein the moiety "$L^1$-OH" of formula (I) represents the following formula

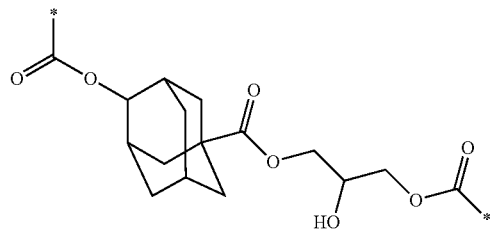 [SMILES: *C(=O)OCC(O)COC(=O)C12CC3CC(C1)C(OC(*)=O)C(C3)C2]

can be produced by reacting a salt represented by formula (I2-a) with a compound represented by formula (I1-b), in the presence of a catalyst such as silver oxide or silver perchloride, in a solvent such as an organic solvent, e.g., chloroform, dichloromethane, dichloroethane, methanol, dimethylformamide or acetonitrile, as shown below;

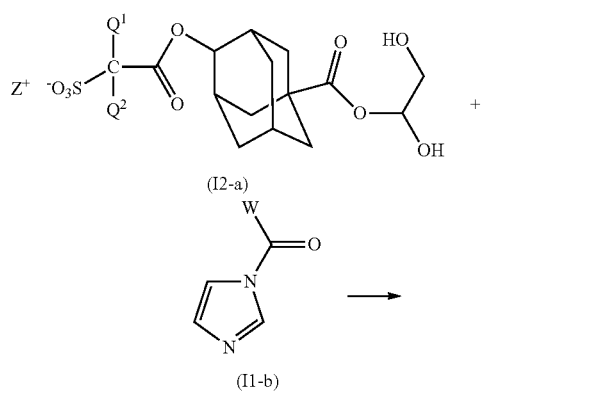

wherein $Q^1$, $Q^2$, W and $Z^+$ are defined as above, and the formula (I2) represents the SALT (I) in which the moiety $L^1$-OH is represented by the formula;

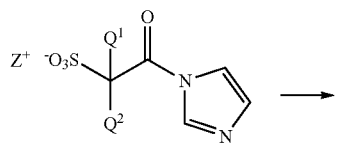

The salt represented by formula (I2-a) can be produced by reacting a compound represented by formula (I2-c) with a salt represented by formula (I1-d) in a solvent such as an organic solvent, e.g., chloroform, followed by treating the compound represented by formula (I2-e) with an acid, e.g. oxalic acid, as shown below;

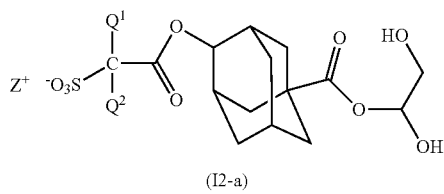

wherein $Q^1$, $Q^2$, W and $Z^+$ are defined as above.

The compound represented by formula (I2-c) can be produced by reacting a compound represented by formula (I2-f) in the presence of a reducing agent such as sodium borohydrate in a solvent such as an organic solvent, e.g., acetonitrile, as shown below;

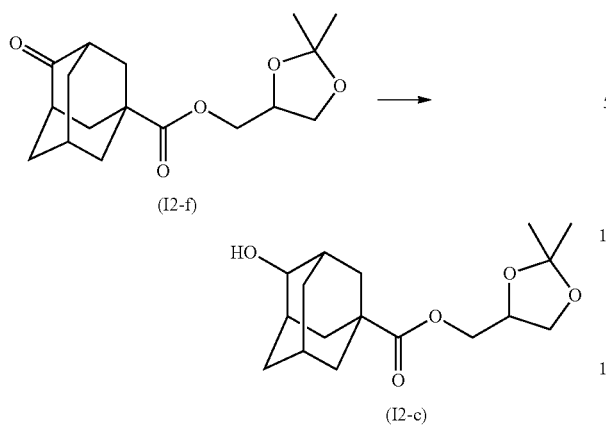

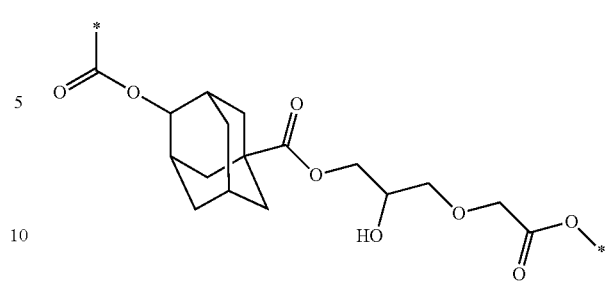

can be produced by reacting a salt represented by formula (I2-a) with a compound represented by formula (I3-a), in the presence of a base such as pyridine, in a solvent such as an organic solvent, e.g., chloroform or acetonitrile, as shown below;

The compound represented by formula (I2-f) can be produced by reacting a compound represented by formula (I2-g) with 1,1'-carbonyldiimidazole in a solvent such as an organic solvent, e.g., chloroform, followed by reacting the obtained a compound represented by formula (I2-i) with 3,3-dimethyl-2,4-dioxacyclopentylmethanol in a solvent such as an organic solvent, e.g., chloroform, shown as follows.

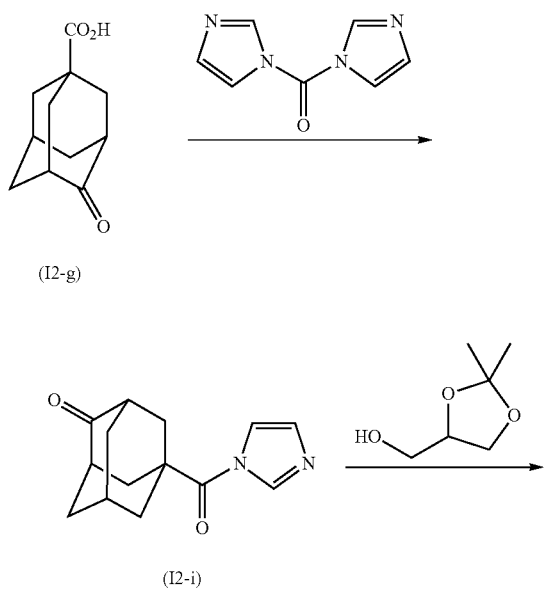

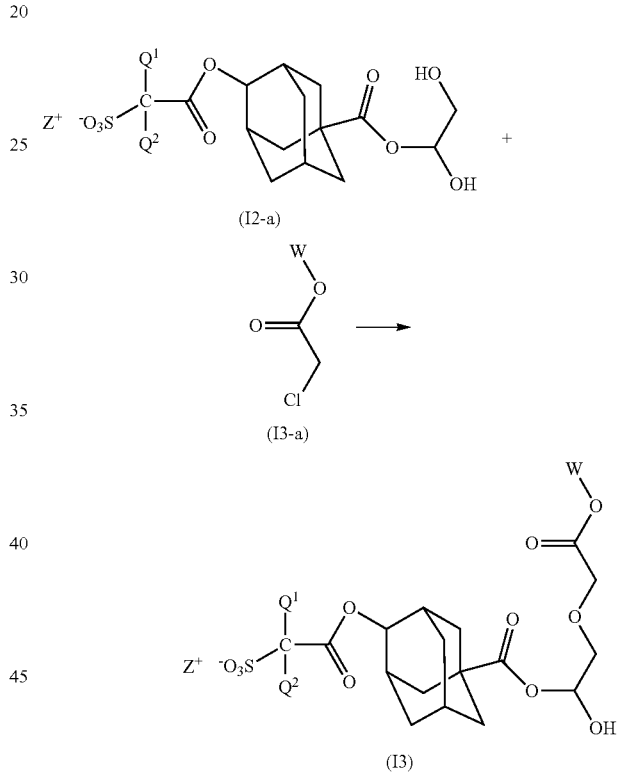

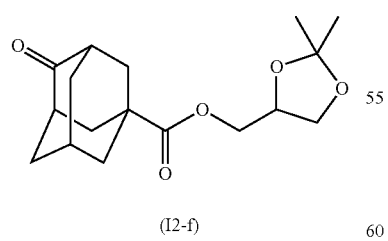

wherein $Q^1$, $Q^2$, W and $Z^+$ are defined as above, and the formula (I3) represents the SALT (I) in which the moiety $L^1$-OH is represented by the formula:

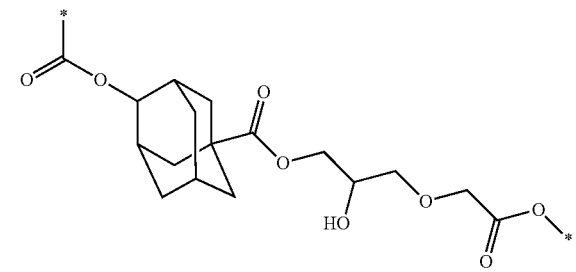 [SMILES: *OC(=O)COCC(O)COC(=O)C12CC3CC(C1)C(OC(*)=O)C(C3)C2]

The compound represented by formula (I2-g) is available on the market.

The SALT (I) wherein the moiety "$L^1$-OH" of formula (I) represents the following formula, hereinafter such salt is referred to as the salt (I3)

The compound represented by formula (I3-a) includes the following ones, which are available on the market.

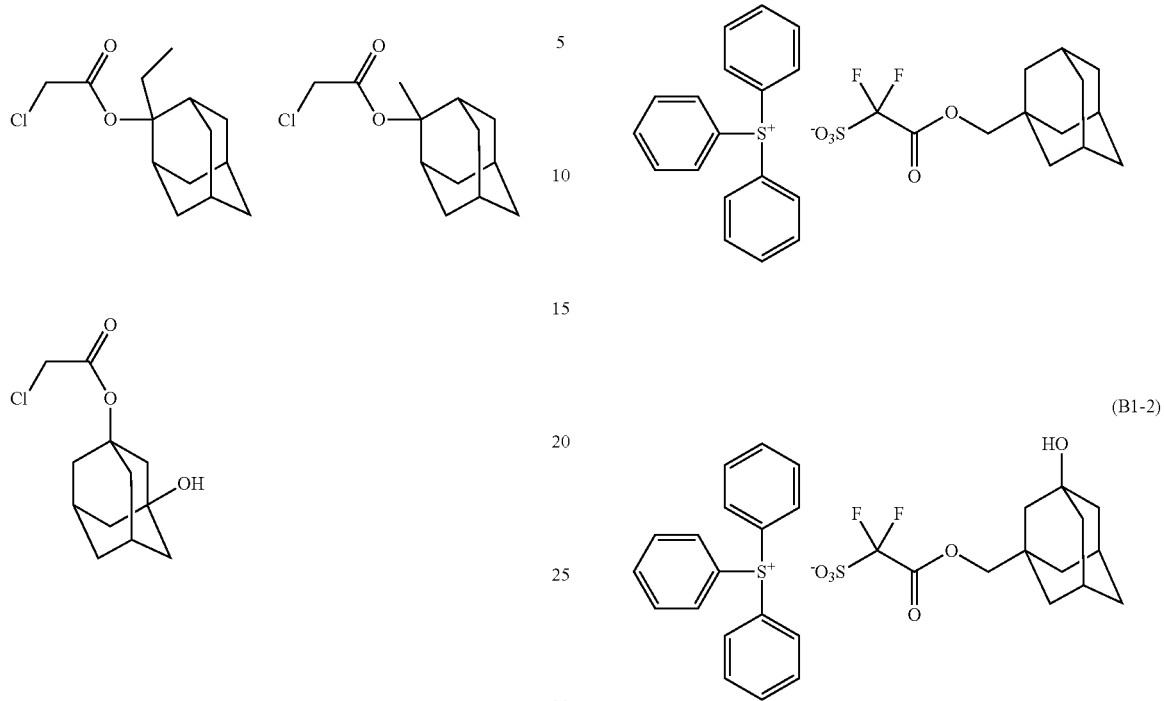

The SALT (I) in which the moiety "L¹-OH" is represented by the formula (L¹-1) can be produced by the same methods described above.

Hereinafter, the photoresist composition of the present invention will be illustrated.

The photoresist composition comprises SALT (I) and a resin which is hardly soluble or insoluble but soluble in an aqueous alkali solution by action of an acid.

The SALT (I) works as an acid generator in the photoresist composition. The photoresist composition of the present invention may comprise other acid generators than the SALT (I). The photoresist composition may comprise, if necessary, a basic compound which is a quencher known in the art, and a solvent.

The other acid generators than the SALT (I) include known acid generators. The other acid generators than SALT (I) may be either ionic or non-ionic one The other acid generators than SALT (I) may be a salt comprising different cation and anion from those of SALT (I), or a salt comprising the same cation as SALT (I) and a different known anion from that of SALT (I).

The other acid generators than the SALT (I) include those represented by formula (B1-1), formula (B1-2), formula (B1-3), formula (B1-4), formula (B1-5), formula (B1-6), formula (B1-7), formula (B1-8), formula (B1-9), formula (B1-10), formula (B1-11), formula (B1-12), formula (B1-13), formula (31-14), formula (B1-15), formula (B1-16), formula (B1-17), formula (B1-18), formula (B1-19) and formula (B1-20). Among them, preferred are compounds having triphenylsulfonium cation and compounds having tritolylsulfonium cation, and more preferred are compounds represented by formula (B1-1), formula (B1-2), formula (B1-3), formula (B1-6), formula (B1-7), formula (B1-11), formula (B1-12), formula (B1-13) and formula (B1-14).

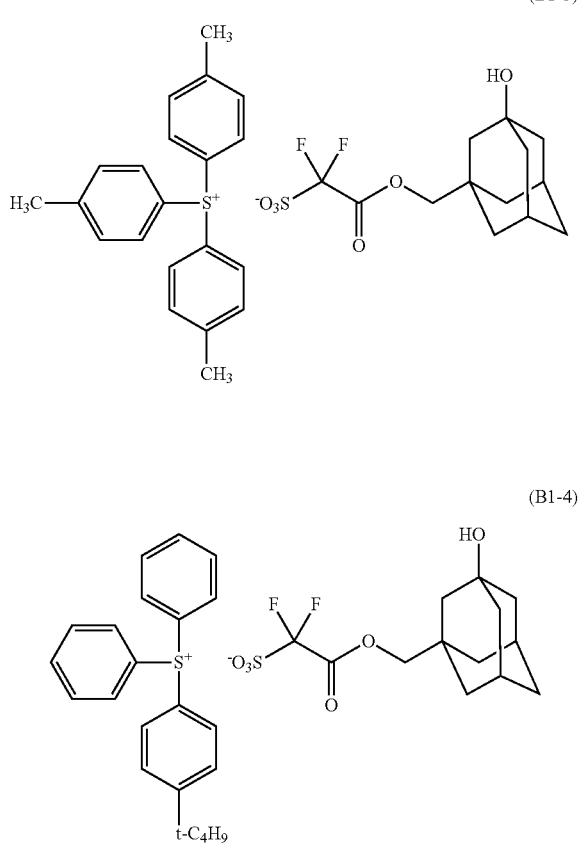

-continued
(B1-5)
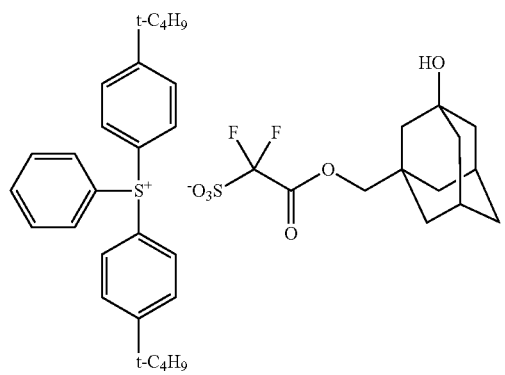
(B1-6)
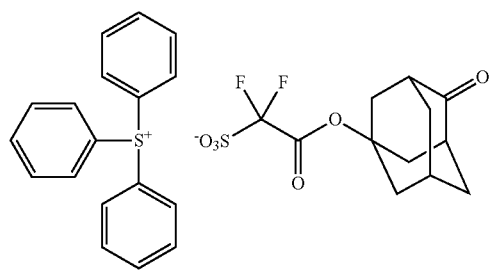
(B1-7)
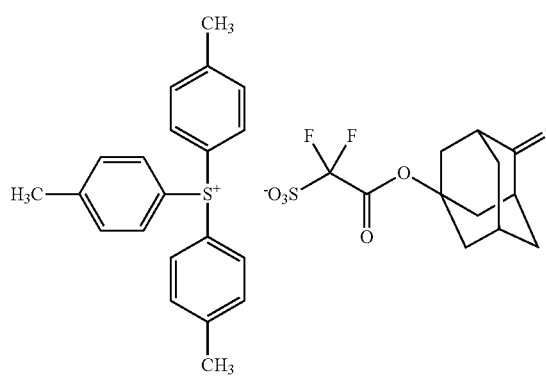
(B1-8)
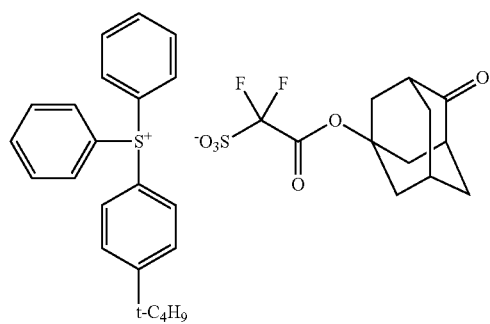
-continued
(B1-9)
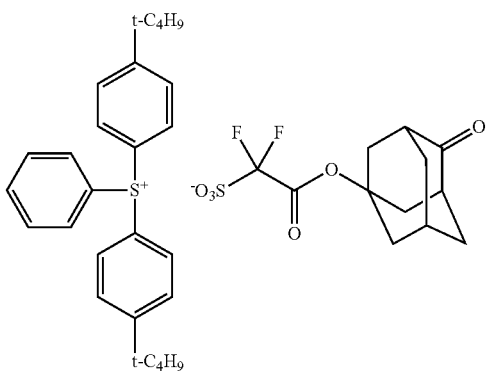
(B1-10)
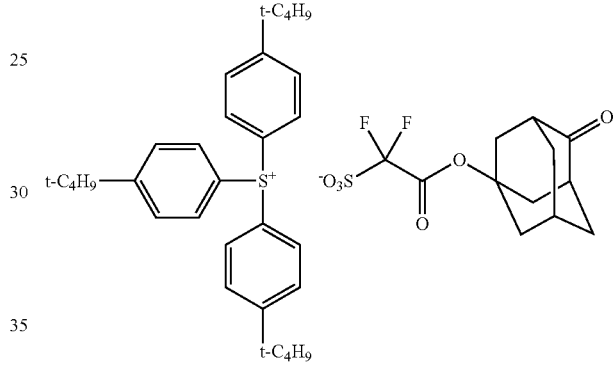
(B1-11)
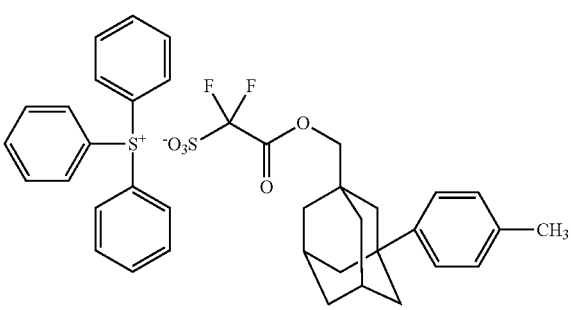
(B1-12)
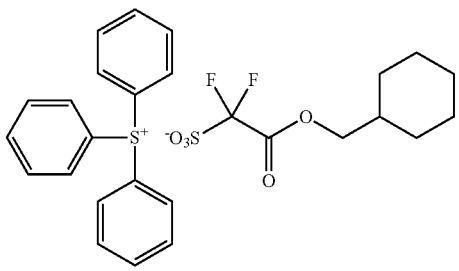

(B1-13)
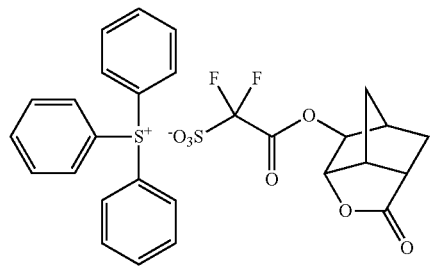

(B1-14)
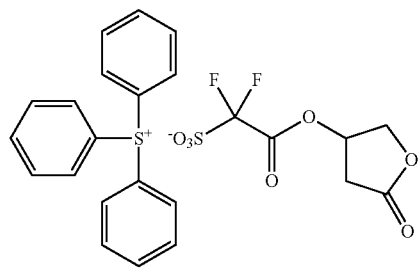

(B1-15)
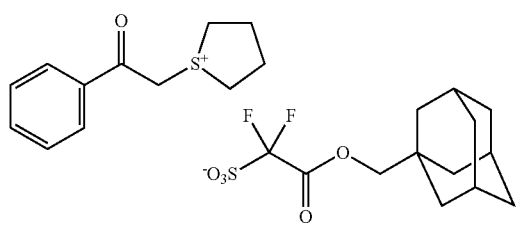

(B1-16)
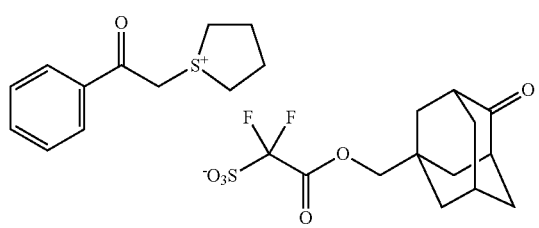

(B1-17)
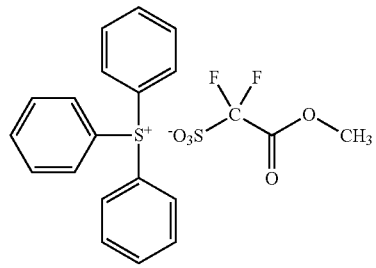

(B1-18)
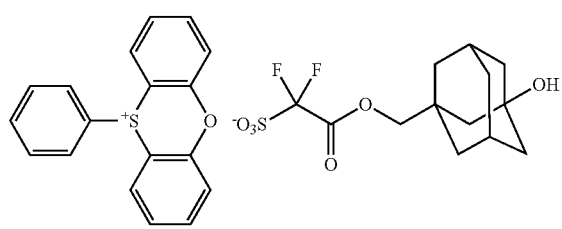

(B1-19)
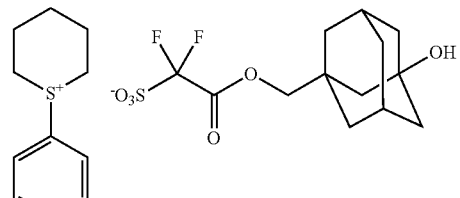

(B1-20)
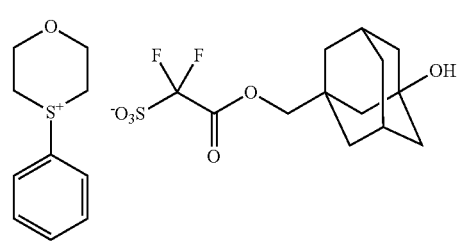

The resin for the photoresist composition of the present invention is hardly soluble or insoluble but soluble in an aqueous alkali solution by action of an acid. With such resin as having the above-mentioned properties, the photoresist composition can give a photoresist pattern by an acid generated from the acid generator as mentioned above.

Herein, "soluble in an aqueous alkali solution by the action of an acid" means such property as soluble in an aqueous alkali solution by contacting it with into an acid while hardly soluble or insoluble in an aqueous alkali solution before contacting it with into an acid.

The resin for the photoresist composition of the present invention has an acid-labile group. Such resin can be produced by polymerizing one or more kinds of monomers having an acid-labile group. Hereinafter, the resin having an acid-labile group is sometimes referred to as "rein (A)".

Herein "an acid-labile group" refers to a group capable of being cleaved in case of contacting with an acid to give a hydrophilic group such as a hydroxy group or carboxy group.

Specific examples of the acid-labile group include a group represented by the formula (1):

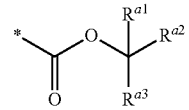
(1)

wherein $R^{a1}$, $R^{a2}$ and $R^{a3}$ independently each represent a C1-C8 alkyl group or a C3-C20 alicyclic hydrocarbon group, and $R^{a1}$ and $R^{a2}$ may be bonded each other to form a C2-C20 divalent hydrocarbon group, and * represents a binding position, and a group represented by the formula (2)

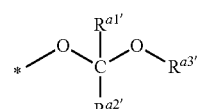
(2)

wherein $R^{a1'}$ and $R^{a2'}$ independently each represent a hydrogen atom or a C1-C12 monovalent hydrocarbon group, and $R^{a3'}$ represents a C1-C20 monovalent hydrocarbon group, or $R^{a3'}$ binds to $R^{a2'}$ together with —CO— attaching to $R^{a2'}$ and $R^{a3'}$ to form C3-C20 ring in which a methylene group of the divalent hydrocarbon group can be replaced by —O— or —S—.

Specific examples of the C1-C8 alkyl group include a methyl group, an ethyl group, a propyl group, an isopropyl group, a butyl group, a pentyl group, a hexyl group, a heptyl group and an octyl group.

The alicyclic hydrocarbon group may be monocyclic or polycyclic. Examples of the alicyclic hydrocarbon group include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the following.

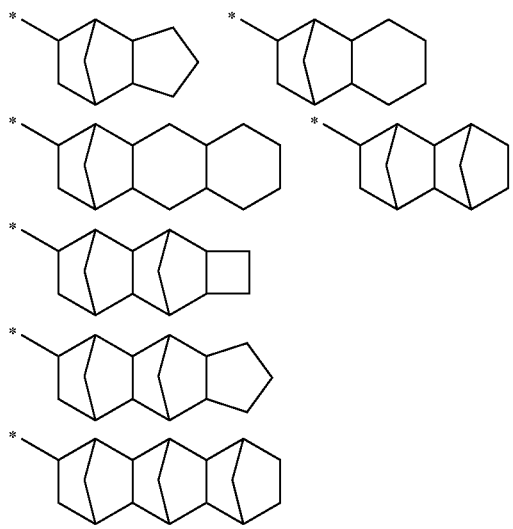

The alicyclic hydrocarbon group preferably has 5 to 16 carbon atoms.

When $R^{a1}$ and $R^{a2}$ of formula (1) are bonded each other to form a C2-C20 divalent hydrocarbon group, the moiety represented by —C($R^{a1}$) ($R^{a2}$) ($R^{a3}$) includes the following groups and the ring preferably has 3 to 12 carbon atoms:

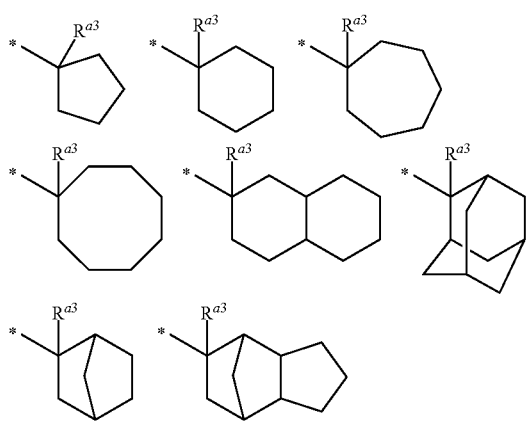

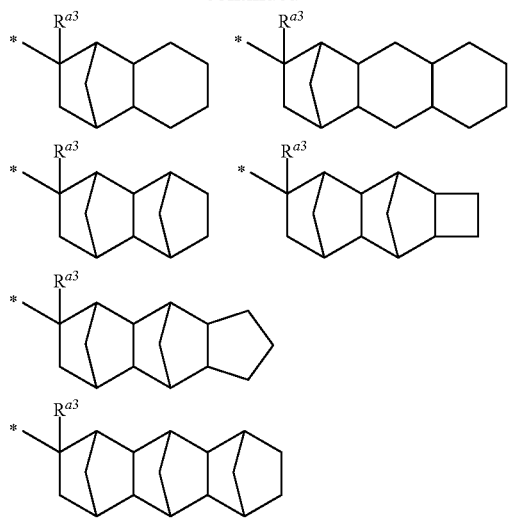

wherein $R^{a3}$ is the same as defined above and * represents a binding position to —O— of formula (1).

The group represented by the formula (1) wherein $R^{a1}$, $R^{a2}$ and $R^{a3}$ independently each represent a C1-C8 alkyl group, preferably a tert-butyl group, such as 1,1'-dialkylalkoxylcarbonyl group, the group represented by the formula (1) wherein $R^{a1}$ and $R^{a2}$ are bonded each other to form an adamantyl ring and $R^{a1}$ is a C1-C8 alkyl group such as a 2-alkyladaman-2-tyloxycarbonyl group, and the group represented by the formula (1) wherein $R^{a1}$ and $R^{a2}$ are C1-C8 alkyl groups and $R^{a1}$ is an adamantin-1-yl group such as a 1-(1-adaman-1-yl)-1-alkylalkoxycarbonyl group are preferable.

As to formula (2), examples of the hydrocarbon group include an alkyl group, an alicyclic hydrocarbon group and an aromatic hydrocarbon group.

Examples of the alkyl group and the alicyclic hydrocarbon group include the same as described above. Examples of the aromatic hydrocarbon group include an aryl group such as a phenyl group, a naphthyl group, a p-methylphenyl group, a p-tert-butylphenyl group, a p-adamantylphenyl group, a tolyl group, a xylyl group, a cumyl group, a mesityl group, a biphenyl group, an anthryl group, a phenanthryl group, a 2,6-diethylphenyl group and a 2-methyl-6-ethylphenyl group.

It is preferred that at least one of $R^{a1'}$ and $R^{2'}$ is a hydrogen atom.

Examples of the group represented by formula (2) include the following.

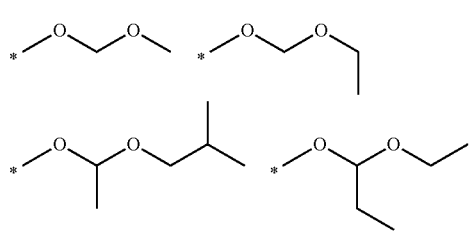

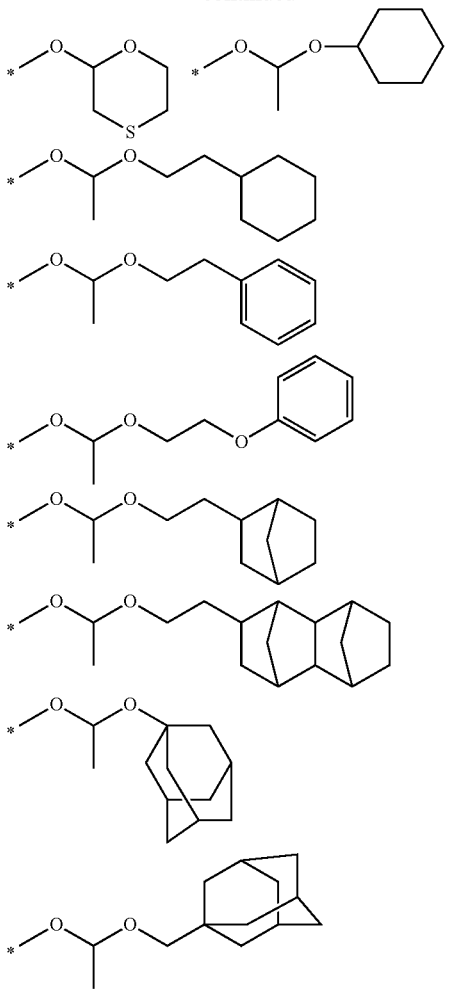

The monomer having an acid-labile group, preferably one represented by formula (1) and/or formula (2) is preferably a monomer having an acid-labile group and carbon-carbon double bond, more preferably a (meth)acrylate compound having an acid-labile group.

Such (meth)acrylate compound preferably has a C5-C20 alicyclic hydrocarbon group. Since the resin produced from (meth)acrylate compound having C5-C20 alicyclic hydrocarbon group has a bulky structure, the photoresist composition comprising the resin can show more excellent resolution.

Preferable resin (A) has a structural unit represented by the formula (a1-1) or (a1-2);

(a1-1)

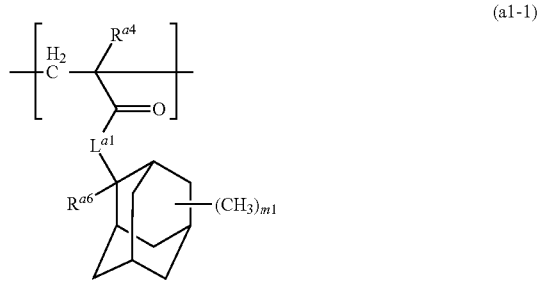

(a1-2)

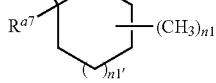

wherein $R^{a4}$ and $R^{a5}$ each independently represents a hydrogen atom or a methyl group, $R^{a6}$ and $R^{a7}$ each independently represents a C1-C10 aliphatic hydrocarbon group, $L^{a1}$ and $L^{a2}$ each independently represents *-O— or *-O—$(CH_2)_{k1}$—CO—O— in which * represents a binding position to —CO—, and k1 represents an integer of 1 to 7, $m^1$ represents an integer of 0 to 14, n1 represents an integer of 0 to 14, preferably an integer of 0 to 10, and n1' represents an integer of 0 to 3.

Examples of the aliphatic hydrocarbon group include a C1-C10 alkyl group such as a methyl group, an ethyl group, a propyl group, an isopropyl group, a butyl group, a tert-butyl group, 2,2-dimethylethyl group, 1-methylpropyl group, 2,2-dimethylpropyl group, 1-ethylpropyl group, 1-methylbutyl group, 2-methylbutyl group, 3-methylbutyl group, 1-propylbutyl group, a pentyl group, 1-methylpentyl group, a hexyl group, 1,4-dimethylhexyl group, a heptyl group, 1-methylheptyl group and an octyl group; and the saturated cyclic hydrocarbon group such as a cyclohexyl group, a methylcyclohexyl group, a dimethylcyolohexyl group, a cycloheptyl group, a methylcycloheptyl group, a norbornyl group and a methylnorbornyl group.

The alkyl group has preferably 1 to 8 carbon atoms, more preferably 1 to 6 carbon atoms, and the saturated cyclic hydrocarbon group preferably has 3 to 10 carbon atoms and more preferably 3 to 6 carbon atoms.

$L^{a1}$ and $L^{a2}$ are preferably *-O— or *-O—$(CH_2)_{f1}$—CO—O— in which * represents a binding position to —CO—, and f1 represents an integer of 1 to 4, and is more preferably *-O— or *-O—$CH_2$—CO—O—, and is especially preferably *-O—.

In the formula (a1-1), m1 is preferably an integer of 0 to 3, and is more preferably 0 or 1. In the formula (a1-2), n1 is preferably an integer of 0 to 3, and is more preferably 0 or 1. The n1' is preferably 0 or 1.

$R^{a4}$ and $R^{a5}$ are preferably methyl groups.

The compound from which the structural unit represented by (a1-1) is derived includes the compounds mentioned in JP2010-204646

As the structural unit represented by the formula (a1-1), preferred are structural units represented by formulae (a1-1-1), (a1-1-2), (a1-1-3), (a1-1-4), (a1-1-5), (a1-1-6), (a1-1-7) and (a1-1-8), more preferred are structural units represented by formulae (a1-1-1), (a1-1-2), (a1-1-3) and (a1-1-4).

(a1-1-1) 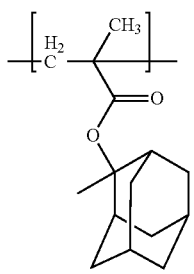
(a1-1-2) 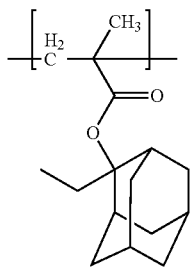
(a1-1-3) 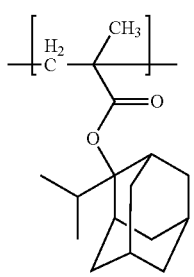
(a1-1-4) 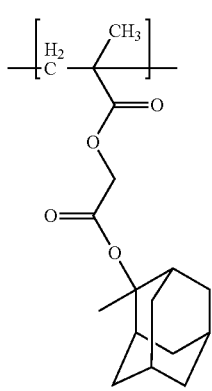
(a1-1-5) 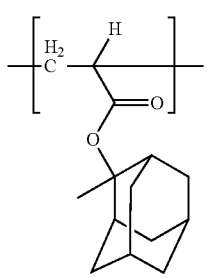
(a1-1-6) 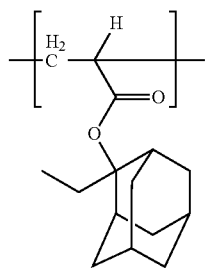
(a1-1-7) 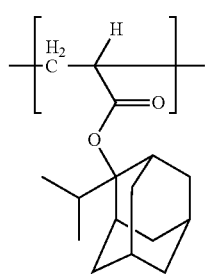
(a1-1-8) 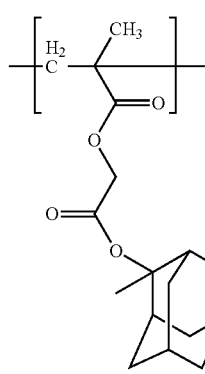
As the structural unit represented by the formula (a1-2), preferred are those represented by formulae (a1-2-1), (a1-2-2), (a1-2-3), (a1-2-4), (a1-2-5), (a1-2-6), (a1-2-7), (a1-2-8), (a1-2-9), (a1-2-10), (a1-2-11) and (a1-2-12), more preferred are those represented by formulae (a1-2-1), (a1-2-2), (a1-2-3), (a1-2-4), (a1-2-9) and (a1-2-10), and still more preferred are those represented by formulae (a1-2-3) and (a1-2-9), and particularly more preferred are those represented by formula (a1-2-3).
(a1-2-1) 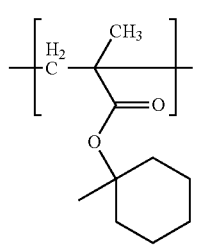

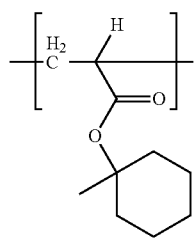 (a1-2-2)

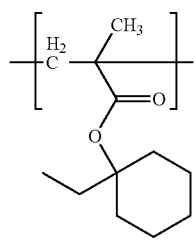 (a1-2-3)

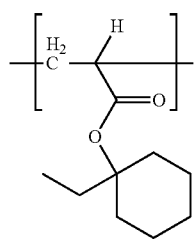 (a1-2-4)

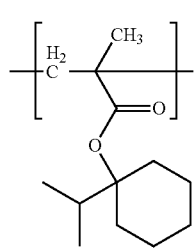 (a1-2-5)

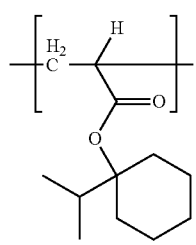 (a1-2-6)

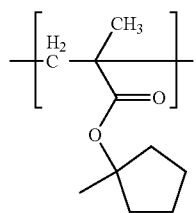 (a1-2-7)

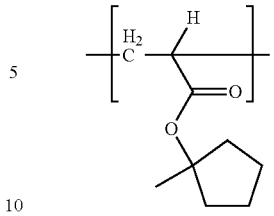 (a1-2-8)

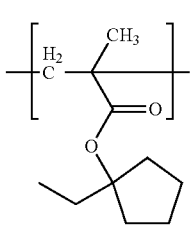 (a1-2-9)

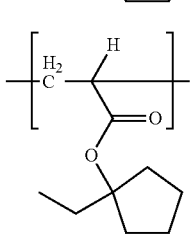 (a1-2-10)

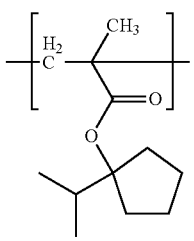 (a1-2-11)

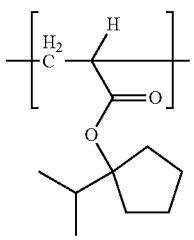 (a1-2-12)

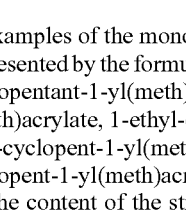

examples of the monomer from which the structural units represented by the formula (a1-2) are derived include 1-ethyl-cyclopentant-1-yl(meth)acrylate, 1-ethyl-cyclohexan-1-yl(meth)acrylate, 1-ethyl-cyclohept-1-yl(meth)acrylate, 1-methyl-cyclopent-1-yl(meth)acrylate, and 1-isopropyl-cyclopent-1-yl(meth)acrylate.

The content of the structural unit represented by the formula (a1-1) and/or the formula (a1-2) in the resin (A) is preferably 10 to 95% by mole, more preferably 15 to 90% by mole, still more preferably 20 to 85% by mole, particularly more preferably 20 to 60% by mole based on 100% by mole of all the structural units of the resin (A).

When the resin (A) has an adamantane ring-containing structural unit, preferably the structural unit represented by formula (a1-1), the content of the adamantane ring-containing structural unit is preferably 15% or more by mole based on 100% by mole of all of the structural unit represented by formula (a1). When the resin (A) has an adamantane ring-containing structural unit in such amount as mentioned above, the photoresist pattern obtained from the photoresist composition comprising the resin (A) can have more improved resistance to dry-etching. The content of the structural unit represented by the formula (a1-1) and/or the formula (a1-2) can be controlled by adjusting the amount of the compounds from which the structural unit represented by the formula (a1-1) and/or the formula (a1-2) is derived at production of the resin (A). The resin (A) has more preferably the structural unit represented by formula (a1-1), of those represented by formulae (a1-1) and (a1-2).

Other structural units having an acid-labile group include a structural unit derived from the monomer represented by formula (a1-3).

The resin which has the structural unit derived from the monomer represented by formula (a1-3) has a norbornene ring, which is a rigid structure, at its main chain, so that the photoresist composition comprising such resin can provide a resist pattern excellent in resistance to dry-etching.

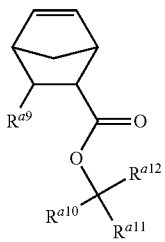

(a1-3)

wherein $R^{a9}$ represents a hydrogen atom; a C1-C3 aliphatic hydrocarbon group which can have a substituent, e.g. a hydroxy group; a carboxyl group; a cyano group; or —COOR$^{a13}$ where $R^{a13}$ represents a C1-C8 aliphatic hydrocarbon group which can have a hydroxy group and in which a methylene group can be replaced by —O— or —CO—, $R^{a10}$, $R^{a11}$ and $R^{a12}$ each independently represent a C1-C12 aliphatic hydrocarbon group which can have a hydroxy group and in which a methylene group can be replaced by —O— or —CO—, and $R^{a10}$ and $R^{a11}$ can be bonded each other to form a C3-C20 ring together with the carbon atom to which $R^{a11}$) and $R^{a11}$ are bonded.

Examples of the C1-C3 aliphatic hydrocarbon group which can have a substituent include a methyl group, an ethyl group, a propyl group, a hydroxymethyl group and a 2-hydroxyethyl group. Examples of $R^{a13}$ include a methyl group, an ethyl group, a propyl group, a 2-oxo-oxolan-3-yl group and a 2-oxo-oxolan-4-yl group. Examples of $R^{a10}$, $R^{a11}$ and $R^{12}$ include a methyl group, an ethyl group, a cyclohexyl group, a methylcyclohexyl group, a hydroxycyclohexyl group, an oxocyclohexyl group and an adamantyl group, and examples of the C3-C20 ring formed by bonding $R^{a10}$ and $R^{a11}$ each other together with the carbon atom to which $R^{a10}$ and $R^{a11}$ are bonded include a cyclohexane ring and an adamantane ring.

Examples of the monomer represented by the formula (a1-3) include one mentioned in JP2010-204646, such as tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl)ethyl 5-norbornene-2-carboxylate and 1-(1-adamantyl)-1-methylethyl 5-norbornene-2-carboxylate.

As the monomer represented by the formula (a1-3), preferred are those represented by formulae (a1-3-1), (a1-3-2), (a1-3-3) and (a1-3-4), more preferred are those represented by formulae (a1-3-2), and (a1-3-4), and still more preferred are those represented by formula (a1-3-2).

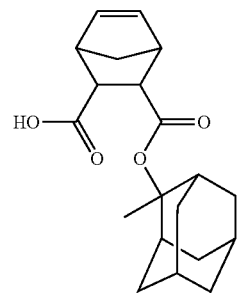

(a1-3-1)

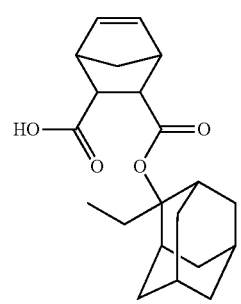

(a1-3-2)

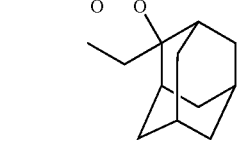

(a1-3-3)

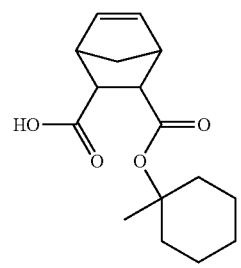

(a1-3-4)

When the resin contains the structural unit derived from the monomer represented by the formula (a1-3), the content of the structural unit derived from the monomer represented by the formula (a1-3) is usually 10 to 95% by mole and preferably 15 to 90% by mole and more preferably 20 to 85% by mole based on total molar of all the structural units of the resin.

Other examples of the compound having an acid-labile group include a monomer represented by the formula (a1-4):

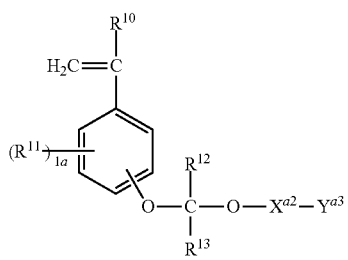

(a1-4)

wherein $R^{10}$ represents a hydrogen atom, a halogen atom, a C1-C6 alkyl group or a C1-C6 halogenated alkyl group, $R^{11}$ is independently in each occurrence a halogen atom, a hydroxy group, a C1-C6 alkyl group, a C1-C6 alkoxy group, a C2-C4 acyl group, a C2-C4 acyloxy group, an acryloyl group or a methacryloyl group, $l^a$ represents an integer of 0 to 4, $R^{12}$ and $R^{13}$ each independently represent a hydrogen atom or a C1-C12 hydrocarbon group, $X^{a2}$ represents a single bond or a C1-C17 aliphatic hydrocarbon group which can have a substituent and in which a methylene group can be replaced by —O—, —CO—, —S—, —SO$_2$— or —N($R^c$)— wherein $R^c$ represents a hydrogen atom or a C1-C6 alkyl group, and $Y^{a3}$ represents C1-C18 hydrocarbon group which can have a substituent.

Examples of the halogen atom include a fluorine atom, a chlorine atom, a bromine atom and an iodine atom.

Examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable.

Examples of the C1-C6 halogenated alkyl group include, preferably fluorine-containing alkyl groups, such as a trifluoromethyl group, a pentafluoroethyl group, a heptafluoropropyl croup, a heptafluoroisopropyl group, a nonafluorobutyl group, a nonafluoro-sec-butyl group, a nonafluoro-tert-butyl group, a perfluoropentyl group, a perfluorohexyl group, a perchloromethyl group, a perbromomethyl group and a periodomethyl group.

Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable.

Examples of the C2-C4 acyl group include an acetyl group, a propionyl group and a butyryl group, and examples of the C2-C4 acyloxy group include an acetyloxy group, a propionyloxy group and a butyryloxy group.

Examples of the C1-C12 hydrocarbon group include a C1-C12 aliphatic hydrocarbon group such as a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group, a C3-C12 alicyclic hydrocarbon group such as a cyclohexyl group, an adamantyl group, a 2-alkyl-2-adamantyl group, a 1-(1-adamantyl)-1-alkyl group and an isobornyl group, an C6-C12 aromatic hydrocarbon group and a group formed by combining one or more above-mentioned groups. Among them, preferred are an isopropyl group, a butyl group, a sec-butyl group, a tart-butyl group, a pentyl group, a hexyl group, an octyl group, a 2-ethylhexyl group, a cyclohexyl group, an adamantyl group, a 2-alkyl-2-adamantyl group, a 1-(1-adamantyl)-1-alkyl group and an isobornyl group.

Examples of the C1-C17 divalent saturated hydrocarbon group include a C1-C17 alkanediyl group such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group.

Examples of the C1-C12 aliphatic hydrocarbon group include a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group. Examples of the C3-C18 saturated cyclic hydrocarbon group include a, cyclopropyl group, a cyclobutyl group, a cyclopentyl group, a cyclohexyl group, a cycloheptyl group, a cyclooctyl group, a cyclononyl group, a cyclodecyl group, a norbornyl group, a 1-adamantyl group, a 2-adamantyl group, an isobornyl group and the following groups:

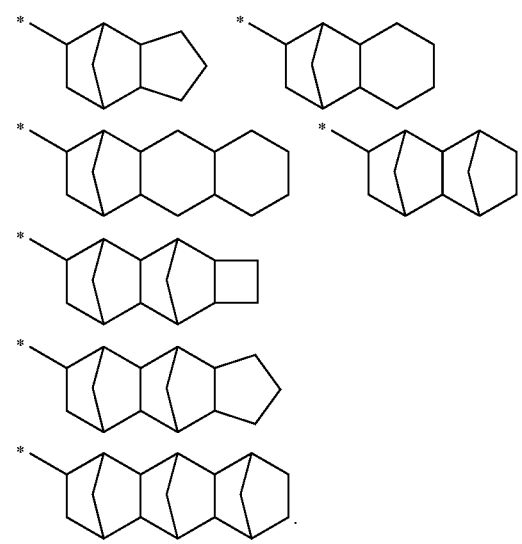

Examples of the C6-C18 aromatic hydrocarbon group include a phenyl group, a naphthyl group, an anthryl group, a p-methylphenyl group, a p-tert-butylphenyl group and a p-adamantylphenyl group.

The substituents in $X^{a2}$ and $Y^{a3}$ include a halogen atom, a hydroxy group, a C1-C6 alkyl group, a C1-C6 alkoxy group, a C2-C4 acyl group and a C2-C4 acyloxy group. Preferred substituents in $X^{a2}$ and $Y^{a3}$ are a hydroxy group.

The monomer represented by the formula (a1-4) includes those mentioned in JP2010-204646, preferred are the monomers represented by the formulae (a1-4-1), (a1-4-2), (a1-4-3), (a1-4-4), (a1-4-5), (a1-4-6) and (a1-4-7) and more preferred are the monomers represented lay the formulae (a1-4-1), (a1-4-2), (a1-4-3), (a1-4-4) and (a1-4-5).

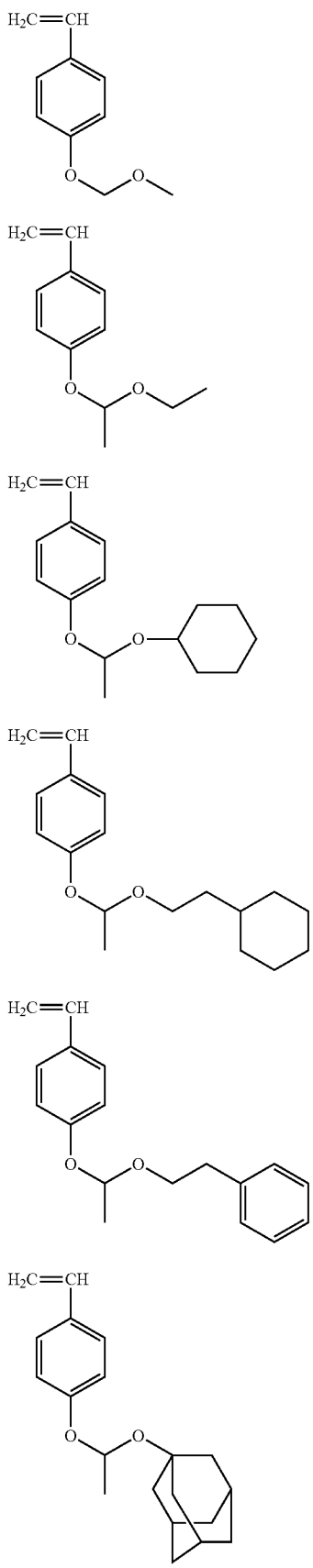

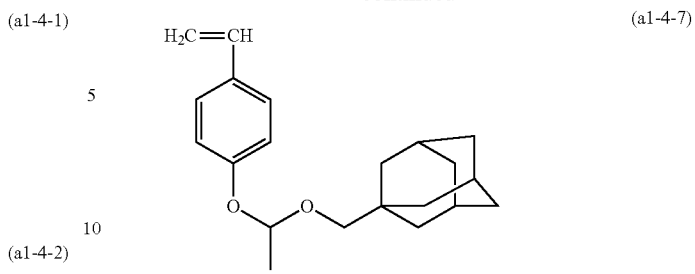

When the resin contains the structural unit derived from the monomer represented by the formula (a1-4), the content of the structural unit derived from the monomer represented by the formula (a1-4) is usually 10 to 95% by mole and preferably 15 to 90% by mole and more preferably 20 to 85% by mole based on total molar of all the structural units of the resin.

Other examples of the compound having an acid-labile group include a monomer represented by the formula (a1-5);

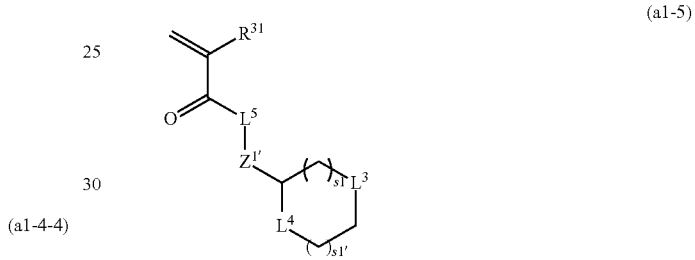

wherein $R^{31}$ represents a hydrogen atom, a halogen atom, a C1-C6 alkyl group which can have a halogen atom, $L^5$ represents —O—, —S— or *-O—$(CH_2)_{k4}$—CO—O—, k4 represents an integer of 1 to 7, *represents a binding position to —CO—, $L^3$ and $L^4$ independently each represent —O—, —S—, or —O—$(CH_2)_{k5}$—CO—O—, k5 represents an integer of 1 to 7, $Z^{1'}$ represents a single bond or a C1-C6 alkylene group in which a methylene group can be replaced by —O— or —CO—, $s^1$ and $s^{1'}$ independently each represent an integer of 0 to 4.

$R^{31}$ is preferably a hydrogen atom, a methyl group, or trifluoromethyl group.

$L^5$ is preferably —O—.

It is preferred that one of $L^3$ and $L^4$ is —O— and the other is —S—.

In the formula (a1-5), $s^1$ is preferably 1 and $s^{1'}$ is preferably 0, 1 or 2.

$Z^1$ is preferably a single bond or —$CH_2$—CO—O—.

Examples of the monomer represented by the formula (a1-5) include the following.

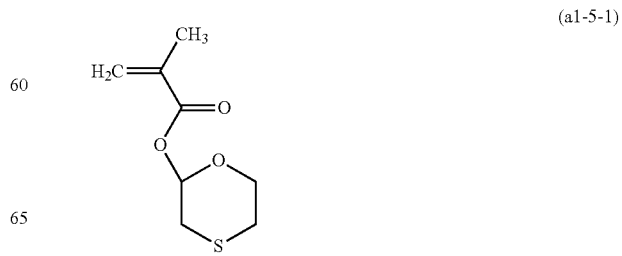

-continued

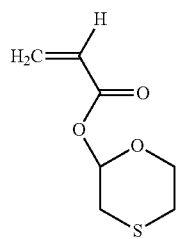

(a1-5-2)

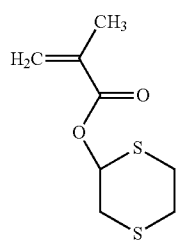

(a1-5-3)

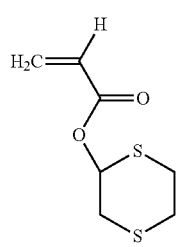

(a1-5-4)

When the resin contains the structural unit derived from the monomer represented by the formula (a1-5), the content of the structural unit derived from the monomer represented by the formula (a1-5) is preferably 1 to 95% by mole and more preferably 3 to 90% by mole and still more preferably 5 to 85% by mole based on total molar of all the structural units of the resin.

The resin (A) may further comprise a structural unit having no acid-labile group. The resin (A) may further comprise one or more kinds of structural units having no acid-labile group. The content of the structural unit having an acid-labile group is preferably 10 to 80% by mole, more preferably 20 to 60% by mole of the total mole amount of all of structural units in the resin (A).

In case where the resin (A) comprises a structural unit having no acid-labile group, the molar ratio of the structural unit having an acid-labile group to the structural unit having no acid-labile group is preferably (10 to 80)/(90 to 20), more preferably (20 to 60)/(80 to 40) [=(the structural unit having an acid-labile group/the structural unit having no acid-labile group)]. When the resin (A) has the structural units in such amount as mentioned above, the photoresist pattern obtained from the photoresist composition comprising the resin (A) can have more improved resistance to dry-etching.

The structural unit having no acid-labile group preferably has a hydroxy group or a lactone ring.

When the resin (A) has a structural unit having no acid-labile group but having a hydroxy group or a lactone ring, the photoresist composition comprising such resin can show adhesiveness of photoresist to a substrate and provide a photoresist pattern with good resolution.

The resin (A) may comprise one or more kinds of structural units having no acid-labile group but having a hydroxy group.

The structural unit having no acid-labile group in the resin (A) can be suitably selected depending on exposure source for producing photoresist pattern from the photoresist composition having comprising the resin (A).

When KrF excimer laser (wavelength: 248 nm) lithography system, or a high energy laser such as electron beam and extreme ultraviolet is used as an exposure system, preferred is a resin which has the structural unit having no acid-labile group but having a phenolic-hydroxy group. When ArF excimer laser (wavelength: 193 nm) is used as an exposure system, preferred is a resin which has the structural unit represented by the formula (a2-1).

The structural unit having no acid-labile group but having a hydroxy group, preferably has a hydroxyadamantyl group.

Preferred examples of the structural unit having no acid-labile group but having a hydroxy group include a structural unit represented by the formula (a2-1):

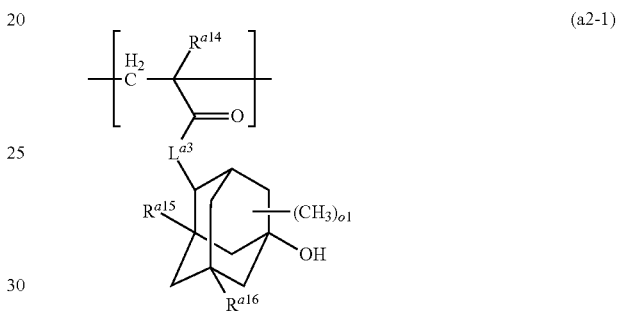

(a2-1)

wherein $R^{a14}$ represents a hydrogen atom or a methyl group, $R^{a15}$ and $R^{a16}$ each independently represent a hydrogen atom, a methyl group or a hydroxy group, $L^a$ represents *—O— or *-O—$(CH_2)_{k2}$—CO—O— in which * represents a binding position to —CO—, and k2 represents an integer of 1 to 7, and o1 represents an integer of 0 to 10.

In the formula (a2-1), $L^{a3}$ is preferably *-O— or *-O—$(CH_2)_{f2}$—CO—O— in which * represents a binding position to —CO—, and f2 represents an integer of 1 to 4, is more preferably *-O— and *-O—$CH_2$—CO—O—, and is still more preferably *-O—.

$R^{a14}$ is preferably a methyl group. $R^{a15}$ is preferably a hydrogen atom. $R^{a16}$ is preferably a hydrogen atom or a hydroxy group. o1 is preferably 0, 1, 2 or 3 and is more preferably 0 or 1.

The structural unit represented by the formula (a2-1) includes those represented by the formula as follow:

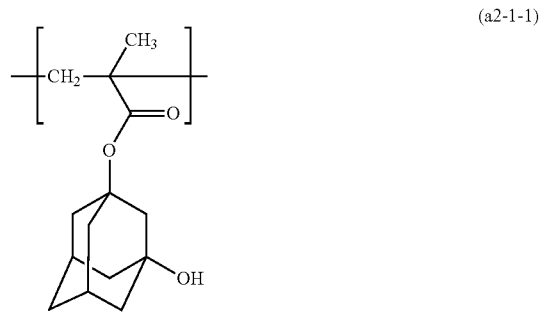

(a2-1-1)

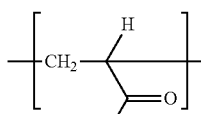 (a2-1-2)

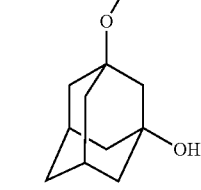 (a2-1-3)

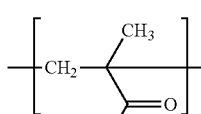 (a2-1-4)

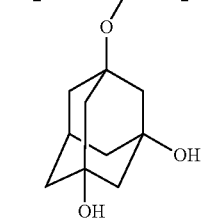 (a2-1-5)

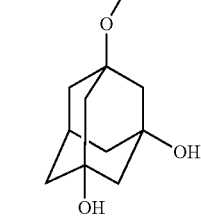 (a2-1-6)

The structural unit represented by formula (a2-1) includes those derived from the compounds mentioned in JP2010-204646A.

Among them, preferred are the structural units represented by formulae (a2-1-1), (a2-1-2), (a2-1-3) and (a2-1-4), more preferred are the structural units represented by formulae (a2-1-1) and (a2-1-3).

when the resin has the structural unit represented by the formula (a2-1), the content of the structural unit represented by the formula (a2-1) is usually 3 to 45% by mole, and preferably 5 to 40% by mole, and more preferably 5 to 35% by mole, based, on total molar of all the structural units of the resin.

Examples of the structural unit having no acid-labile group and having a phenolic hydroxy group include one represented by the formula (a2-0):

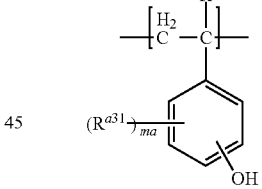 (a2-0)

wherein $R^{a30}$ represents a hydrogen atom, a halogen atom, a C1-C6 alkyl group or a C1-C6 halogenated alkyl group, $R^{a31}$ is independently in each occurrence a halogen atom, a hydroxy group, a C1-C6 alkyl group, a C1-C6 alkoxy group, a C2-C4 acyl group, a C2-C4 acyloxy group, an acryloyl group or a Methacryloyl group, ma represents an integer of 0 to 4.

In the formula (a2-0), examples of the halogen atom include a fluorine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group. Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. $R^{a30}$) represents preferably a C1-C4 alkyl group, more preferably a C1-C2 alkyl group, and still more preferably a methyl group.

Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group. Examples of the C2-C4 acyl group include an acetyl group, a propionyl group and a butyryl group, and examples of the C2-C4 acyloxy group include an acetyloxy group, a propionyloxy group and a butyryloxy group. $R^{a31}$ represents preferably a C1-C4 alkoxy group, more preferably a C1-C2 alkoxy group, and still more preferably a methoxy group.

In the formula (a2-0), ma is preferably 0, 1 or 2, and is more preferably 0 or 1, and especially preferably 0.

The structural unit represented by the formula (a2-0) is preferably represented by the formulae (a2-0-1) (a2-0-1), (a2-0-3) and (a2-0-4). Monomers from which such unit is derived include compounds mentioned in JP2010-204634A.

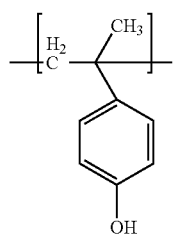

(a2-0-1)

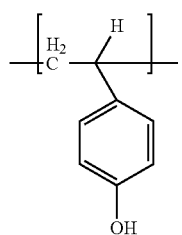

(a2-0-2)

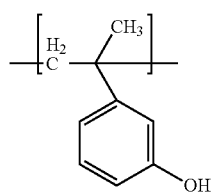

(a2-0-3)

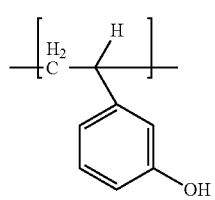

(a2-0-4)

The resin having the structural unit represented by the formula (a2-0) can be produced, for example, by polymerizing a compound in which a hydroxy group has been protected with a protecting group such as an acetyl group and from which the structural unit represented by the formula (a2-0) is derived, followed by conducting deprotection of the obtained polymer with an acid or a base.

The resin having the structural unit represented by the formula (a2-0) can be produced from a hydroxylstylene as a monomer. Among them, preferred are 4-hydroxystyrene and 4-hydroxy-α-methylstyrene.

When such resin is produced from a hydroxylstylene, it can be produced by protecting a phenolic hydroxy group with an acetyl group to produce acetylhydroxylstylene, polymerizing acetylhydroxylstylene to obtain a resin having the structural unit represented by the formula (a2), followed by deprotecting acetylhydroxy groups of the resin to obtain a resin having the structural unit represented by the formula (a2-0). The deprotection of acetylhydroxy groups requires not remarkably detracting from other structural units such as the unit (a1).

When the resin (A) has the structural unit represented by the formula (a2-0), the content of the structural unit represented by the formula (a2-0) is usually 10 to 90% by mole and preferably 10 to 85% by mole and more preferably 15 to 80% by mole based on total molar of all the structural units of the resin.

As to the structural unit having no acid-labile group but having a lactone ring, examples of the lactone ring include a monocyclic lactone ring such as β-propiolactone ring, γ-butyrolactone ring and δ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the structural unit having no acid-labile group but having a lactone ring include those represented by the formulae (a3-1), (a3-2) and (a3-3):

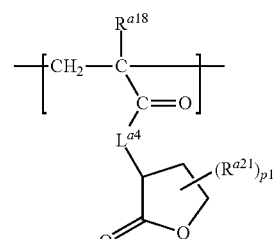

(a3-1)

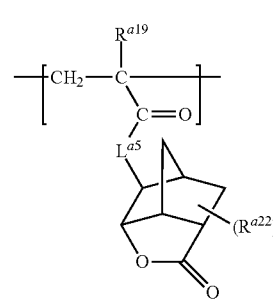

(a3-2)

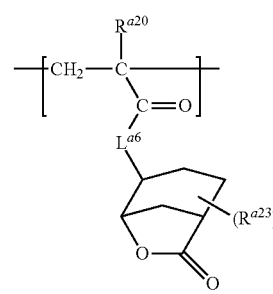

(a3-3)

wherein $L^{a4}$, $L^{a5}$ and $L^{a6}$ each independently represent *-O— or *-O—(CH$_2$)$_{k3}$—CO—O— in which * represents a binding position to —CO— and k3 represents an integer of 1 to 7, $R^{a18}$, $R^{a19}$ and $R^{a20}$ each independently represent a hydrogen atom or a methyl group, $R^{a21}$ represents a C1-C4 aliphatic hydrocarbon group, $R^{a22}$ and $R^{a23}$ are independently in each occurrence a carboxyl group, a cyano group or a C1-C4 aliphatic hydrocarbon group, and p1 represents an integer of 0 to 5, q1 and r1 independently each represent an integer of 0 to 3.

It is preferred that $L^{a4}$, $L^{a5}$ and $L^{a6}$ each independently represent *-O— or *-O—(CH$_2$)$_{d1}$—CO—O— in which * represents a binding position to —CO— and d1 represents an integer of 1 to 4, and it is more preferred that $L^{a4}$, $L^{5a}$ and $L^{a6}$ are *-O— and *-O—CH$_2$—CO—O—, and it is still more preferred that $L^{a4}$, $L^{a5}$ and $L^{a6}$ are *-O—.

$R^{a18}$, $R^{a19}$ and $R^{a20}$ are preferably methyl groups. $R^{a21}$ is preferably a hydrogen atom. It is preferred that $R^{a22}$ and $R^{a23}$ are independently in each occurrence a carboxyl group, a cyano group or a methyl group. It is preferred that p1 is an integer of 0 to 2, and it is more preferred that p1 is 0 or 1. It is preferred that q1 and r1 independently each represent an integer of 0 to 2, and it is more preferred that q1 and r1 independently each represent 0 or 1.

Preferred examples of the structural unit represented by the formula (a3-1) include those represented by the formula (a3-1-1), the formula (a3-1-2), the formula (a3-1-3) or the formula (a3-1-4).

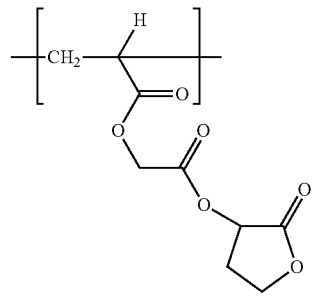
(a3-1-1)

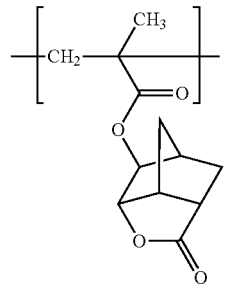
(a3-1-2)

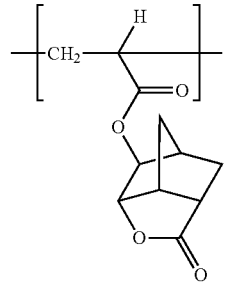
(a3-1-3)

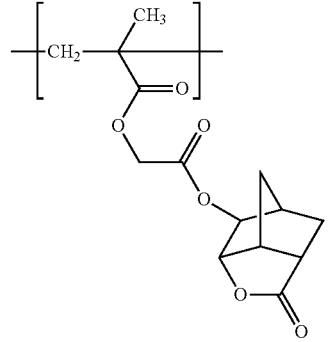
(a3-1-4)

Examples of the structural unit represented by the formula (a3-2) include preferably those represented by the formula (a3-2-1), the formula (a3-2-2), the formula (a3-2-3) or the formula (a3-2-4).

(a3-2-1)

(a3-2-2)

(a3-2-3)

-continued

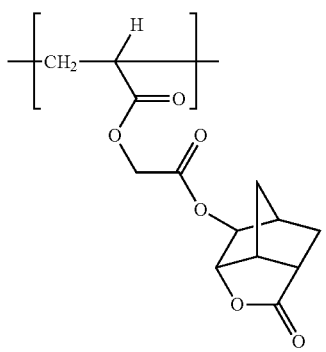
(a3-2-4)

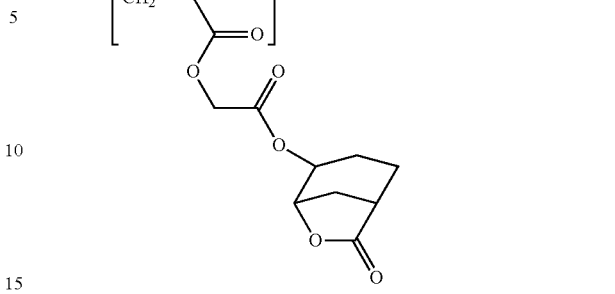
(a3-3-4)

Preferred examples of the structural unit represented by the formula (a3-3) include those represented by the formula (a3-3-1), the formula (a3-3-2), the formula (a3-3-3) or the formula (a3-3-4).

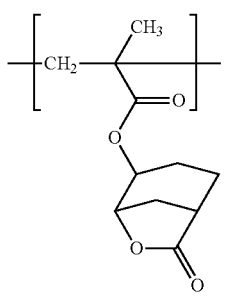
(a3-3-1)

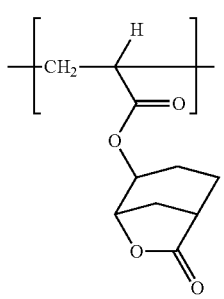
(a3-3-2)

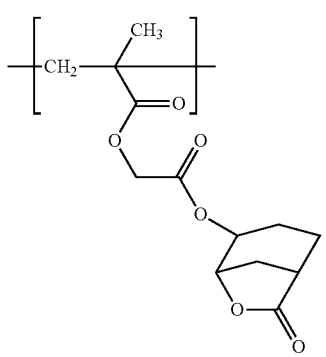
(a3-3-3)

Preferred structural unit having no acid-labile group but having a lactone ring are those represented by the formulae (a3-1-1), (a3-2-2), (a3-2-3) and (a3-2-4), and more preferred are those represented by the formulae (a3-1-1) and (a3-2-3).

The structural units represented by the formula (a3-1), formula (a3-2) and formula (a3-3) can be derived from the counterpart monomers mentioned in JP2010-204646A.

The content of the structural unit having no acid-labile group but having a lactone ring is usually 5 to 70% by mole, preferably 10 to 65% by mole, still more preferably 10 to 60% by mole based on the total molar of all structural units of the resin (A).

When the resin contains the structural unit represented by the formula (a3-1), formula (a3-2) or formula (a3-3), the content thereof is preferably 5 to 60% by mole, more preferably 5 to 50% by mole and still more preferably 10 to 50% by mole, based on total molar of all the structural units of the resin.

The resin may further contain another structural unit having no acid-labile group, besides the structural unit represented by formula (a2) or formula (a3).

The resin may further contain a structural unit derived from a monomer represented by the formula (a4-1), besides the structural unit represented by formula (a2) or formula (a3), as the structural unit having no acid-labile group.

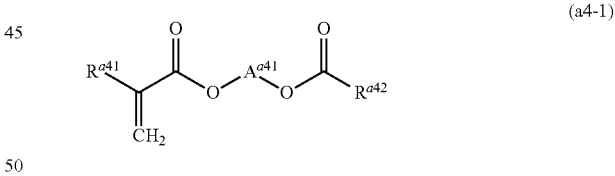
(a4-1)

wherein $R^{a41}$ represents a C1-C12 monovalent aliphatic hydrocarbon group in which a methylene group can be replaced by an oxygen atom or a carbonyl group, or a C6-C12 monovalent aromatic hydrocarbon group;

$A^{a41}$ represents a C1-C6 alkanediyl group which can have a substituent, or a group represented by formula (a-g1)

$$-A^{a42}-(X^{a41}-A^{a43})_s-X^{a42}-A^{a44}- \quad (a\text{-}g1)$$

where s represents 0 or 1, $A^{a42}$ and $A^{a44}$ each independently represent a single bond or a C1-C5 aliphatic hydrocarbon group which can have a substituent, $X^{a41}$ and $X^{a42}$ are independently in each occurrence an oxygen atom, a carbonyl group, a carboxyl group, or an oxycarbonyl group, provided that the carbon atoms of $A^{a42}$, $A^{a43}$, $A^{a44}$, $X^{a41}$ and $X^{a42}$ amount to 6 or less in total; and $R^{a42}$ represents an aliphatic hydrocarbon group which can have a substituent.

In the aliphatic hydrocarbon group represented by $R^{a42}$, any of methylene groups can be replaced by a carbon-carbon double bond, however the aliphatic hydrocarbon group has preferably no carbon-carbon double bond.

The aliphatic hydrocarbon group includes a straight or cyclic alkyl group, alicyclic group, and a group comprising the alkyl group and alicyclic group.

In the aliphatic hydrocarbon group represented by $R^{a42}$, examples of the C1-C12 alkyl group include a methyl group, an ethyl group, a propyl group, an isopropyl group, a butyl group, a pentyl group, a hexyl group, a heptyl group, an octyl group, a decyl group, and a dodecyl group.

The aromatic hydrocarbon group includes a phenyl group, a naphthyl group, an anthryl group, biphenyl group, phenanthryl group, fluorenyl group.

The aliphatic hydrocarbon group represented by $R^{42}$ preferably has a substituent. The substituent for the aliphatic hydrocarbon group is preferably a fluorine atom or a group represented by formula (a-g3)

$$-X^{a43}-A^{a45} \tag{a-g3}$$

in which $X^{a43}$ represents an oxygen atom, a carbonyl group, a carboxyl group, or an oxycarbonyl group, and
$A^{a45}$ represents a C3-C17 aliphatic hydrocarbon group which can have a fluorine atom.
$R^{a42}$ preferably represents a group represented by formula (a-g2)

$$-A^{a46}-X^{a44}-A^{a47} \tag{a-g2}$$

in which $A^{a46}$ represents a C3-C17 aliphatic hydrocarbon group which can have a halogen atom, and
$X^{a44}$ represents a carboxyl group, or an oxycarbonyl group, and
$A^{a47}$ represents a C3-C17 aliphatic hydrocarbon group which can have a halogen atom, provided that the carbon atoms of $A^{a46}$, $A^{a47}$ and
$X^{a44}$ amount to 18 or less in total.

The aliphatic hydrocarbon group includes a straight or cyclic alkyl group having a halogen atom, an alicyclic hydrocarbon group having a halogen atom, a cycloalkyl group having a halogen atom.

Here, the "alkyl group having a halogen atom" means an alkyl group in which any or all of hydrogen atoms have been replaced by a halogen atom, and the "cycloalkyl group having a halogen atom" means a cycloalkyl group in which any or all of hydrogen atoms have been replaced by a halogen atom, The halogen atom includes fluorine atom, chlorine atom, bromine atom, or iodorine atom, preferably fluorine atom.

The monomer represented by the formula (a4-1) wherein $R^{a42}$ represents an ethylene group includes the one represented by formulae (a4-1-1), (a4-1-2), (a4-1-3), (a4-1-4), (a4-1-5), (a4-1-6), (a4-1-7), (a4-1-8), (a4-1-9), (a4-1-10), (a4-1-11), (a4-1-12), (a4-1-13), (a4-1-14), (a4-1-15), (a4-1-16), (a4-1-17), (a4-1-18), (a4-1-19), (a4-1-20), (a4-1-21) and (a4-1-22).

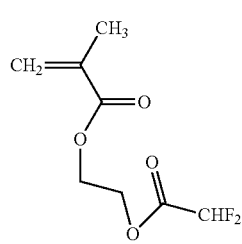

(a4-1-1)

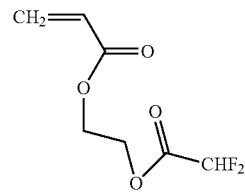

(a4-1-2)

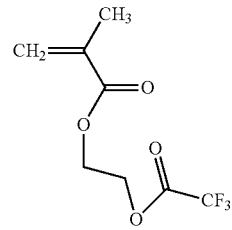

(a4-1-3)

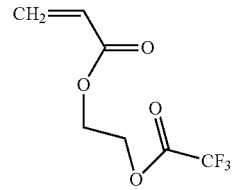

(a4-1-4)

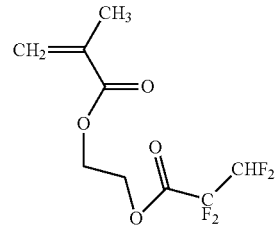

(a1-4-5)

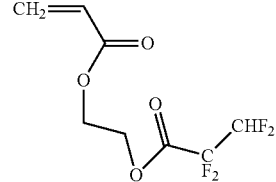

(a4-1-6)

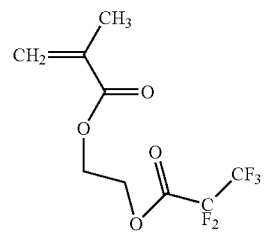

(a4-1-7)

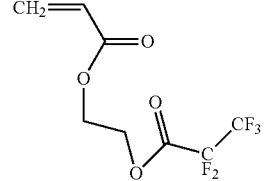

(a4-1-8)

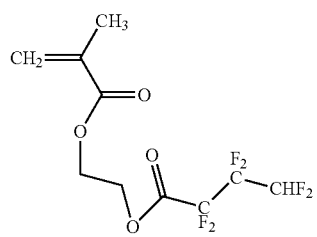 (a4-1-9)
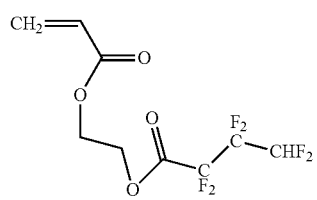 (a4-1-10)
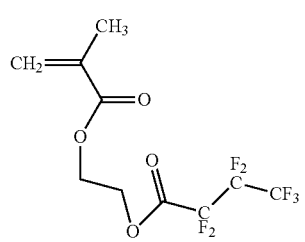 (a4-1-11)
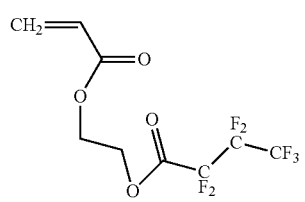 (a4-1-12)
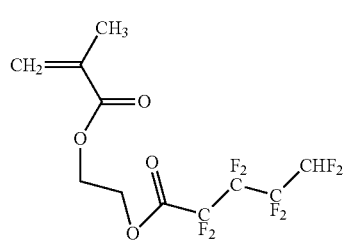 (a4-1-13)
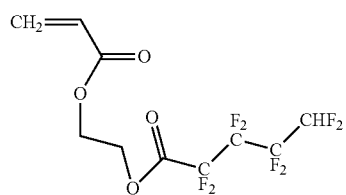 (a4-1-14)
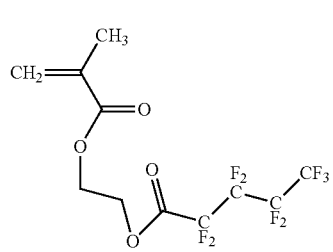 (a4-1-15)
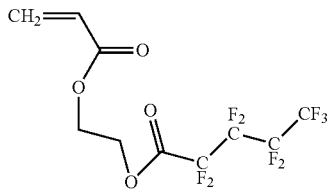 (a4-1-16)
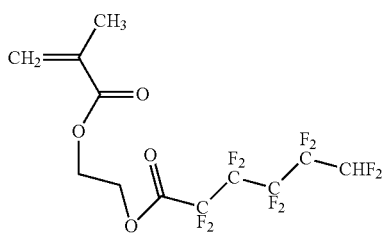 (a4-1-17)
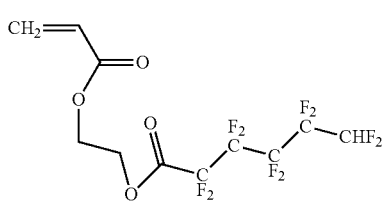 (a4-1-18)
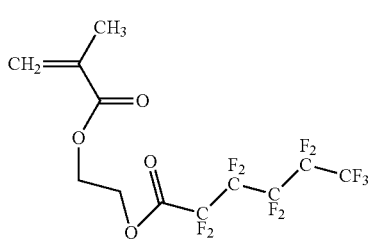 (a4-1-19)
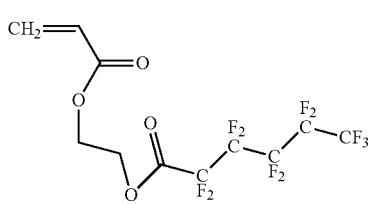 (a4-1-20)
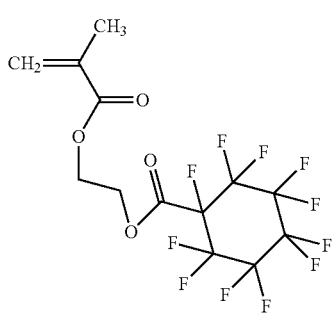 (a4-1-21)

-continued (a4-1-22)
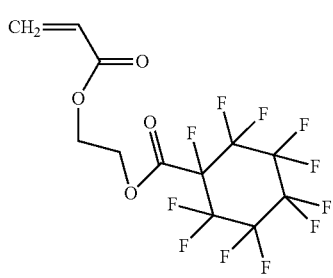

(a4-1'-1)
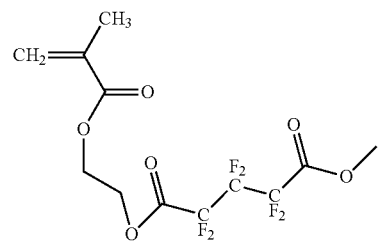

The monomer represented by the formula (a4-1) wherein $R^{a42}$ represents an aliphatic hydrocarbon group having a fluorine atom is preferably a perfluoroalkyl group in which all of hydrogen atoms have been replaced by fluorine atoms or a perfluorocycloalkyl group in which all of hydrogen atoms have been replaced by fluorine atoms.

Examples of the monomer represented by the formula (a4-1) wherein $R^{a42}$ represents a perfluoroalkyl group or a perfluorocycloalkyl group include that represented by formulae (a4-1-3), (a4-1-4), (a4-1-7), (a4-1-8), (a4-1-11), (a4-1-12), (a4-1-15), (a4-1-16), (a4-1-19), (a4-1-20), (a4-1-21) and (a4-1-22). $R^{a42}$ represents preferably a perfluoroalkyl group such as C1-C8 perfluoroalkyl group including a perfluoromethyl group, a perfluoroethyl group, a perfluoropropyl group, a perfluorobutyl group, a perfluoropentyl group, a perfluorohexyl group, a perfluoroheptyl group, a perfluorooctyl group, more preferably C1-C6 perfluoroalkyl group, and still more preferably C1-C3 perfluoroalkyl group.

The aliphatic hydrocarbon group represented by $R^{a42}$ can have one or more groups represented by formula (a-g3). The aliphatic hydrocarbon group has preferably 15 or less, more preferably 12 or less, carbon atoms in total. Considering such total of carbon atoms, the aliphatic hydrocarbon group represented by $R^{a42}$ has preferably one group represented by formula (a-g3).

The monomer represented by formula (a4-1) in which $R^{a42}$ is an aliphatic hydrocarbon group having one group represented by formula (a-g2) is specifically represented by the formula (a4-1').

(a4-1'-2)
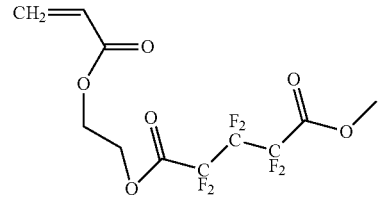

(a4-1'-3)
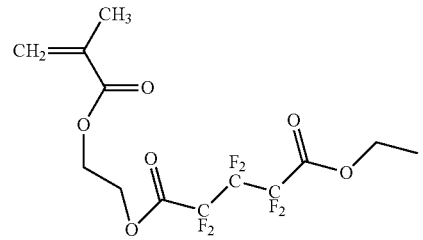

(a4-1'-4)
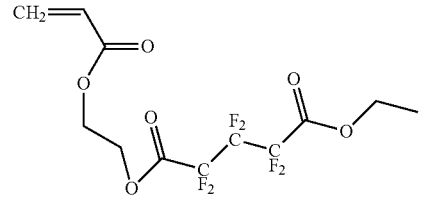

(a4-1'-5)
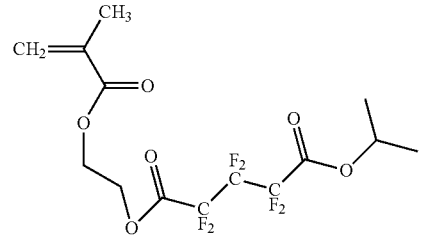

(a4-1')
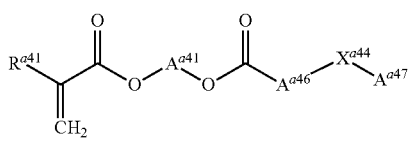

where $R^{a41}$, $A^{a41}$, $A^{a46}$, $X^{a44}$ and $A^{a47}$ are as defined above.

In the formula (a4-1'), $A^{a46}$ or $A^{a47}$ is preferably an aliphatic hydrocarbon group having a halogen atom. More preferred is that $A^{a46}$ is an aliphatic hydrocarbon group having a halogen atom, still more preferred is that $A^{a46}$ is an alkanediyl group having a fluorine atom, particularly more preferred is that $A^{a46}$ is a perfluoroalkanediyl group in which all of hydrogen atoms have been replaced by fluorine atoms.

The monomer represented by the formula (a4-1') wherein $R^{a41}$ represents an ethylene group and $R^{a42}$ represents an perfluoroalkanediyl group includes the one represented by formulae (a4-1'-1), (a4-1'-2), (a4-1'-3), (a4-1'-4), (a4-1'-5), (a4-1'-6), (a4-1'-7), (a4-1'-8), (a4-1'-9), (a4-1'-10), (a4-1'-11), (a4-1'-12), (a4-1'-13), (a4-1'-14), (a4-1'-15), (a4-1'-16), (a4-1'-17), (a4-1''-18), (a4-1'-19), (a4-1'-20), (a4-1'-21) and (a4-1'-22).

(a4-1'-6)
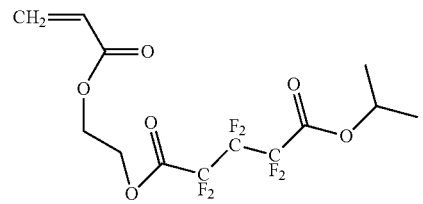

(a4-1'-7)
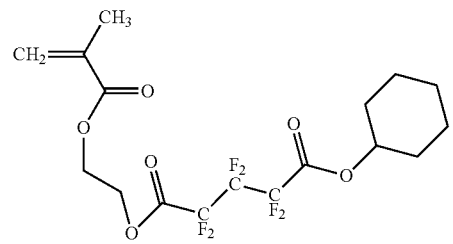

(a4-1'-8)
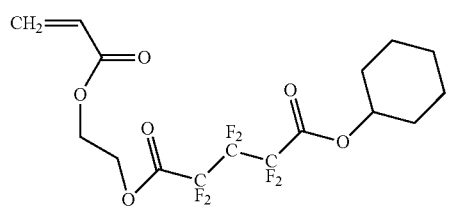
(a4-1'-9)
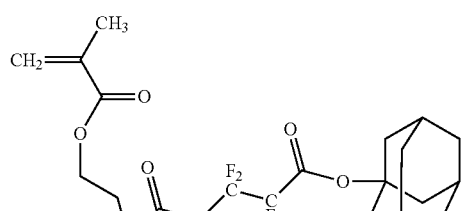
(a4-1'-14)
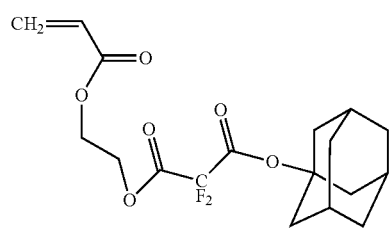
(a4-1'-15)
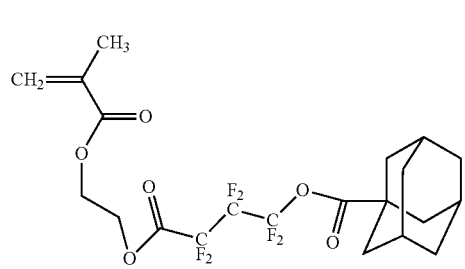
(a4-1'-10)
(a4-1'-16)
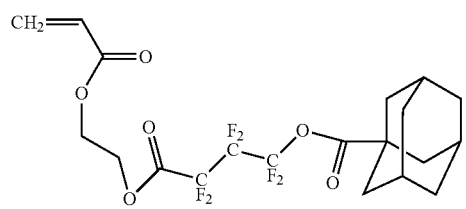
(a4-1'-11)
(a4-1'-17)
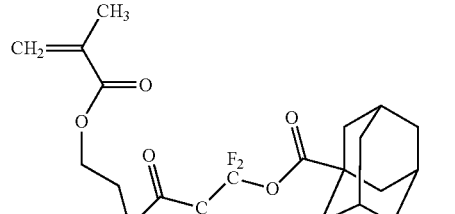
(a4-1'-12)
(a4-1'-18)
(a4-1'-13)
(a4-1'-19)
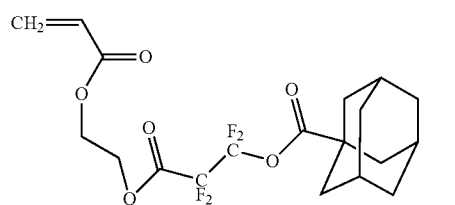

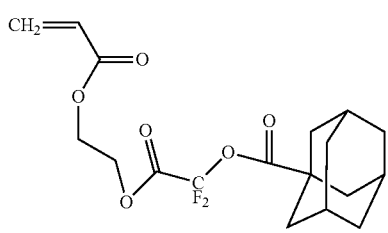
(a4-1'-20)

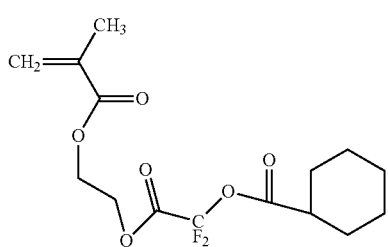
(a4-1'-21)

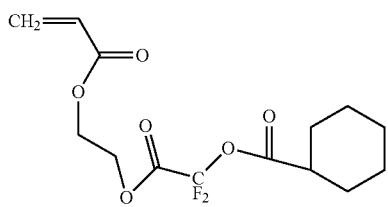
(a4-1'-22)

The aliphatic hydrocarbon group represented by $A^{a46}$ or $A^{a47}$ can have 17 or less carbon atoms, if the total of the carbon atoms which $A^{a46}$ and $A^{a47}$ have are 17 or less. $A^{a46}$ has preferably 1 to 6, more preferably 1 to 3, carbon atoms. $A^{a47}$ has preferably 4 to 15, more preferably 5 to 12, carbon atoms.

$A^{a47}$ is preferably a C6-C12 alicyclic hydrocarbon group, more preferably a cyclohexyl group or an adamantyl group.

When the moiety $*-A^{a46}-X^{a44}-A^{a47}$, where $*$ represents a binding position to a carbonyl group, is represented by the following formulae, the combination of $A^{a46}$ and $A^{a47}$ is preferred.

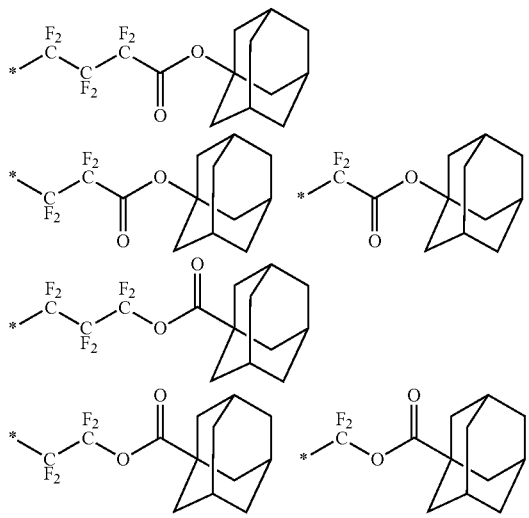

The compounds represented by formulae (a4-1'-9), (a4-1'-10), (a4-1'-11), (a4-1'-12), (a4-1'-13), (a4-1'-14), (a4-1'-15), (a4-1'-16), (a4-1'-17), (a4-1'-18), (a4-1'-19) and (a4-1'-20) have these preferred combination of $A^{a46}$ and $A^{a47}$.

When the resin contains the structural unit derived from the monomer represented by the formula (a4-1), the content of the structural unit derived from the monomer represented by the formula (a4-1) is usually 1 to 20% by mole, preferably 2 to 15% by mole and more preferably 3 to 10% by mole based on total molar of all the structural units of the resin.

The resin (A) may comprise any other structural units than one derived from the monomer represented by formula (a1), (a2), (a3) or (a4)

The resin (A) is generally a polymer of the compound from which the structural unit having an acid labile group is derived, preferably a copolymer of the compound from which the structural unit having an acid labile group is derived and the compound from which the structural unit having no acid labile group is derived, more preferably a copolymer of the compound from which the structural unit represented by formula (a1-1) and/or formula (a1-2) is derived, and the compound from which the structural unit represented by formula (a2) and/or formula (a3) is derived.

The resin (A) preferably has a structural unit having an adamantyl group such as one represented by formula (a1-1) as the structural unit having an acid-labile group.

The resin (A) preferably has a structural unit having a hydroxy adamantyl group such as one represented by formula (a2-1) as the structural unit having no acid-labile group.

The resin (A) has preferably at least one selected from a structural unit having no acid-labile group but having γ-butyrolactone ring, such as one represented by formula (a3-1), and a structural unit having no acid-labile group but having a condensed lactone ring formed from γ-butyrolactone ring and a norbornane ring, such as one represented by formula (a3-2).

The resin (A) can be produced according to known polymerization methods such as radical polymerization.

The resin (A) usually has 2,500 or more of the weight-average molecular weight, preferably 3,000 or more of the weight-average molecular weight. The resin usually has 50,000 or less of the weight-average molecular weight, preferably has 30,000 or less of the weight-average molecular weight.

The weight-average molecular weight can be measured with gel permeation chromatography (standard: polyethylene).

The photoresist composition of the present invention may further comprise another resin than the resin having an acid-labile group. Thus, the photoresist composition may comprise the resin having an acid-labile group and the resin having no acid-labile group, preferably the resin having no acid-labile group but having the structural unit derived from the monomer represented by the formula (a4-1).

In the resin having no acid-labile group but having the structural unit derived from the monomer represented by the formula (a4-1), which resin is sometimes referred to as "resin (X)", the content of the structural unit derived from the monomer represented by the formula (a4-1) is preferably 80% by mole or more, more preferably 85% by mole or more, and still more preferably 90% by mole or more. The resin (X) may substantially consist of the structural unit derived from the monomer represented by the formula (a4-1). The resin (X) may comprise other structural units, such as the structural units represented by the formula (a2) or the formula (a3).

The resin (X) can be obtained usually by polymerizing the monomer represented by the formula (a4-1), as necessary with a monomer having no acid-labile group, such as a compound from which the structural units represented by the formula (a2) or the formula (a3) is derived, in a known manner.

The resin (X) has usually 8,000 or more of the weight-average molecular weight, preferably 10,000 or more of the weight-average molecular weight. The resin usually has 80,000 or less of the weight-average molecular weight, preferably has 60,000 or less of the weight-average molecular weight.

The weight-average molecular weight can be measured with gel permeation chromatography (standard: polyethylene).

The photoresist compositions of the present invention can contain a basic compound as a quencher. The basic compound has the property that it can trap an acid, especially an acid generated from the acid generator by applying a radiation.

The basic compound is preferably a basic nitrogen-containing organic compound, and examples thereof include an amine compound and an ammonium salt. Amine compound includes an aliphatic amine and an aromatic amine. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine.

The basic compounds include preferably a compound represented by the formulae (C1), (C2), (C3), (C4), (C5), (C6), (C7) and (C8), more preferably a compound represented by the formulae (C1), still more preferably a compound represented by the formulae (C1-1).

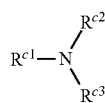

(C1)

wherein $R^{c1}$, $R^{c2}$ and $R^{c3}$ independently represent a hydrogen atom, a C1-C6 alkyl group, a C5-C10 alicyclic hydrocarbon group or a C6-C10 aromatic hydrocarbon group, and the alkyl group and the alicyclic hydrocarbon group can have a substituent selected from the group consisting of a hydroxy group, an amino group and a C1-C6 alkoxy group, and the aromatic hydrocarbon group can have a substituent selected from the group consisting of C1-C6 alkyl groups, a C5-C10 alicyclic hydrocarbon group, a hydroxy group, an amino group, and a C1-C6 alkoxy group,

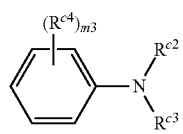

(C1-1)

wherein $R^{c2}$ and $R^{c3}$ are defined as above, each of $R^{c4}$ independently represents a C1-C6 alkyl group, a C1-C6 alkoxy group, a C5-C10 alicyclic hydrocarbon group or a C6-C10 aromatic hydrocarbon group, and m3 represents an integer of 0 to 3,

(C2)

(C3)

(C4)

wherein $R^{c5}$, $R^{c6}$, $R^{c7}$ and $R^{c8}$ are defined same as $R^{c1}$, each of $R^{c9}$ independently represents a C1-C6 alkyl group, a C3-C6 alicyclic group, or a C2-C6 alkanoyl group, and n3 represents an integer of 0 to 8,

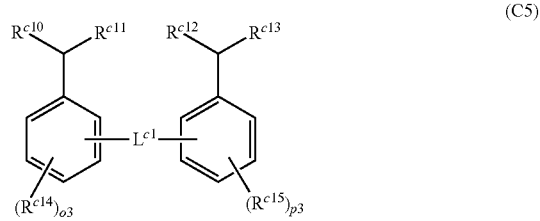

(C5)

(C6)

wherein each of $R^{c10}$, $R^{c11}$, $R^{C12}$, $R^{c13}$ and $R^{c16}$ is defined same as $R^{c1}$, each of $R^{C14}$, $R^{c15}$ and $R^{c17}$ is defined same as $R^{c4}$, $L^{c1}$ represents a C1-C6 alkanediyl group, —CO—, —C(=NH)—, —S— or a combination thereof, and o3 and p3 respectively represent an integer of 0 to 3,

(C7)

(C8)

wherein each of $R^{c18}$, $R^{c19}$ and $R^{c20}$ is defined same as $R^{C4}$, $L^{c2}$ represents a single band, a C1-C6 alkanediyl group, —CO—, —C(=NH)—, —S— or a combination thereof, and q3, r3 and p3 respectively represent an integer of 0 to 3.

Examples of the compound represented by the formula (C1) include 1-naphthylamine, 2-naphthylamine, aniline, diisopropylaniline, 2-methylaniline, 3-methylaniline, 4-methylaniline, 4-nitroaniline, N-methylaniline, N,N-dimethylamine, diphenylamine, hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-diethyldiphenylmethane. Among them, preferred is diisopropylaniline and more preferred is 2,6-diisopropylaniline Examples of the compound represented by the formula (C2) include piperazine.

Examples of the compound represented by the formula (C3) include morpholine.

Examples of the compound represented by the formula (C4) include piperidine and hindered amine compounds having a piperidine skeleton as disclosed in JP 11-52575 A1.

Examples of the compound represented by the formula (C5) include 2,2'-methylenebisaniline.

Examples of the compound represented by the formula (C6) include imidazole and 4-methylimidazole.

Examples of the compound represented by the formula (C7) include pyridine and 4-methylpyridine.

Examples of the compound represented by the formula (C8) include di-2-pyridylketone, 1,2-di(2-pyridyl)ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine, 2,2'-dipicolylamine and bipyridine.

Examples of the ammonium salt include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

The photoresist compositions of the present invention usually contain a solvent.

Examples of the solvent include a glycol ether ester such as ethyl cellosolve acetate, methyl cellosolve acetate and propylene glycol monomethyl ether acetate; an ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The photoresist compositions of the present invention can contain, if necessary, a small amount of various additives such as a sensitizer, a dissolution inhibitor, other polymers, a surfactant, a stabilizer and a dye as long as the effect of the present invention is not prevented.

The photoresist compositions of the present invention can usually be prepared by mixing, in a solvent, an acid generator containing the SALT (I), and a resin (A), and if necessary a basic compound, the resin (X) and/or additives at a suitable ratio for the composition, optionally followed by filtrating the mixture with a filter having 0.2 μm of a pare size.

The order of mixing these components is not limited to any specific order. The temperature at mixing the components is usually 10 to 40° C., which can be selected in view of the resin or the like.

The mixing time is usually 0.5 to 24 hours, which can be selected in view of the temperature. The means for mixing the components is not limited to specific one. The components can be mixed by being stirred.

The amounts of the components in the photoresist compositions can be adjusted by selecting the amount to be used for production of them.

The total content of the acid generator is preferably 0.1 part by weight or more, more preferably 1 part by weight or more, still more preferably 3 part by weight or more, and the content of SALT (I) is preferably 40 parts by weight or less, and more preferably 35 parts by weight or less, per 100 parts by weight of the resin (A).

The content of SALT (I) is preferably 10 part by weight or more, more preferably 30 part by weight or more, per 100 parts by weight of the total amount of the acid generators. The acid generator may consist of SALT (I).

The photoresist composition of the present invention usually contains 80% by weight or more of the resins based on sum of solid component. The photoresist composition of the present invention usually contains 99$ by weight or less of the resins based on sum of solid component. In this specification, "solid component" means components other than solvent in the photoresist composition, When the photoresist composition contains the resin (X), the content of the resin is usually 0.1 to 30 weight parts, preferably 0.5 to 20 weight parts, more preferably 1 to 15 weight parts relative to 100 weight parts of the resin (A).

When the photoresist compositions contain the basic compound, the content thereof is usually 0.01 to 5%, preferably 0.01 to 3%, more preferably 0.01 to 1% by weight based on sum of solid component.

The amount of the solvent is usually 90% by weight or more, preferably 92% by weight or more preferably 94% by weight or more based on total amount of the photoresist composition of the present invention. The amount of the solvent is usually 99.9% by weight or less and preferably 99% by weight or less based on total amount of the photoresist composition of the present invention.

The photoresist compositions of the present invention are useful for a chemically amplified photoresist composition.

A photoresist pattern can be produced using the photoresist composition of the present invention by the following steps (1) to (5):

(1) a step of applying the photoresist composition of the present invention on a substrate, (2) a step of forming a photoresist film by conducting drying, (3) a step of exposing the photoresist film to radiation, (4) a step of baking the exposed photoresist film, and (5) a step of developing the baked photoresist film to form a photoresist pattern.

The applying of the photoresist composition on a substrate is usually conducted using a conventional apparatus such as spin coater. The photoresist composition is preferably filtrated with filter having 0.2 μm of a pore size before applying. Examples of the substrate include a silicon wafer or a quartz wafer on which a sensor, a circuit, a transistor or the like is formed. The substrate may be coated with a reflect-preventing layer such as one containing hexamethyldisilazane. For forming the reflect-preventing layer, such composition for organic reflect-preventing layer as available on the market can be used.

The photoresist film is usually formed by heating the coat layer with a heating apparatus such as hot plate or a decompressor, to thereby dry off the solvent. The heating temperature is preferably 50 to 200° C., and the operation pressure is preferably 1 to $1.0*10^5$ Pa. These conditions can be selected in view of the solvent.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a F2 laser (wavelength: 157 nm), and a light source radiating harmonic laser light in a far UV region or a vacuum UV region by wavelength conversion of laser light from a solid laser light source (such as YAG or semiconductor laser). The exposure source may be electric beam or extremely ultraviolet (EUV).

Exposure through a mask makes the composition layer have exposed areas and unexposed area. At the exposed area, the acid generator contained in the component layer gives an acid due to exposure energy. The acid generated from the acid generator acts on an acid-labile group of the resin, so that the deproteetion reaction proceeds, resulting that the resin shows hydrophilic. Therefore, the resin becomes soluble with an alkaline solution at exposed area of the composition layer. On the other hand, unexposed area of the composition layer remains insoluble or poorly soluble in an aqueous alkali solution even after exposure. The solubility for an aqueous alkali solution is much different between the exposed area and unexposed area.

The step of baking of the exposed photoresist film is so called post-exposure bake, which is conducted with heating means such as hot plates. The temperature of baking of the exposed photoresist film is preferably 50 to 200'C, and more preferably 70 to 150'C. The deprotection reaction further proceeds by post-exposure bake.

The development of the baked photoresist film is usually carried out with alkaline developer using a development apparatus. The development can be conducted by contacting the baked photoresist film into with an aqueous alkaline solution to thereby remove the film at exposed area from the substrate while remain the film at unexposed area, forming the photoresist pattern. The alkaline developer to be used may be any one of various alkaline aqueous solution used in the art. Generally, an aqueous solution of tetramethylammonium hydroxide or (2-hydroxyethyl)trimethylammonium hydroxide (commonly known as "choline") is often used.

After development, the photoresist pattern formed is preferably washed with ultrapure water, and the remained water on the photoresist pattern and the substrate is preferably removed.

The photoresist composition of the present invention is suitable for ArF excimer laser lithography, KrF excimer laser lithography, EUV exposure lithography and EB (electron beam) lithography.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted.

The weight-average molecular weight of any material used in the following examples is a value found by gel permeation chromatography [HLC-8120GPC type, Column: Three of TSKgel Multipore HXL-M with guard column, manufactured by TOSOH CORPORATION, Solvent: tetrahydrofuran, Flow rate: 1.0 mL/min., Detector: RI Detector. Column temperature; 40° C., Injection volume: 100 μL] using standard polystyrene as a standard reference material.

Structures of compounds were determined by mass spectrometry (Liquid Chromatography: 1100 Type, manufactured by AGILENT TECHNOLOGIES LTD., Mass Spectrometry: LC/MSD Type, manufactured by AGILENT TECHNOLOGIES LTD.). Hereinafter, the value of the peak in the mass spectrometry is referred to as "MASS".

Example 1

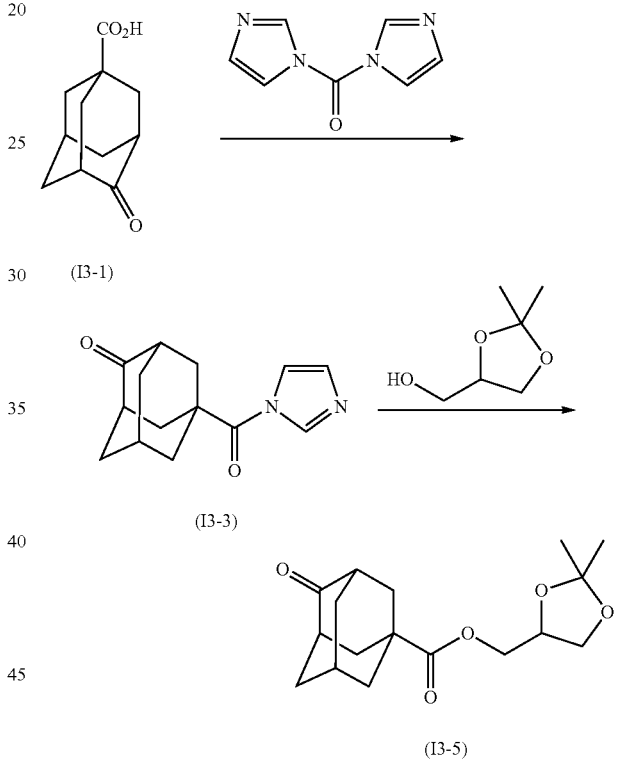

Fed were 6 parts of the compound represented by formula (I3-1) and 30 parts of chloroform into a reactor, followed by stirring them at 23° C. for 30 minutes. To the obtained mixture, 5.51 parts of 1,1'-carbonyldiimidazole was fed and then stirred at 60° C. for 1 hour to obtain a solution containing the compound represented by formula (I3-3). After cooling to 23° C., a mixture of 3.67 parts of 3,3-dimethyl-2,4-dioxacyclopentylmethanol and 3.67 parts of chloroform was dropped over 30 minutes to the obtained solution containing the compound represented by formula (I3-3), and then stirred at 23° C. for 12 hours.

To the resulting reaction mixture, 15 parts of deionized water was added to wash the reactants, followed by separation. Such washing with water was conducted three times.

The extracted organic layer was concentrated by filtration, followed by concentrating the filtrate to obtain 6.12 parts of the compound represented by the formula (I3-5).

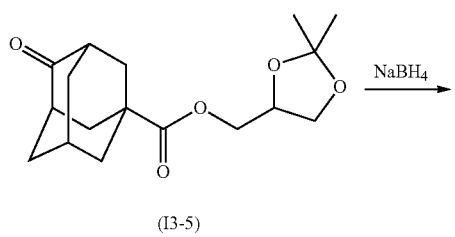

(I3-5)

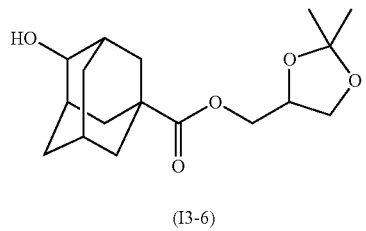

(I3-6)

Fed were 5 parts of the compound represented by formula (I3-5) and 27.85 parts of acetonitrile into a reactor, followed by stirring them at 23° C. for 30 minutes. After cooling the mixture to 0° C., mixture of 0.31 parts of sodiumborohydrate and 3.07 parts of deionized water was dropped over 10 minutes, followed by stirring them at 0° C., for 2 hours. To the reaction mixture, 8.11 parts of 1 N hydrogen hydrochloride was added and then stirred at 23° C. for 30 minutes, followed by concentration.

To the reaction mixture, 44.56 parts of chloroform and 11.14 parts of deionized water were fed and then stirred, followed by separation. Such washing with water was conducted three times. The resulting organic layer was filtrated, and then the resulting filtrate was concentrated. To the concentrated mixture, 37.7 parts of n-heptane was added and then stirred, followed by removing the supernatant therefrom. The residue was dissolved in chloroform and concentrated to obtain 3.27 parts of compound represented by the formula (I3-6).

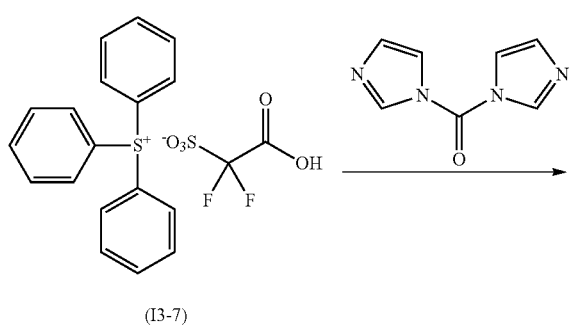

(I3-7)

The salt represented by the formula (I3-7) was prepared by the method mentioned in JP2008-127367.

Fed were 3.87 parts of the salt represented by formula (I3-7) and 19.14 parts of acetonitrile into a reactor, followed by stirring them at 30° C. for 30 minutes. To the resulting mixture, 1.71 parts of 1,1'-carbonyldiimidazole, followed by stirring it at 80° C. for 1 hour to obtain a solution containing the salt represented by the formula (I3-8).

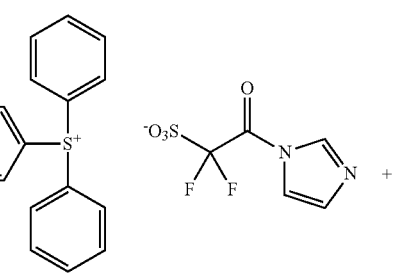

(I3-8)

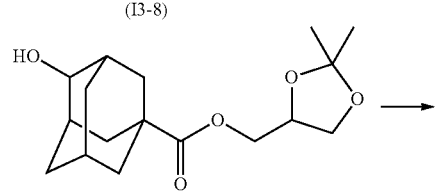

(I3-6)

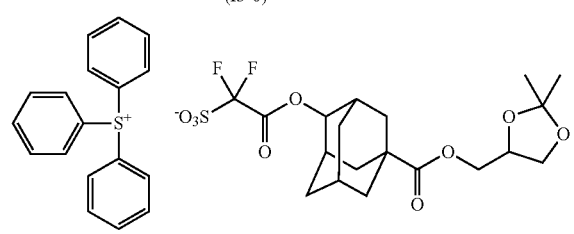

(I3-9)

To the solution after cooling to 23° C., a mixture of 3.27 parts of the compound represented by formula (I3-6) and 3.27 parts of acetonitrile was fed, followed by stirring it at 80° C. for 12 hours. To the resulting mixture, 38.82 parts of chloroform and 9-7 parts of deionized water were fed and then stirred, followed by separation. Such washing with water was conducted five times. To the resulting organic layer, 1 part of activated carbon was added and then stirred at 23° C. for 30 minutes, followed by filtration. The filtrate was concentrated and then 37.9 parts of tert-buthylmethylether was added thereto, followed by removing the supernatant therefrom. The residue was dissolved in chloroform and concentrated to obtain 2.96 parts of salt represented by the formula (I3-9).

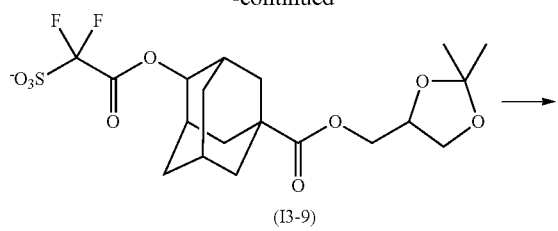

(I3-9)

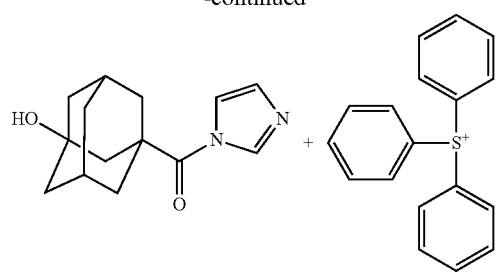

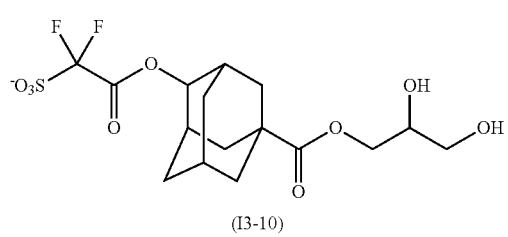

(I3-10)

Fed were 2.96 parts of the salt represented by formula (I3-9) and 16.8 parts of acetonitrile, followed by stirring them at 23° C. for 3D minutes. To the resulting mixture, a mixture of 0.1 parts of oxalic acid and 0.51 parts of deionized water was added and then stirred at 80° C. for 10 hours, followed by concentration. To the resulting mixture, 40.32 parts of chloroform, 10.08 parts of deionized water and 0.3 parts of 28% aqueous ammonia were added and stirred, followed by separation. Such washing with water was conducted twice. The resulting organic layer was filtrated and then the filtrate was concentrated. To the concentrated mixture, 16.75 parts of tert-buthylmethylether was added and then stirred, followed by removing the supernatant therefrom. The residue was dissolved in chloroform and concentrated to obtain 1.09 parts of salt represented by the formula (I3-10),

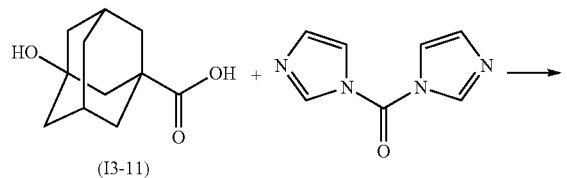

(I3-11)

To a mixture of 0.28 parts of the compound represented by formula (I3-11) and 10 parts of chloroform, 0.24 parts of 1,1'-carbonyldiimidazole was added and then stirred at 23° C. for 3 hours.

To the reaction mixture, 1 part of the salt represented by formula (I3-10) and 10 parts of chloroform were added and then stirred at 23° C. for 1 hour. To the reaction mixture, aqueous potassium carbonate solution was added and then extraction was conducted with chloroform. The obtained organic layer was washed with deionized water, followed by concentration.

The residue was dissolved in acetonitrile and then concentrated. To the resulting concentrate, 6.25 parts of tert-buthylmethylether was added and then stirred, followed by removing the supernatant therefrom.

The resultant residue was dissolved in chloroform, followed by concentration to obtain 0.78 parts of salt represented by the formula (I-3).

MASS (ESI(+) Spectrum): $M^+$ 263.1

MASS (ESI(−) Spectrum): $M^-$ 605.2

Example 2

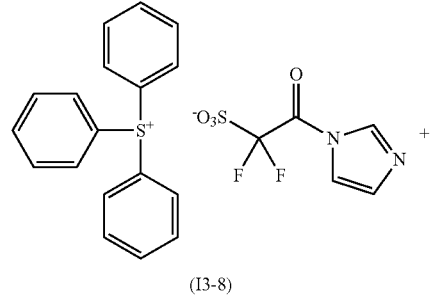

(I3-8)

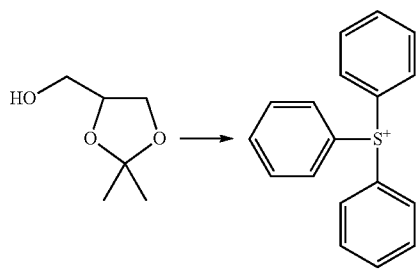

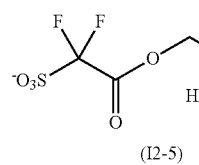

(I2-5)

31.8 parts of a solution containing the salt represented by the formula (I3-8) was prepared by the same method as example 1.

To the obtained solution, 1.35 parts of 3,3-dimethyl-2,4-dioxacyclopentylmethanol was fed, followed by stirring it at 23° C. for 3 hours. To the resulting mixture, 0.1 parts of oxalic acid and 0.51 parts of deionized water were fed and then stirred at 50° C. for 2 hours, followed by concentration to obtain a solution containing the salt represented by the formula (I2-5).

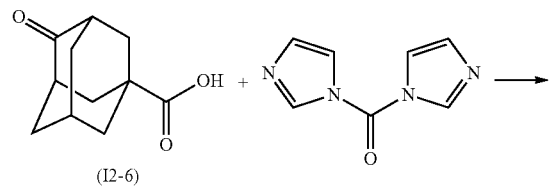

(I2-6)

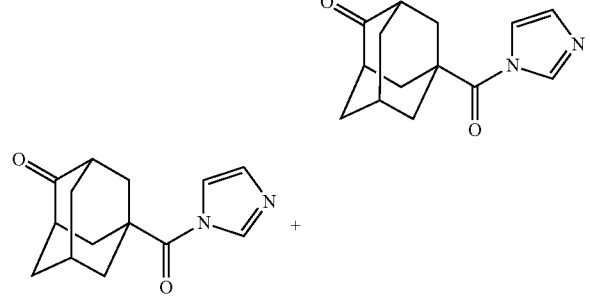

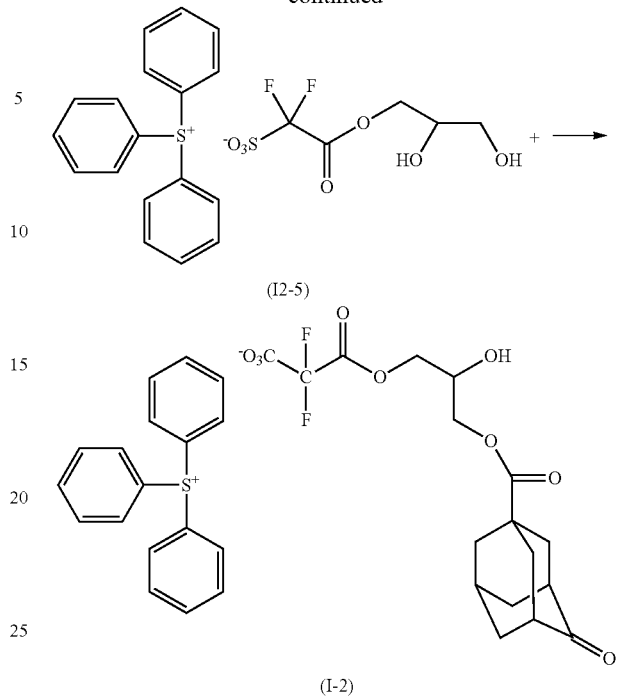

Mixed were 1.98 parts of the compound represented by formula (I2-6) and 30 parts of chloroform, and then 1.65 parts of 1,1'-carbodiimidazole was added thereto, followed by stirring the mixture at 23° C. for 3 hours. To the obtained mixture, the solution containing the salt represented by the formula (I2-5) was added and then stirred at 23° C. for 1 hour.

To the resulting reaction mixture, aqueous potassium carbonate solution was added and then extracted with chloroform. The obtained organic layer was washed with deionized water, followed by concentration.

The residue was dissolved in acetonitrile and then concentrated.

To the resulting concentrate, 20 parts of tert-buthylmethylether was added and then stirred, followed by removing the supernatant therefrom. The residue was dissolved in chloroform and concentrated to obtain 2.91 parts of compound represented by the formula (I-2).

MASS (ESI(+) Spectrum): $M^+$ 263.1
MASS (ESI(−) Spectrum): $M^-$ 425.1

Example 3

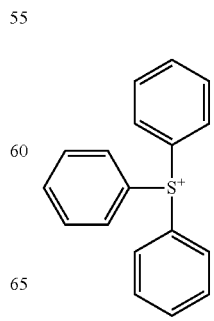

-continued

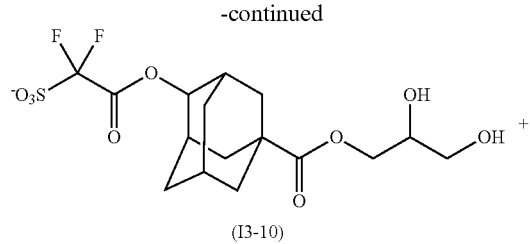

(I3-10)

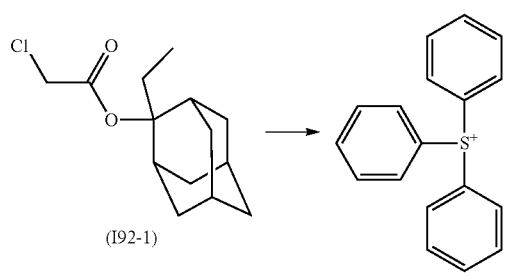

(I92-1)

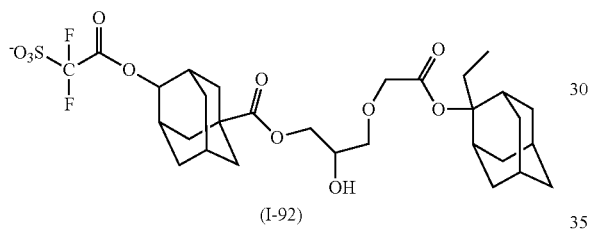

(I-92)

Fed were 1 part of the salt represented by formula (I3-10) and 10 parts of chloroform, followed by stirring the mixture at 23° C. for 30 minutes. To the obtained mixture, 0.14 parts of pyridine was added and then heated to 40° C.

To the obtained mixture, a mixture of 0.37 parts of the compound represented by the formula (I92-1) and 5 parts of chloroform was dropped over 1 hour, followed by stirring it at 40° C. for 8 hours.

Then to the resulting reaction mixture after cooling to 23° C., 10 parts of deionized water was added, stirred, and separated to collect an organic layer.

To the reaction mixture, 10 parts of 10% aqueous potassium carbonate solution at 5° C. was added to wash it, followed by separating into an organic layer. Then to the collected organic layer, 10 parts of deionized water was added to wash it, followed by separating into an organic layer. Such washing with water was conducted three times. The obtained organic layer was concentrated and the resultant residue was dissolved in acetonitrile, followed by concentration. To the resulting concentrate, 5 parts of tert-buthylmethylether was added and then stirred, followed by removing the supernatant therefrom. The residue was dissolved in chloroform and concentrated to obtain 0.38 parts of salt represented by the formula (I-92).

MASS (ESI(+) Spectrum): M$^+$ 263.1

MASS (ESI(−) Spectrum): M$^-$ 647.2

Synthesis of Resin

The compounds used for producing resins were shown as follow.

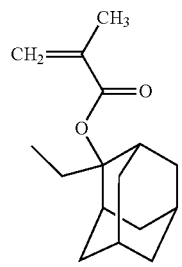

(a1-1-2)

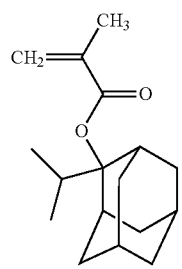

(a1-1-3)

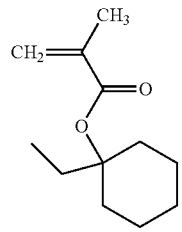

(a1-2-3)

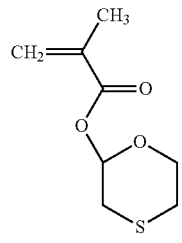

(a1-5-1)

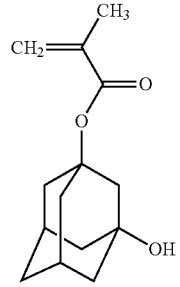

(a2-1-1)

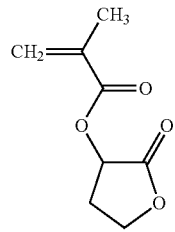

(a3-1-1)

(a3-2-3)

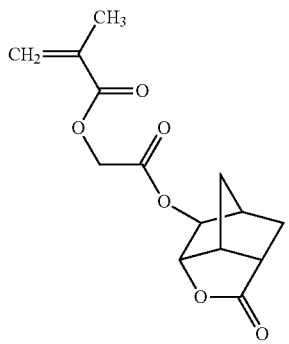

(a4-1-7)

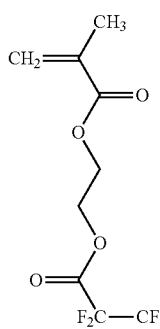

Hereinafter, the compounds of the formulae are referred to as the symbols below the formulae. For example, the compound represented by formula (a1-1-2) is referred to as "monomer (a1-1-2)".

Resin Synthesis Example 1

To a reactor, the monomers (a1-1-3), (a1-2-3), (a2-1-1), (a3-1-1) and (a3-2-3) were mixed in a molar ratio of 30/14/6/20/30 (monomer (a1-1-3)/monomer (a1-2-3)/monomer (a2-1-1)/monomer (a3-1-1)/monomer (a3-2-3)), and 1,4-dioxane was added thereto in the amount ratio of 1.5 times weight parts relative to the total weight parts of all monomers to prepare a mixture. To the mixture, azobisisobutyronitrile in the molar ratio of azobisisobutyronitrile/all monomers=1/100 and azobis(2,4-dimethylvaleronitrile) in the molar ratio of azobis(2,4-dimethylvaleronitrile)/all monomers=3/100 were added as initiators, and the resulting reaction mixture was heated at 73° C. for about 5 hours.

The reaction mixture obtained was poured into a large amount of a mixture of methanol and water (weight ratio=4/1) to cause precipitation, followed by filtrating the mixture to collect precipitates.

The precipitates were dissolved in dioxane, and then the obtained solution was poured into a large amount of a mixture of methanol and water (weight ratio=4/1) to cause precipitation, followed by filtrating the mixture to collect precipitates. This operation was conducted twice for purification, As a result, a resin having a weight-average molecular weight of about $8.1 \times 10^3$ was obtained in a yield of 65%. This resin is called as resin A1. Resin A1 had the following structural units.

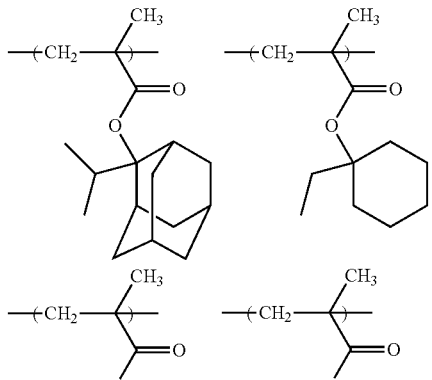

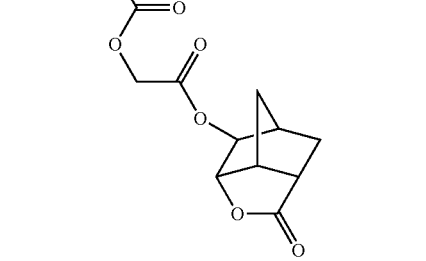

Resin Synthesis Example 2

To a reactor (the monomers (a1-1-2), (a1-2-3), (a2-1-1), (a3-1-1) and (a3-2-3) were mixed in a molar ratio of 30/14/6/20/30 (monomer (a1-1-2)/monomer (a1-2-3)/monomer (a2-1-1)/monomer (a3-1-1)/monomer (a3-2-3)), and 1,4-dioxane was added thereto in the amount ratio of 1.5 times weight parts relative to the total weight parts of all monomers to prepare a mixture. To the mixture, azobisisobutyronitrile in the molar ratio of azobisisobutyronitrile/all monomers=1/100 and azobis(2,4-dimethylvaleronitrile) in the molar ratio of azobis(2,4-dimethylvaleronitrile)/all monomers=3/100 were added as initiators, and the resulting reaction mixture was heated at 73° C. for about 5 hours.

The reaction mixture obtained was poured into a large amount of a mixture of methanol and water (weight ratio=4/1) to cause precipitation, followed by filtrating the mixture to collect precipitates.

The precipitates were dissolved in dioxane, and then the obtained solution was poured into a large amount of a mixture of methanol and water (weight ratio=4/1) to cause precipitation, followed by filtrating the mixture to collect precipitates. This operation was conducted twice for purification.

As a result, a resin having a weight-average molecular weight of about $7.9 \times 10^3$ was obtained in a yield of 68%. This resin is called as resin A2. Resin A2 had the following structural units.

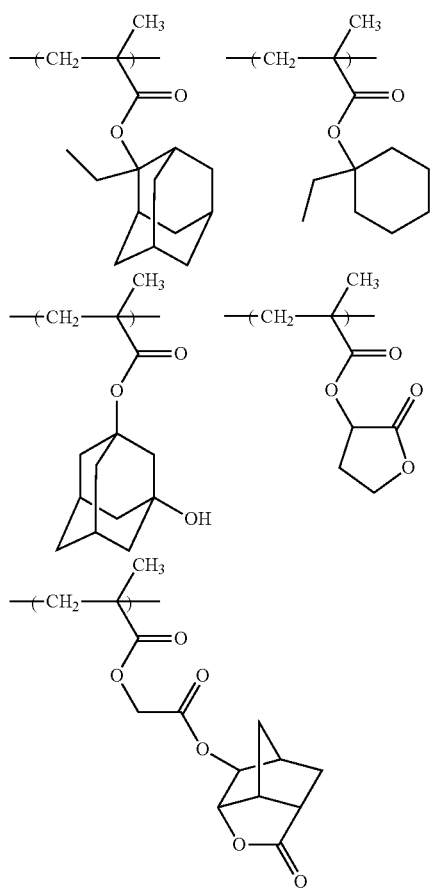

Resin Synthesis Example 3

To a reactor, the monomers (a1-1-2), (a2-1-1) and (a3-1-1) were mixed in a molar ratio of 50/25/25 (monomer (a1-1-2)/monomer (a2-1-1)/monomer (a3-1-1)) and 1,4-dioxane was added thereto in the amount ratio of 1.5 times weight parts relative to the total weight parts of all monomers to prepare a mixture. To the mixture, azobisisobutyronitrile in the molar ratio of azobisisobutyronitrile/all monomers=1/100 and azobis(2,4-dimethylvaleronitrile) in the molar ratio of azobis(2,4-dimethylvaleronitrile)/all monomers=3/100 were added as initiators, and the resulting reaction mixture was heated at 80° C. for about 8 hours.

The reaction mixture obtained was poured into a large amount of a mixture of methanol and water (weight ratio-4/1) to cause precipitation, followed by filtrating the mixture to collect precipitates.

The precipitates were dissolved in dioxane, and then the obtained solution was poured into a large amount of a mixture of methanol and water (weight ratio=4/1) to cause precipitation, followed by filtrating the mixture to collect precipitates. This operation was conducted twice for purification.

As a result, a resin having a weight-average molecular weight of about $9.2 \times 10^3$ was obtained in a yield of 60%. This resin is called as resin A3. Resin A3 had the following structural units.

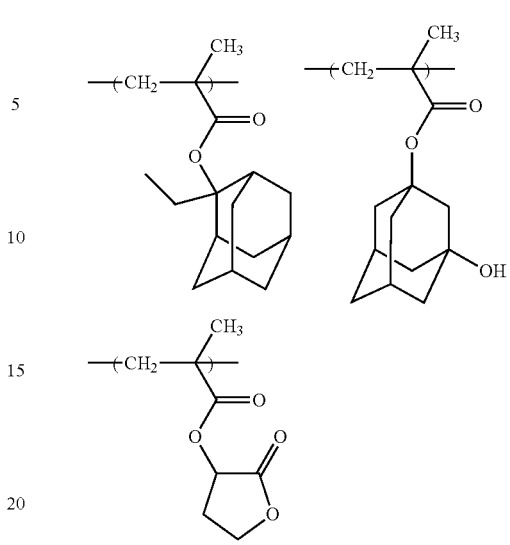

Resin Synthesis Example 4

To a reactor, the monomers (a1-1-2), (a1-5-1) (a2-1-1), (a3-2-3) and (a3-1-1) were mixed in a molar ratio of 30/14/6/20/30 (monomer (a1-1-2)/monomer (a1-5-1)/monomer (a2-1-1)/monomer (a3-2-3)/monomer (a3-1-1)) and 1,4-dioxane was added thereto in the amount ratio of 1.5 times weight parts relative to the total weight parts of all monomers to prepare a mixture. To the mixture, azobisisobutyronitrile in the molar ratio of azobisisobutyronitrile/all monomers=1/100 and azobis(2,4-dimethylvaleronitrile) in the molar ratio of azobis(2,4-dimethylvaleronitrile)/all monomers=3/100 were added as initiators, and the resulting reaction mixture was heated at 75° C. for about 5 hours.

The reaction mixture obtained was poured into a large amount of a mixture of methanol and water (weight ratio=–4/1) to cause precipitation, followed by filtrating the mixture to collect precipitates.

The precipitates were dissolved in dioxane, and then the obtained solution was poured into a large amount of a mixture of methanol and water (weight ratio=4/1) to cause precipitation, followed by filtrating the mixture to collect precipitates. This operation was conducted twice for purification.

As a result, a resin having a weight-average molecular weight of about $7.2 \times 10^3$ was obtained in a yield of 78%. This resin is called as resin A4. Resin A4 had the following structural units.

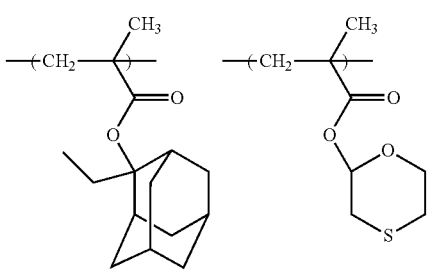

-continued

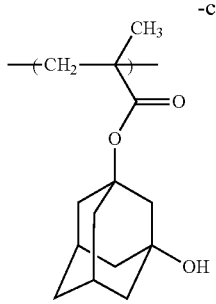

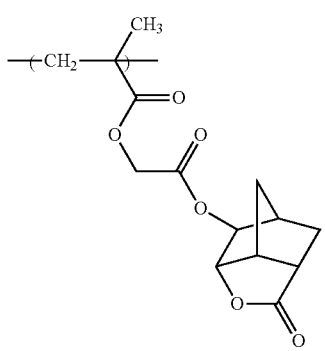

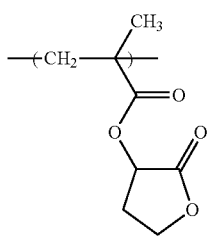

Resin Synthesis Example 5

To monomer (a4-1-7), 1,4-dioxane was added in the amount ratio of 1.5 times weight parts relative to the total parts of all monomer to prepare a mixture. To the mixture, azobisisobutyronitrile as an initiator in the molar ratio of azobisisobutyronitrile/all monomers=0.7/100 and azobis(2,4-dimethylvaleronitrile) as an initiator in the molar ratio of azobis(2,4-dimethylvaleronitrile)/all monomers=2.1/100 were added, and the obtained mixture was heated at 75° C. for about 5 hours. The reaction mixture obtained was poured into a large amount of a mixture of methanol and water (weight ratio=4/1) to cause precipitation. The precipitate was collected by filtration, and then dissolved in dioxane, followed by pouring the resultant solution into a large amount of a mixture of methanol and water to cause precipitation. This operation was conducted twice for purification. As a result, a resin having a weight-average molecular weight of about $1.8 \times 10^4$ was obtained in a yield of 77%. This resin is called as resin X1. Resin X1 had the following structural unit.

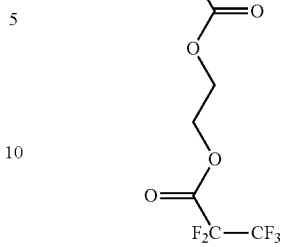

Examples 4 to 12 and Comparative Example 1

(Preparation of Photoresist Composition)

The following components were mixed and dissolved, further, filtrated through a fluorine resin filter having pore diameter of 0.2 μm, to prepare photoresist compositions shown in Table 5.

<Resin (A)>
Resin A1, Resin A2, Resin A3, Resin A4, Resin X1
<Acid Generator>
I-3: The compound represented by formula (I-3)
I-2: The compound represented by formula (I-2)
I-92: The compound represented by formula (I-92)
BI-3: The compound represented by the formula

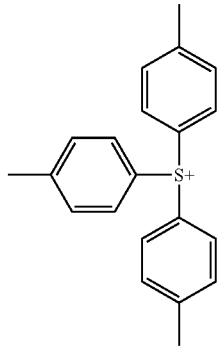

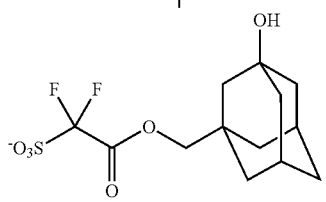

Z1: The compound represented by formula

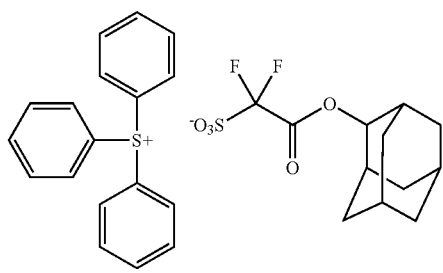

<Quencher>

Basic Compound C1: 2,6-diisopropylaniline

<Solvent>

| propylene glycol monomethyl ether acetate | 265 parts |
| propylene glycol monomethyl ether | 20 parts |
| 2-heptanone | 20 parts |
| γ-butyrolactone | 3.5 parts |

TABLE 5

| | Resin (A) (Parts) | Acid generator (Parts) | Basic compound (C) (Parts) | PB/PEB (° C.) |
|---|---|---|---|---|
| Ex. 4 | A1 = 10 | I-3 = 1 | C1 = 0.07 | 100° C./90° C. |
| Ex. 5 | A2 = 10 | I-3 = 1 | C1 = 0.07 | 110° C./100° C. |
| Ex. 6 | A2 = 10 | I-3/B1-3 = 0.7/0.3 | C1 = 0.07 | 110° C./100° C. |
| Ex. 7 | A2/X1 = 10/0.7 | I-3 = 1 | C1 = 0.07 | 110° C./100° C. |
| Ex. 8 | A2/X1 = 10/0.7 | I-2 = 1 | C1 = 0.07 | 110° C./100° C. |
| Ex. 9 | A3 = 10 | I-3 = 1 | C1 = 0.07 | 110° C./100° C. |
| Ex. 10 | A4/X1 = 10/0.7 | I-3 = 1 | C1 = 0.07 | 110° C./100° C. |
| Ex. 11 | A4/X1 = 10/0.7 | I-2 = 1 | C1 = 0.07 | 110° C./100° C. |
| Ex. 12 | A4/X1 = 10/0.7 | I-92 = 1 | C1 = 0.07 | 110° C./100° C. |
| Compar. Ex.1 | A3 = 10 | Z1 = 1 | C1 = 0.07 | 110° C./100° C. |

(Preparation of Photoresist Pattern)

Silicon wafers (12 inches) were each coated with "ARC-29", which is an organic anti-reflective coating Composition available from Nissan Chemical Co. Ltd., and then baked at 205° C. for 60 seconds, to form a 78 nm-thick organic anti-reflective coating.

Each of the photoresist compositions prepared as above was spin-coated over the anti-reflective coating so that the thickness of the resulting film became 85 nm after drying. The silicon wafers thus coated with the respective photoresist compositions were each prebaked on a direct hotplate at a temperature shown in "PB" of the column "TB/PEE" in Table 5 for 60 seconds. Using an ArF excimer stepper for immersion exposure ("XT: 1900Gi" manufactured by ASML, NA=1.35, 3/4 Annular, X-Y polarization), each wafer thus formed with the respective resist film was subjected to line and space pattern exposure with the exposure quantity being varied stepwise. At this exposure, a mask which had line and space pattern of 40 nm and a single dummy pattern of 42 nm set at the corner of the line and space pattern was used. Ultra pure water was used for immersion solvent.

After the exposure, each wafer was subjected to post-exposure baking on a hotplate at a temperature shown in "PEB" of the column "PB/PEB" in Table 5 for 60 seconds and then to paddle development for 60 seconds with an aqueous solution of 2.38 wt % tetramethylammonium hydroxide.

Effective Sensitivity (ES) was expressed as the exposure quantity that the line width of the line and space pattern of 50 nm became 1:1 after exposure through line and space pattern mask.

Evaluation of Pattern

The line and space pattern of 50 nm on the obtained film at the exposure quantity equal to the effective sensitivity was observed with a running electron microscope. The pattern whose top and bottom are rectangular shape as shown in FIG. 1 (a) was determined as ◯. The pattern whose top and bottom are a round shape as shown in FIG. 1 (b) was determined as X. The results are shown in Table 6.

Evaluation of Optical Proximity Correction

The dummy pattern of 50 nm on the obtained film was observed with a scanning electron microscope.

The case where the dummy pattern was not existed on the film was determined as ◯. The case where the dummy pattern was existed partly or totally on the film was determined as X. The results are shown in Table 6.

TABLE 6

| | Shape | Dummy pattern |
|---|---|---|
| Ex. 4 | ◯ | ◯ |
| Ex. 5 | ◯ | ◯ |
| Ex. 6 | ◯ | ◯ |
| Ex. 7 | ◯ | ◯ |
| Ex. 8 | ◯ | ◯ |
| Ex. 9 | ◯ | ◯ |
| Ex. 10 | ◯ | ◯ |
| Ex. 11 | ◯ | ◯ |
| Ex. 12 | ◯ | ◯ |
| Compar. Ex.1 | X | X |

Specifically, it was confirmed that the photoresist compositions of Examples 7, 8, 10, 12 and 12 can provide photoresist pattern with few defects among the photoresist compositions of Examples, Since the photoresist composition of the present invention comprises a salt of the present invention, the photoresist composition can provide a photoresist pattern which is accurate, and which is free from a dummy pattern used for optical proximity correction even in case of conducting optical proximity correction with a dummy pattern, as apparent from the above-mentioned examples. The salt and the photoresist pattern of the present invention are suitable for semiconductor microfabrication employing lithography process.

What is claimed is:

1. A salt represented by formula (I):

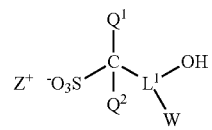

(I)

wherein $Q^1$ and $Q^2$ each independently represent a fluorine atom or a C1-C6 perfluoroalkyl group, the moiety $L^1$-OH of formula (I) is represented by formula ($L^1$-1):

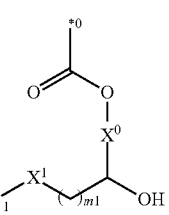

($L^1$-1)

wherein $X^0$ represents a single bond,
a C1-C14 divalent aliphatic hydrocarbon group which can have a fluorine atom or a hydroxyl group, or
a group represented by formula (a-1):

$$-A^{10}-(X^{10}-A^{11})_s-X^{11}-A^{12}-*$$ (a-1)

where s represents an integer of 0 or 1, $X^{10}$ and $X^{11}$ each independently respect an oxygen atom, a carbonyl group, a carbonyloxy group, or an oxycarbonyl group, $A^{10}, A^{11}$ and $A^{12}$ each independently represent a C1-C12 divalent aliphatic hydrocarbon group which can have a fluorine atom or a hydroxyl group, * represents a binding position to a corbon atom, $X^1$ represents —O-$*^1$, —$NR^2$-$*^1$, —O—CO-$*^1$, —O—$CH_2$—CO—O-$*^1$ or —$NR^2$—$CH_2$-$*^1$ where $*^1$ represents a binding position to W, $*^0$ represents a binding position to a carbon atom binding to $Q^1$ and $Q^2$, and $m^1$ represents an integer of 0 to 6, W represents a C3-C36 alicyclic hydrocarbon group in which a methylene group can be replaced by an oxygen atom, a sulfur atom, a carbonyl group or a sulfonyl group, and in which a hydrogen atom can be replaced by a hydroxy group, a C1-C12 alkyl group, a C1-C12 alkoxy group, C3-C18 alicyclic hydrocarbon group or C6-C14 aromatic hydrocarbon group, and $Z^+$ represents an organic cation.

2. The salt according to claim 1, wherein the $X^1$ represents —O-$*^1$, —$NR^2$-$*^1$, —O—CO-$*^1$, —O—$CH_2$-$*^1$, or —$NR^2$—$CH_2$-$*^1$ where $*^1$ represents a binding position to W.

3. The salt according to claim 1, wherein $Z^+$ is an triarylsulfonium cation.

4. A photoresist composition, which comprises the salt according to claim 1 and a resin which is hardly soluble or insoluble but soluble in an aqueous alkali solution by action of an acid.

5. The photoresist composition according to claim 4, which further comprises a basic compound.

6. A process for producing a photoresist pattern comprising the following steps (1) to (5):
    (1) a step of applying the photoresist composition according to claim 4 on a substrate,
    (2) a step of forming a photoresist film by conducting drying,
    (3) a step of exposing the photoresist film to radiation,
    (4) a step of baking the exposed photoresist film, and
    (5) a step of developing the baked photoresist film, thereby forming a photoresist pattern.

* * * * *